US006248870B1

(12) United States Patent
Delecki et al.

(10) Patent No.: US 6,248,870 B1
(45) Date of Patent: *Jun. 19, 2001

(54) UNSYMMETRICAL COMPLEXING AGENTS AND TARGETING IMMUNOREAGENTS USEFUL IN THERAPEUTIC AND DIAGNOSTIC COMPOSITIONS AND METHODS

(75) Inventors: Daniel J. Delecki, Upper Merion Township, Montgomery County; Ashis Kumar Saha, Frazer; Robert A. Snow, West Chester, all of PA (US)

(73) Assignee: Nycomed Imaging AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/139,364

(22) Filed: Aug. 25, 1998

Related U.S. Application Data

(60) Continuation of application No. 08/719,407, filed on Sep. 24, 1996, now Pat. No. 5,817,774, which is a division of application No. 08/069,242, filed on May 28, 1993, now Pat. No. 5,559,214.

(51) Int. Cl.$^7$ ..................................................... C07F 21/55
(52) U.S. Cl. ................................. 534/10; 534/14; 534/15; 534/16; 424/1.65; 424/1.69; 424/9.34
(58) Field of Search .................................... 534/7, 10–16; 424/1.11, 1.65, 1.49, 1.69, 9.1, 9.3, 9.4, 141.1, 130.1; 530/300, 391.5

(56) References Cited

U.S. PATENT DOCUMENTS

| 4,859,777 | 8/1989 | Toner ..................................... 546/256 |
| 4,960,895 | 10/1990 | Ohkawa . |
| 5,104,988 | 4/1992 | Ohkawa . |
| 5,202,423 | 4/1993 | Kankare et al. ................... 530/391.5 |
| 5,292,868 | 3/1994 | Subramanian .................... 530/391.5 |
| 5,367,080 | 11/1994 | Toner et al. . |
| 5,559,214 | * 9/1996 | Delecki et al. .......................... 534/10 |
| 5,583,206 | 12/1996 | Snow et al. ............................. 534/10 |
| 5,817,774 | * 10/1998 | Delecki et al. ......................... 534/10 |

FOREIGN PATENT DOCUMENTS

| WO 90-00550 | 1/1990 | (WO) . |
| WO 92-08494 | 5/1992 | (WO) . |

OTHER PUBLICATIONS

Solomons, Organic Chemistry, 1986, pp. 896–897.

Tsukube et al., Chemistry Letters, No. 12, Dec. 1992, pp. 2307–2310.

\* cited by examiner

*Primary Examiner*—Dameron Jones
(74) *Attorney, Agent, or Firm*—Fish & Richardson P.C.

(57) ABSTRACT

A method for diagnostic imaging a site in a patient. The method involves the use of an immunoreactive group which is linked to an unsymmetrical oligo-2,6-pyrimidine complexing agent.

20 Claims, No Drawings

UNSYMMETRICAL COMPLEXING AGENTS AND TARGETING IMMUNOREAGENTS USEFUL IN THERAPEUTIC AND DIAGNOSTIC COMPOSITIONS AND METHODS

This is a continuation of application Ser. No. 08/719,407, filed Sep. 24, 1996, now U.S. Pat. No. 5,817,774, which is a divisional of application Ser. No. 08/069,242, filed on May 28, 1993, now U.S. Pat. No. 5,559,214.

FIELD OF THE INVENTION

The present invention relates to novel unsymmetrical oligo-2,6-pyridine complexing agents as well as to novel immunoreagents, preferably targeting radioactive immunoreagents, which comprise the novel unsymmetrical oligo-2,6-pyridine complexing agents, and which find particular utility in therapeutic and diagnostic imaging compositions and methods.

BACKGROUND OF THE INVENTION

The use of oligo-2,6-pyridines as complexing agents that may be incorporated in targeting immunoreagents is disclosed, for example, in WO 92/08494 (PCT/US91/08253).

As discussed in WO 92/08494, these complexing agents solve several problems in the prior art, particularly as regards therapeutic and diagnostic imaging uses of targeting radioactive immunoreagents. The targeting radioactive immunoreagents of that patent application comprise a metal radionuclide ion, a complexing agent, and an immunoreactive group covalently bonded through a protein reactive group to the complexing agent.

The complexing agents of that application have the general structure A–I

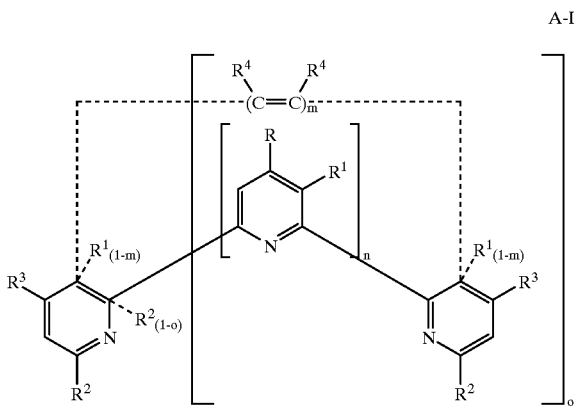

A-I wherein

R represents hydrogen, alkyl, alkoxy, alkylthio, alkylamino, alkylformamido, aryl, aryloxy, heterocyclyl or a protein reactive group;

$R^1$ represents hydrogen, alkyl, alkoxy, alkylthio, alkylamino, alkylformamido, aryl, aryloxy, heterocyclyl or a protein reactive group;

$R^2$ represents hydroxy, carboxy, hydroxyalkyl, thioalkyl, carbonyliminodiacetic acid, methyleneiminodiacetic acid, methylenethioethyleneiminodiacetic acid, carboxyalkythioalkyl, hydrazinylidenediacetic acid, or a salt of such acids, or two $R^2$ groups, taken together, represent the atoms necessary to complete a macrocyclic ring structure containing at least one heteroatom coordinating site and at least one, preferably two, alkylene groups forming part of the ring structure;

$R^3$ represents hydrogen, alkyl, alkoxy, alkylthio, alkylamino, alkylformamido, aryl, aryloxy, heterocyclyl or a protein reactive group;

$R^4$ represents hydrogen or a protein reactive group;

n is 1, 2, 3 or 4;

o is 0 or 1;

m is 0 or 1;

provided that at least one of n and m is 0 and at least one of R, $R^1$, $R^3$ and $R^4$ is a protein reactive group.

While a significant advance over the prior art, one limitation regarding those oligo-2,6-pyridine chelators of structure A–I which contain 3, 4, 5, or 6 pyridine rings is their requirement of substitution by $R^2$ at both the 6-position of the first pyridine ring and the respective 6"-, 6'"-, 6""- and 6""'-positions of the third, fourth, fifth, and sixth pyridine ring. In the synthesis of these compounds, each $R^2$ substitutent requires at least one chemical reaction to occur at some point in the synthetic sequence at both the 6-position of the first pyridine ring and at the respective 6"-, 6'"-, 6""- and 6""'-positions of the third, fourth, fifth, and sixth pyridine ring of the oligo-2,6-pyridines, and the overall yield of the oligo-2,6-pyridine chelator comprises the arithmetical product of the yield of the reaction to generate the appropriate $R^2$ at each of the two reaction sites. This yield is necessarily reduced to less than 100% when one of the reactions involving introduction and/or modification of the substituent at the 6-position and the substituents at the respective 6"-, 6'", 6""- and 6""'-positions is less than 100%, as is most often the case.

Furthermore, in those non-macrocyclic oligo-2,6-pyridine chelators of structure A–I which contain 3, 4, 5, or 6 pyridine rings, wherein each $R^2$ represents hydroxy, carboxy, hydroxyalkyl, thioalkyl, carbonyliminodiacetic acid, methyleneiminodiacetic acid, methylenethioethyleneiminodiacetic acid, carboxyalkythioalkyl, hydrazinylidenediacetic acid, or a salt of such acids, the capacity of a given chelator to bind with a high binding constant to a given metal ion of a fixed charge is limited by conformational energies attainable by the oligo-2,6-pyridine molecular geometry. The molecular geometry and conformational strain energies impose a limit to the amount of interpyridine bond angle bending that can occur in the oligo-2,6-pyridine component. In an s-cis configuration, the restrictions in the interpyridine bond angle bending in the oligo-2,6-pyridine component limit the extent to which the two $R^2$ groups can approach one another and participate with the oligo-2,6-pyridine nitrogens in the chelation of a metal ion. Consequently, the configuration that the chelating moiety can achieve about a metal ion can be limited with respect to attainment of rapid kinetics of metal binding and large binding constant between the chelator and the metal than can be achieved with a chelating oligo-2,6-pyridine that is not constrained by the interpyridine bond energies.

With respect to chelated radioisotopes by the oligo-2,6-pyridines disclosed in WO 92/08494 and incorporated in targeting immunoreagents (radioimmunoconjugates) which comprise an immunoreactive agent, a chelating group and a metal ion, it is advantageous to be able to detect the accumulation of said radioimmunoconjugate at a tumor site so as to be able to better monitor the course of treatment of a patient with said radioimmunoconjugate. Few metal ion radioisotopes have properties which are optimally suited for both diagnostic imaging and for therapeutic applications. As such it is often necessary to use two different metal ions such as, for example, $^{111}In^{+3}$ for diagnostic imaging purposes and such as, for example, $^{90}Y^{+3}$ for therapeutic purposes in the above application. Because these metal ions have different sizes and chelate binding requirements, and although the oligo-2,6-pyridines disclosed in WO 92/08494 bind these metal ions rapidly and hold them tenaciously, there is still a limit to the respective binding rates and binding constants that is imposed by the disubstituted nature of the oligo-2,6-pyridines outlined above.

It is, therefore, desireable to have oligo-2,6-pyridine chelating agents that are not limited in their ability to bind a metal ion because of restrictions imposed by the interpyridine binding energetics and which oligo-2,6-pyridine chelating agents are capable of binding both a diagnostic imaging isotope and a therapeutic isotope rapidly and with a high binding constant.

SUMMARY OF THE INVENTION

In accordance with the present invention, there are provided novel 6-substituted-6'$^{(i-1)}$-H-oligo-2,6-pyridine-containing complexing (or chelating) agents containing i pyridine rings which are derivatives of a terpyridine (i=3), or a quaterpyridine (i=4), or a quinquepyridine (i=5) or a sexipyridine (i=6) and in which the substituent in the 6-position is a chelating group capable of chelating to a metal ion. These novel oligo-2,6-pyridine-containing complexing (or chelating) agents (sometimes hereinafter referred to as unsymmetrical oligo-2,6-pyridine complexing agents or unsymmetrical oligo-2,6-pyridine chelating agents) have the advantage over chelating agents of the prior art in that they can form metal ion complexes comprising a metal ion, a chelating substituent in the 6-position of an oligo-2,6-pyridine and pyridine rings of the oligo-2,6-pyridine in which complexes the energies arising from interpyridine bond angle bending in the oligo-2,6-pyridine component do not limit the chelating interaction of the 6-position substituent with the metal ion. As such, the novel unsymmetrical oligo-2,6-pyridine chelating agents of this invention are capable of binding rapidly and of binding tenaciously to a variety of metal ions which metal ions differ from one another in charge, size and coordination geometry.

Novel radioimmunoconjugates containing the novel unsymmetrical oligo-2,6-pyridine chelating agents of this invention have the advantage that they can be employed in both diagnostic imaging as well as therapeutic applications, particularly in the diagnosis and treatment of cancer such that, in diagnostic imaging of a tumor tissue, the novel radioimmunoconjugate can comprise an immunoreactive agent, a novel chelating group of this invention, and a metal ion isotope useful for diagnostic imaging of said tumor tissue, and, in therapeutic treatment of said tumor tissue, the novel radioimmunoconjugate can comprise said immunoreactive agent, said chelating group, and a therapeutically useful metal ion isotope. These radioimmunoconjugates have the advantage that the same chelating agent and the immunoreactive agent modified to the same extent by said chelating agent can be employed using a radioisotope of a metal ion effective for diagnostic imaging of a tumor tissue and a radioisotope of a different metal ion effective for therapy of the same tumor tissue.

The unsymmetrical oligo-2,6-pyridine chelating agents of this invention can be designed to maximize their binding affinity for (a) a selected diagnostic imaging radionuclide and (b) a selected therapeutic radionuclide (or any other desired combination of two radionuclides, both of which may be therapeutic or for imaging purposes, depending on the needs of the situation). Moreover, this desired introduction of two different radionuclides separately into the same radioimmunoconjugate can be achieved, in accordance with the present invention, without complicating the linking chemistry involved in creating, nor the ultimate reproducibility of, the immunoconjugate containing the complexing agent, since only a single species of complexing agent is used to bind both radionuclides in the radioimmunoconjugate.

More particularly, the present invention provides novel complexing agents having the structure I:

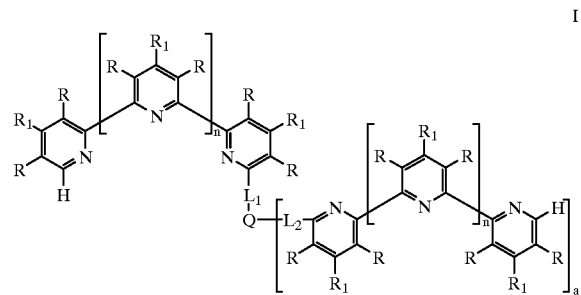

wherein
each R and $R_1$ is independently selected from hydrogen, alkyl, alkoxy, alkylthio, N,N-dialkylamino, alkylformamido, aryl, heterocyclyl, and a protein reactive group;

each of $L_1$ and $L_2$ is a linking group independently selected from a chemical bond, a methylene group (—$CH_2$—), and an imino group;

Q is the residue of a chelating group;

each n is independently 1, 2, 3 or 4; and a is 0 or 1.

This invention also provides metal chelates, sometimes hereinafter referred to as complexes or as metal complexes, comprising complexing agents having the foregoing structure I bound to one or more metal ions.

In another embodiment, this invention provides a targeting immunoreagent comprising a metal ion, a complexing agent, and an immunoreactive group attached through a linking group to said complexing agent, wherein the complexing agent has the structure I as defined above and the linking group between the complexing agent and the immunoreactive group comprises the residue of a protein reactive group on the complexing agent.

In another embodiment, this invention provides a targeting radioactive immunoreagent (sometimes hereinafter referred to as a radioimmunoconjugate) comprising a metal radionuclide ion, a complexing agent, and an immunoreactive group attached through a linking group to said complexing agent, wherein the completing agent has the structure I as defined above and the linking group between the completing agent and the immunoreactive group comprises the residue of a protein reactive group on the complexing agent.

In another embodiment, this invention provides a targeting paramagnetic immunoreagent comprising a paramagnetic metal ion, a completing agent, and an immunoreactive group attached through a linking group to said complexing agent, wherein the complexing agent has the structure I as defined above and the linking group between the complexing agent and the immunoreactive group comprises the residue of a protein reactive group on the complexing agent.

In another embodiment, this invention provides a targeting fluorescent immunoreagent comprising a fluorescent metal ion, a completing agent, and an immunoreactive group attached through a linking group to said complexing agent, wherein the complexing agent has the structure I as defined above and the linking group between the completing agent and the immunoreactive group comprises the residue of a protein reactive group on the complexing agent.

This invention also provides therapeutic and diagnostic compositions comprising the above-described targeting radioactive immunoreagents.

This invention also provides diagnostic compositions comprising the above-described targeting paramagnetic immunoreagents.

This invention also provides diagnostic compositions comprising the above-described targeting fluorescent immunoreagents.

This invention further provides a method for diagnostic imaging a site in a patient comprising a) administering to the patient an effective amount, in a pharmaceutically acceptable carrier, of the above-described radioactive immunoreagent capable of targeting the site, and b) imagewise activating a radiation-sensitive element or device, such as, for example, a film or electronic sensor, with the radiation emitted from the targeted site.

This invention further provides a method for diagnostic imaging a site in a patient comprising a) administering to the patient an effective amount, in a pharmaceutically acceptable carrier therefor, of the above-described paramagnetic immunoreagent capable of targeting the site, and b) imagewise activating a nuclear magnetic resonance detection sensor element or device which is sensitive to a change in one or more nuclear magnetic relaxation properties of an isotope such as a proton at the site of the patient while exposed to a controlled magnetic field environment such as, for example, a magnetic field in a magnetic resonance imaging instrument, which change is induced by the paramagnetic metal ion of the immunoreagent.

This invention further provides a method for diagnostic imaging a site in a specimen comprising a) administering to the specimen an effective amount of a fluorescent composition comprising the above-described fluorescent immunoreagent capable of targeting a site in the specimen, b) irradiating the specimen with light, and c) imagewise activating a fluorescence emission sensor element or device, such as, for example, a film or electronic sensor, with the fluorescent light emitted from the targeted site.

This invention further provides a method for treating a disease site in a patient comprising administering to the patient or a specimen from the patient an effective amount, in a pharmaceutically acceptable carrier therefor, of a therapeutic composition comprising the above-described radioactive immunoreagent capable of targeting the site.

It is an advantageous feature of this invention that the targeting immunoreagents of this invention are not rapidly metabolized and do not deleteriously disperse.

It is another advantageous feature that the described complexes containing a protein reactive group efficiently attach to proteins and other biological molecules.

Yet another advantageous feature of this invention is that the described complexes exhibit photometric emissions which have a low signal to noise ratio, good energy emission characteristics, and which are readily subject to spectrophotometric analysis.

Additionally, protein conjugates of the complexing agents can be formed and stored until metal complexation is desired, and complexation can be accomplished without activation steps that degrade protein.

Moreover, the complexing agents rapidly complex with metals, and the resulting chelates exhibit excellent stability with respect to time, temperature and pH.

It is an advantageous feature of this invention that the targeting immunoreagents of this invention comprising an immunoreactive group, a novel chelating agent of this invention, and a metal ion can be used both to image tumors using a diagnostically useful metal ion radioisotope and to separately treat tumors using a therapeutically useful metal ion radioisotope.

Other advantageous features of this invention will become readily apparent upon reference to the following description of the preferred embodiments and specific examples.

DESCRIPTION OF PREFERRED EMBODIMENTS

The description which follows primarily concerns the novel complexing agents of the invention and their metal complexes, as well as usage of the targeting immunoreagents of the invention in therapeutic and diagnostic imaging compositions and methods. In addition, the complexing agents, metal chelates of complexing agents, and targeting radioactive immunoreagents of the invention are useful as diagnostic reagents, for example, as radioimmunoelectro-phoresis reagents.

The complexing agents of this invention comprise 6-substituted oligo-2,6-pyridines which are derivatives of a terpyridine, or a quaterpyridine, or a quinquepyridine or a sexipyridine and which have the structural formula I recited in the Summary above.

Each R and $R_1$ in structure I independently is selected from:

hydrogen;

alkyl such as straight or branched chain or cyclic or substituted alkyl, the alkyl portion of which preferably contains from 1 to about 20 carbon atoms, such as methyl, ethyl, propyl, isopropyl, butyl, s-butyl, t-butyl, 2-ethylhexyl, decyl, hexadecyl, octadecyl, cyclohexyl, cyclopropyl, etc.;

substituted alkyl such as hydroxyalkyl, the alkylene portion of which is a straight or branched chain or cyclic alkylene group, preferably containing from 1 to about 20 carbon atoms, such as methylene, ethylene, propylene, isopropylene, butylene, s-butylene, t-butylene, 2-ethylhexylene, decylene, hexadecylene, octadecylene, cyclohexylene, cyclohexanedimethylene, cyclopropylene, etc.;

substituted alkyl such as alkoxyalkyl, the alkyl portion of which contains from 1 to about 20 carbon atoms as described above for alkyl, and the alkylene portion of which is a straight or branched chain or cyclic alkylene group which contains from 1 to about 20 carbon atoms as described above for alkylene;

substituted alkyl such as alkylthioalkyl, the alkyl portion of which contains from 1 to about 20 carbon atoms as described above for alkyl, and the alkylene portion of which is a residue of an alkyl group which contains from 1 to about 20 carbon atoms as described above for alkylene;

substituted alkyl such as hydroxyalkylthioalkyl, the alkylene of the hydroxyalkyl portion of which contains from 2 to about 20 carbon atoms as described above for alkylene, the sulfur and oxygen atoms of which are separated by at least two carbon atoms, and the alkylene of the thioalkyl portion of which independently contains from 1 to about 20 carbon atoms as described above for alkylene;

substituted alkyl such as N,N-dialkylaminoalkyl, the alkyl of each of the N,N-alkyl portions of which independently contains from 1 to about 20 carbon atoms as described above for alkyl, and the alkylene portion of which contains from 2 to about 20 carbon atoms as described above for alkylene;

substituted alkyl such as N-hydroxyalkyl-N-alkylaminoalkyl, the alkylene of the N-hydroxyalkyl portion of which contains from 2 to about 20 carbon atoms as described above for alkylene, the oxygen and nitrogen atoms of which are separated by at least two carbon atoms, the alkyl of the N-alkylamino portion of which contains from 1 to about 20 carbon atoms as described above for alkyl, and the alkylene portion of which contains from 2 to about 20 carbon atoms as described above for alkylene;

substituted alkyl such as N,N-bis(hydroxyalkyl)-aminoalkyl, the alkylene of each hydroxyalkyl portion of which independently contains from 2 to about 20 carbon atoms as described above for alkylene, the oxygen and nitrogen atoms of which are separated by at least two carbon atoms, and the alkylene of the aminoalkyl portion of which contains from 1 to about 20 carbon atoms as described above for alkylene;

substituted alkyl such as formamidoalkyl, the alkylene portion of which contains from 1 to about 20 carbon atoms as described above for alkylene;

substituted alkyl such as alkylformamidoalkyl, the alkyl portion of which contains from 1 to about 20 carbon atoms as described above for alkyl, and the alkylene portion of which contains from 1 to about 20 carbon atoms as described above for alkylene;

alkoxy, the alkyl portion of which contains from 1 to about 20 carbon atoms as described above for alkyl;

substituted alkoxy such as hydroxyalkyloxy, the alkylene portion of which is a straight or branched chain or cyclic alkylene group which contains from 2 to about 20 carbon atoms as described above for alkylene, and the oxygen atoms of which are separated by at least two carbon atoms;

substituted alkoxy such as alkoxyalkyloxy, the alkyl portion of which contains from 1 to about 20 carbon atoms as described above for alkyl, and the alkylene portion of which contains from 2 to about 20 carbon atoms as described above for alkylene, and the oxygen atoms of which are separated by at least two carbon atoms;

substituted alkoxy such as alkylthioalkyloxy, the alkyl portion of which contains from 1 to about 20 carbon atoms as described above for alkyl, and the alkylene portion of which contains from 2 to about 20 carbon atoms as described above for alkylene, and the oxygen and sulfur atoms of which are separated by at least two carbon atoms;

substituted alkoxy such as hydroxyalkylthioalkyloxy, the alkylene portions of which independently contain from 2 to about 20 carbon atoms as described above for alkylene and the sulfur and oxygen atoms of which are separated by at least two carbon atoms;

alkylthio, the alkyl portion of which contains from 1 to about 20 carbon atoms as described above for alkyl;

substituted alkylthio such as hydroxyalkylthio, the alkylene portion of which contains from 2 to about 20 carbon atoms as described above for alkylene, and the oxygen and sulfur atoms of which are separated by at least two carbon atoms;

N,N-dialkylamino, each alkyl portion of which independently contains from 1 to about 20 carbon atoms as described above for alkyl;

substituted N,N-dialkylamino such as N-hydroxyalkyl-N-alkylamino, the alkylene of the N-hydroxyalkyl portion of which contains from 2 to about 20 carbon atoms as described above for alkylene, the oxygen and nitrogen atoms of which are separated by at least two carbon atoms, and the N-alkyl portion of which contains from 1 to about 20 carbon atoms as described for alkyl above;

substituted N,N-dialkylamino such as N,N-bis(hydroxyalkyl)amino, the alkylene of each N-hydroxyalkyl portion of which contains from 2 to about 20 carbon atoms as described above for alkylene and the oxygen and nitrogen atoms of which are separated by at least two carbon atoms;

alkylformamido, the alkyl portion of which contains from 1 to about 20 carbon atoms as described above for alkyl;

aryl preferably containing from about 6 to 24 carbon atoms such as phenyl, naphthyl, benzopyrenyl, and phenanthryl;

substituted aryl such as alkylaryl wherein the alkyl portion is as defined above and the aryl as defined above, such as tolyl, xylyl, 2-(2,3-dimethoxypropoxy) ethylphenyl, 4-(3-t-butoxypropyl)naphthyl, and ethylphenyl;

substituted aryl such as nitroaryl, wherein the aryl portion as defined above, such as nitrophenyl;

substituted aryl such as cyanoaryl, wherein the aryl portion as defined above, such as cyanonaphthyl and cyanophenyl;

chloro-, bromo-, fluor- and iodo-substituted aryl, wherein the aryl portion as defined above, such as chlorophenyl, iodophenyl, and pentafluorophenyl;

aryl substituted aryl such as arylaryl, wherein each of the aryl portions are independently aryl and may be substituted as defined above, such as biphenyl and 4-[9-(10-methylanthracenyl)]-phenyl;

substituted aryl such as N,N-dialkylaminoaryl, wherein the aryl portion as defined above and the N,N-dialkylamino portion as defined above, such as N-hexadecyl-N-methylaminophenyl and N-methyl-N-octadecylaminophenyl;

substituted aryl such as alkoxyaryl wherein the aryl portion as defined above and the alkyl portion as defined above, such as methoxyphenyl, methylenedioxyphenyl, methoxyethoxyphenyl, dimethoxyphenyl, phenoxyphenyl, 4-methoxy-3-iodophenyl, and 4-methoxy-3-N,N-dimethylphenyl, 4-(2 -hydroxyethoxy)phenyl, 5-hydroxypropoxy-3,4-methylenedioxyphenyl, 4-(2-methoxyethoxy) ethylphenyl, and 2-(4-methoxy)napthyl;

substituted aryl such as alkylthioaryl wherein the aryl portion as defined above and the alkyl portion as defined above, such as methylthiophenyl and 4-(2-ethylthio)phenyl;

substituted aryl such as alkylformamidoaryl wherein the aryl portion as defined above and the alkyl portion as defined above, such as N-butylformamidonaphthyl;

substituted aryl such as carboxylaryl, sulfonatoaryl, and hydroxyaryl, wherein the aryl portion as defined above such as hydroxyphenyl, carboxyphenyl, dicarboxyphenyl, hydroxybenzopyrenyl, hydroxyethylphenyl, bis(hydroxymethyl)phenyl, dihydroxycyclohexylphenyl, hydroxymethylanthracenyl, and sulfonatophenyl;

substituted aryl such as alkoxyalkyloxyaryl, the alkyl portion of which contains from 1 to about 20 carbon atoms as described above for alkyl, the alkylene portion of which contains from 2 to about 20 carbon atoms as described above for alkylene, the oxygen atoms of which are separated by at least two carbon atoms such as, for example, 4-(2-ethoxyethoxy)phenyl, methoxyethoxynaphthyl, methoxyethoxyphenyl, 3,4-bis(2-methoxyethoxy)phenyl, 4-W-methoxy-poly(ethylene oxidyl)phenyl, the poly(ethylene oxidyl) portion of which contains from 2 to 100 recurring units of ethylene oxide;

substituted aryl such as hydroxyalkylthioaryl, the alkylene portion of which contains from 2 to about 20 carbon atoms as described above for alkylene, the oxygen and sulfur atoms of which are separated by at least two carbon atoms, and the arylene portion of which contains from 6 to about 24 carbon atoms as described above for arylene, for example, 2-hydroxyethylthiophenyl, 2,3-dihydroxypropylthiophenyl, and 4-(2,3-dihydroxypropyl)thio-3-methoxyphenyl;

substituted aryl such as hydroxyalkylthioalkylaryl, the hydroxyalkylthio portion of which contains an alkylene group having from 2 to about 20 carbon atoms as described above for alkylene, the oxygen and sulfur atoms of which are separated by at least two carbon atoms, the alkylene of the thioalkylaryl portion of which contains from 1 to about 20 carbon atoms as described above for alkylene, and the arylene portion of which contains from 6 to about 24 carbon atoms as described above for arylene, for example, (2-hydroxyethyl)thiomethylphenyl, 2-(2,3-dihydroxypropyl)thioethylphenyl, and 4-[(2,3-dihydroxypropyl)thiomethyl]phenyl;

substituted aryl such as hydroxyalkylthioalkylaryl, the hydroxyalkylthio portion of which contains an alkylene group having from 2 to about 20 carbon atoms as described above for alkylene, the oxygen and sulfur atoms of which are separated by at least two carbon atoms, the alkylene of the thioalkylaryl portion of which contains from 1 to about 20 carbon atoms as described above for alkylene, and the arylene portion of which contains from 6 to about 24 carbon atoms as described above for arylene, for example, (2-hydroxyethyl)thiomethylphenyl, 2-(2,3-dihydroxypropyl)thioethylphenyl, and 4-[(2,3-dihydroxypropyl)thiomethyl]phenyl;

hydroxyalkylthioalkyloxyaryl, each alkylene portion of which independently contains from 2 to about 20 carbon atoms as described above for alkylene, the oxygen and sulfur atoms of which are separated by at least two carbon atoms, and the arylene portion of which contains from 6 to about 24 carbon atoms as described above for arylene, for example, 4-[2-(2-hydroxyethyl)thioethoxy]phenyl, and 4,5-bis[2-(2-hydroxyethyl)thioethoxy]naphthyl;

aryloxy, the aryl portion of which contains from 6 to about 24 carbon atoms as described above for aryl, which aryl may be substituted as described above, such as phenoxy, nitrophenoxy, bromophenoxy, biphenyloxy, carboxyphenoxy, and sulfonatophenoxy;

substituted alkyl such as aralkyl, the alkylene portion of which contains from 1 to about 20 carbon atoms as described above for alkylene and the aryl portion of which contains from about 6 to 24 carbon atoms as described above for aryl, for example, benzyl, benzhydryl, trimethylbenzyl; and 9-(10-methyl)anthracenyl;

substituted aralkyloxy, the alkylene portion of which contains from 1 to about 20 carbon atoms as described above for alkylene, and the aryl portion of which contains from about 6 to 24 carbon atoms as described above for aryl, for example, benzyloxy, methylenedioxybenzyloxy, 2-(methylenedioxyphenyl)ethoxy and phenylethoxy;

substituted alkyl such as alkoxyaralkyl, the alkylene portion of which contains from 1 to about 20 carbon atoms as described for alkylene above, the alkyl portion of which contains from 1 to about 20 carbon atoms as described above for alkyl, and the arylene portion of which contains from about 6 to 24 carbon atoms as described above for arylene, for example, 3-(2,3-dimethoxypropoxy)benzyl, methoxybenzyl, and 4-poly(ethylene oxidyl)benzyl, the poly(ethylene oxidyl) portion of which contains from 2 to 100 recurring units of ethylene oxide;

substituted alkyloxy such as alkoxyaralkyloxy, the alkyl portion of which contains from 1 to about 20 carbon atoms as described above for alkyl, the alkylene portion of which contains from 1 to about 20 carbon atoms as described above for alkylene, and the arylene portion of which contains from about 6 to 24 carbon atoms as described above for arylene, for example, 3-(2,3-dimethoxypropoxy)benzyloxy, methoxybenzyloxy, and 4-W-methoxy-poly(ethylene oxidyl)benzyloxy, the poly(ethylene oxidyl) portion of which contains from 2 to 100 recurring units of ethylene oxide;

substituted aryloxy such as alkylaryloxy, the alkyl portion of which contains from 1 to about 20 carbon atoms as described above for alkyl, and the arylene portion of which contains from about 6 to 24 carbon atoms as described above for arylene, for example, methylphenoxy, cyclohexylphenoxy, and butylphenoxy;

substituted alkyloxy such as alkoxyaryloxy, the alkyl portion of which contains from 1 to about 20 carbon atoms as described above for alkyl, and the arylene portion of which contains from about 6 to 24 carbon atoms as described above for arylene, for example, methoxyphenoxy and 4-poly(ethylene oxidyl)phenoxy, the poly(ethylene oxidyl) portion of which contains from 2 to 100 recurring units of ethylene oxide;

substituted or unsubstituted heterocyclyl, containing from 5 to about 36 total nuclear carbon and heteroatoms and preferably comprising one ore more rings comprised of 5 or 6 nuclear carbon and heteroatoms such as N, S, P or O, for example, pyridyl, methylpyridyl, N-morpholino, dimethylaminopyridyl, methoxypropylpyridyl, oxazolyl, imidazolyl, pyrazolyl, quinolyl, thiazinyl, furanyl, pyranyl, and dimethylphosphazinyl;

substituted alkyl group containing a protein reactive group, which protein reactive group is defined hereinbelow;

substituted alkoxy group containing a protein reactive group, which protein reactive group is defined hereinbelow;

substituted alkylthio group containing a protein reactive group, which protein reactive group is defined hereinbelow;

substituted N,N-dialkylamino group containing a protein reactive group, which protein reactive group is defined hereinbelow;

substituted alkylformamido group containing a protein reactive group, which protein reactive group is defined hereinbelow;

substituted aryl group containing a protein reactive group, which protein reactive group is defined hereinbelow;

substituted heterocyclyl group containing a protein reactive group, which protein reactive group is defined hereinbelow; and, a protein reactive group as defined hereinbelow.

In presently preferred embodiments, R is hydrogen and $R_1$ is a phenyl group, a 4-nitrophenyl group, a 4-alkoxyphenyl group, preferably 4-methoxyphenyl group, or a 4-alkoxyphenyl group additionally substituted with a protein reactive group as defined below.

Each of $L_1$ and $L_2$ in structure I is a linking group independently selected from:

a chemical bond;

a methylene group (—$CH_2$—); or an imino group such as —NR"—, wherein R" is selected from a group consisting of hydrogen, an alkyl group as described above, and the residue of a chelating group as described below. Preferably, R" is a hydrogen or a methyl group.

Each n in structure I is independently 1, 2, 3 or 4; and, a is 0 or 1.

In structure I, Q is the residue of a chelating group. A chelating group as used herein comprises the residue of one or more of a wide variety of chelating agents that can have a metal ion associated therewith. The chelating group may also comprise, as a part thereof, a protein reactive group, for example, a vinyl sulfone group, as exemplified by compounds 44 and 50 hereinafter. As is well known, a chelating agent is a compound containing donor atoms that can combine by coordinate bonding with a metal atom to form a cyclic structure called a chelation complex or chelate. This class of compounds is described in the Kirk-Othmer Encyclopedia of Chemical Technology, Vol. 5, 339–368.

The residue of a suitable chelating agent can be selected from polyphosphates, such as sodium tripolyphosphate and hexametaphosphoric acid; aminocarboxylic acids, such as ethylenediaminetetraacetic acid, N-(2-hydroxyethyl) ethylene-diaminetriacetic acid, nitrilotriacetic acid, N,N-di (2-hydroxyethyl)glycine, ethylenebis (hydroxyphenylglycine) and diethylenetriamine pentacetic acid; 1,3-diketones, such as acetylacetone, trifluoroacetylacetone, and thenoyltrifluoroacetone; hydroxycarboxylic acids, such as tartaric acid, citric acid, gluconic acid, and 5-sulfosalicylic acid; polyamines, such as ethylenediamine, diethylenetriamine, triethylenetetramine, and triaminotriethylamine; aminoalcohols, such as triethanolamine and N-(2-hydroxyethyl)ethylenediamine; aromatic heterocyclic bases, such as 2,2'-diimidazole, picoline amine, dipicoline amine and 1,10-phenanthroline; phenols, such as salicylaldehyde, disulfopyrocatechol, and chromotropic acid; aminophenols, such as 8-hydroxyquinoline and oximesulfonic acid; oximes, such as dimethylglyoxime and salicylaldoxime; peptides containing proximal chelating functionality such as polycysteine, polyhistidine, polyaspartic acid, polyglutamic acid, or combinations of such amino acids; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocylic compounds, such as dibenzo[18]crown-6, $(CH_3)_6$-[14]-4,11-diene-$N_4$, and (2.2.2-cryptate); phosphonic acids, such as nitrilotrimethylene-phosphonic acid, ethylenediaminetetra (methylenephosphonic acid), and hydroxyethylidenediphosphonic acid, or combinations of two or more of the above agents.

The residue of a suitable chelating agent preferably comprises a polycarboxylic acid group and includes: ethylenediamine-N, N, N',N'-tetraacetic acid (EDTA); N,N, N',N'',N''-diethylene-triaminepentaacetic acid (DTPA); 1,4, 7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans(1,2)-cyclohexanodiethylenetriamine pentaacetic acid (CDTPA).

In one aspect, other suitable residues of chelating agents comprise proteins modified for the chelation of metals such as technetium and rhenium as described in U.S. Pat. No. 5,078,985, the disclosure of which is hereby incorporated by reference.

In another aspect, suitable residues of chelating agents are derived from N3S and N2S2 containing compounds, as for example, those disclosed in U.S. Pat. Nos. 4,444,690; 4,670, 545; 4,673,562; 4,897,255; 4,965,392; 4,980,147; 4,988, 496; 5,021,556 and 5,075,099.

Other suitable residues of chelating agents are described in PCT/US91/08253, the disclosure of which is hereby incorporated by reference. In structure I above, if Q comprises the residue of multiple chelating agents, such agents can be linked together by linking groups such as described below.

Preferred chelating groups are selected from the group consisting of 2-aminomethylpyridine, iminoacetic acid, iminodiacetic acid, ethylenediaminetetraacetic acid (EDTA), diethylenetriaminepentaacetic acid (DTPA), 1,4,7,10-tetraazacyclododecane-1,4,7,10-tetraacetic acid (DOTA), carbonyliminodiacetic acid, methyleneiminoacetic acid, methyleneiminodiacetic acid, ethylenethioethyleneiminoacetic acid, ethylenethioethyleneiminodiacetic acid, or a salt of any of the foregoing acids. An especially preferred chelating group is DTPA.

As used herein, "protein reactive group" refers to one or more R and $R_1$ groups which can react with a reactive functional group typically found on or introduced into a protein, especially an immunoreactive protein, to form a linking group between the complexing agent and the protein. However, it is specifically contemplated that a protein reactive group can be used to conjugate a complexing agent of this invention to a non-protein biomolecule as well as to a non-biological molecule such as a synthetic chemical substance (for example, a drug) that is of interest, for example, for the purposes of detection of such a molecule in a mixture which may contain such a synthetic chemical substance and which substance contains a group that is reactive with the protein reactive group. Thus, the protein reactive groups useful in the practice of this invention include those groups which can react with any molecule, preferably a biological molecule (such as a protein, a carbohydrate, a nucleic acid, and a lipid) containing a reactive group to form a linking group between the complexing agent and the molecule. Preferably the molecule is a protein, and preferred reactive groups on such protein molecule include amine groups and sulfhydryl groups. Especially preferred biological molecules contain an immunoreactive group as described hereinbelow.

The protein reactive groups useful in the practice of this invention also include those groups which can react with any biological molecule that is chemically modified, for example, by oxidation, by reduction, or by covalent bond formation such as by amide bond formation with another chemical species such as, for example, an amine, an amino acid, a substituted amine, or a substituted amino acid, to introduce a reactive group into the biological molecule, to form a linking group between the complexing agent and the chemically modified biological molecule.

The protein reactive groups useful in the practice of this invention also include those groups which comprise a portion of a specific receptor-ligand interactive group. For example, in the complexing agent of structure I, R, $R_1$ or Q can comprise an oligonucleotide group as a receptor portion of a receptor-ligand interactive group. The complementary oligonucleotide attached to a biological molecule is then a ligand portion of the receptor-ligand interactive group. Said ligand will bind to the receptor to form a linking group between the complexing agent and the biological molecule.

Preferred protein reactive groups can be selected from, but are not limited to, groups that will react directly with an amine group such as a lysine epsilon amine group or a terminal amine group in a peptide or with a sulfhydryl group such as a cysteine sulfhydryl group commonly found on a protein or other biological molecule. Examples of such protein reactive groups include active halogen-containing groups such as chloromethylphenyl groups, chloromethylcarbonyl groups, and iodomethylcarbonyl groups; activated 2-leaving-group-substituted ethylsulfonyl and ethylcarbonyl groups such as 2-chloroethylsulfonyl groups and 2-chloroethylcarbonyl groups; vinylsulfonyl groups; vinylcarbonyl groups; oxiranyl groups; isocyanato groups; isothiocyanato groups; aldehydo groups; aziridyl groups; succinimidoxycarbonyl groups; activated acyl groups such as carboxylic acid halide groups; anhydride groups; thioester groups; carbonates such as nitrophenylcarbonates; sulfonic acid esters; phosphoramidates; cyanuric monochlorides and cyanuric dichlorides; and other groups known to be useful in conventional photographic gelatin hardening agents.

The above listed protein reactive groups can react with a protein or other biological molecule which is chemically modified to contain reactive amine groups and sulfhydryl groups. Amine groups can be introduced by well known techniques such as, for example, nitration of a phenyl group followed by reduction, by conversion of a primary amide to an amine with nitrous acid, by conversion of a hydroxyl group of an alcohol into a sulfonic acid ester followed by displacement with an azide group and subsequent reduction to an amine, and the like. Sulfhydryl groups can be introduced by well known techniques such as, for example, by conversion of a hydroxyl group of an alcohol into a sulfonic acid ester followed by displacement with sodium sulfide, by dehydrative amide bond formation between an amine group of a protein and a carboxylic acid group of an acetylated cysteine using a carbodiimide reagent followed by treatment with hydroxylamine, and the like.

In addition, when a protein or other biological molecule can be chemically modified such as by partial oxidation to introduce an aldehyde group or a carboxylic acid group, a preferred "protein reactive group" can be selected from amino, aminoalkyl, aminoaryl, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 20 carbon atoms as described for R and $R_1$ above, and the aryl portions of the protein reactive group can contain from about 6 to about 24 carbon atoms as described for R and $R_1$ above.

An additional preferred protein reactive group can comprise a residue of a crosslinking agent. A useful crosslinking agent can react with a functional group such as, for example, an amine or sulfhydryl or carboxylic acid group or aldehyde group found in W of Structure I above and with a functional group such as, for example, an amine or sulfhydryl or carboxylic acid group or aldehyde group found in a protein or a biological molecule or in a chemically modified protein or biological molecule such as described above. The residues of certain useful crosslinking agents, such as, for example, difunctional gelatin hardeners, bisepoxides and bisisocyanates become a part of, i.e., a linking group in, a protein-complexing agent conjugate or a biological molecule-complexing agent conjugate which is formed as a result of the crosslinking reaction of such a crosslinking protein reactive group with a complexing agent and also with a protein or also with a biological molecule, respectively.

Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847, the disclosure of which is hereby incorporated herein by reference in its entirety, and the dication ethers of U.S. Pat. No. 4,877,724, the disclosure of which is hereby incorporated herein by reference in its entirety. With these crosslinking agents, one of the reactants must have a carboxyl group and the other an amine or sulfhydryl group. The crosslinking agent first reacts selectively with the carboxyl group, preferably a carboxyl group on a protein, then is split out during reaction of the "activated" carboxyl group with an amine, preferably an amine group of R or $R_1$ in Structure I, to form an amide linkage between the protein or biological molecule and a completing agent of this invention, thus covalently bonding the two moieties. An advantage of this approach is that crosslinking of like molecules, e.g., complexing agents with complexing agents, can be avoided, whereas the reaction of difunctional crosslinking agents is nonselective so that unwanted crosslinked molecules can be obtained.

Additional preferred protein reactive groups include semicarbazido; thiocarbazido; thiosemicarbazido; isocyanato and isothiocyanato; vinyl sulfonylalkyloxy, the alkylene group of which preferably contains from 2 to 10 carbon atoms and is as described for R and $R_1$ above; vinyl sulfonylalkylpoly(oxyalkyl)oxy, the alkylene group of the sulfonylalkyl portion of which preferably contains from 2 to 10 carbon atoms and is as described for R and $R_1$ above, the alkylene group of the polyoxyalkyl portion preferably contains from 2 to 10 carbon atoms and is as described for R and $R_1$ above, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; amidatoalkyloxy, the alkylene group of which preferably contains from 1 to 10 carbon atoms and is as described for R and $R_1$ above; hydrazidoalkyloxy, the alkylene group of which preferably contains from 1 to 10 carbon atoms and is as described for R and $R_1$ above; azidocarbonylalkyloxy, the alkylene group of which preferably contains from 1 to 10 carbon atoms and is as described for R and $R_1$ above; aryloxycarbonyloxyalkyloxy, the alkylene group of which preferably contains from 2 to 10 carbon atoms and is as described for R and $R_1$ above, and the aryl group of which is as described for R and $R_1$ above; aryloxycarbonyl (polyoxyalkyl)oxy, the aryl group of which is as described for R and $R_1$ above, and the alkylene group of the polyoxyalkyl portion preferably contains from 2 to 10 carbon atoms and is as described for R and $R_1$ above, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; triazines such as 4,6-dichloro-2-triazinylamino, 4,6-dichloro-2-triazinyloxy, 4,6-dichlorotriazinyl-2-oxy(polyalkyloxy), 4-alkoxy-6-chloro-2-triazinyloxy, and 4-alkoxy-6-chloro-2-triazinyl (polyoxyalkyl)oxy, the alkyl groups of the alkoxy portions preferably each containing from 2 to 10 carbon atoms and being as described for R and $R_1$ above, and the alkylene groups of the polyoxyalkyl portions preferably each containing from 2 to 10 carbon atoms and being as described for R and $R_1$ above, such a poly(oxyalkyl) portion preferably comprising a poly(oxyethylene) group or a poly(oxyethylene)-co-poly(oxypropylene) copolymer group, in which the polymer contains from 2 to about 100 monomeric oxyalkylene units; formylalkyl, the alkyl group of which preferably contains from 1 to 10 carbon atoms and is as described for R and $R_1$ above; aminoalkyl, the alkyl group of which preferably contains from 1 to 10 carbon atoms and is as described for R and $R_1$ above; active esters, for example, succinimidoxycarbonyl; active anhydrides and mixed anhydrides; active carbonates such as arylcarbonatoaryl, alkylcarbonatoaryl, arylcarbonatoalkyl, and alkylcarbonatoalkyl, the alkyl groups of which preferably contain from 2 to 10 carbon atoms and are as described for R and $R_1$ above, and the aryl groups of which are preferably comprised of a six membered ring containing electron withdrawing substituents such as, for example, nitro and halogen, and optionally containing water solubilizing groups such as a sulfonate salt; sulfhydryl; sulfhydrylalkyl, the alkyl group of which preferably contains from 1 to 10 carbon atoms and is as described for R and $R_1$ above; thioalkylcarbonylaminoalkyloxy, the alkylene group of the thioalkylcarbonyl portion preferably containing from 1 to 10 carbon atoms and being as described for R and $R_1$ above, and the alkylene group of the aminoalkyloxy portion preferably containing from 2 to 10 carbon atoms and being as described for R and $R_1$ above; maleimidoalkylcarbonylaminoalkyloxy, the alkylene group of the maleimidoalkylcarbonyl portion preferably containing from 1 to 10 carbon atoms and being as described for R and $R_1$ above, and the alkylene group of the aminoalkyloxy portion preferably containing from 2 to 10 carbon atoms and being as described for R and $R_1$ above; azido; iodoalkylcarbonylamino, the alkylene group of which contains from 1 to 10 carbon atoms and is as described for R and $R_1$ above; amidatoalkylamino, the alkylene group of which contains from 1 to 10 carbon atoms and is as described for R and $R_1$ above; and amidatoarylalkylamino, the alkylene group of which contains from 1 to 10 carbon atoms and is as described for R and $R_1$ above, and the aryl group of which is as described for R and $R_1$ above.

Especially preferred protein reactive groups include sulfhydryl, amino, isothiocyanato and arylcarbonatoalkyl.

The term "residue" is used herein in the context of a chemical entity comprising, for example, a ligand, or an alkyl group, or a chelating group, or a radioactive agent, or a linking group, or a protein reactive group, or an immunoreactive group, or an immunoreactive material, or an immunoreactive protein, or an antibody, or an antibody fragment, or a cross-linking agent such as a heterobifunctional cross-linking agent and is defined as that portion of said chemical entity which exclusively remains when one or more chemical bonds of which the chemical entity is otherwise comprised when considered as an independent chemical entity, is altered, modified, deleted or replaced to comprise one or more covalent bonds to one or more other chemical entities. For example, in one aspect, a linking group between an immunoreactive group and a chelating agent comprises the residue of a protein reactive group of the chelating agent and the residue of the reactive group on the immunoreactive group with which the protein reactive group reacted. In this regard, when a protein reactive group such as an isothiocyanato group (i.e., an —N=C=S) on a chelating agent reacts with a reactive group such as an amine group (i.e., an $H_2N$-) on an immunoreactive group to form a thioureylene group [i.e., an —NH—C(=S)—HN—] linking the chelating agent with the immunoreactive group, the thioureylene group is a linking group comprising the residue of the protein reactive group and the residue of the amine group.

Preferred classes of complexing agents according to the invention include unsymmetrical 6-substituted-2,2':6',2''-terpyridines having structure II:

Structure II

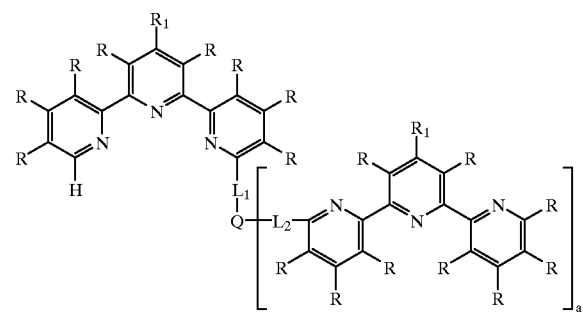

STRUCTURE II wherein R, $R_1$, $L_1$, $L_2$, Q and a are as described above for Structure I.

An especially preferred class of complexing agents according to the invention includes unsymmetrical oligo-2,6-pyridine terpyridines having structure III:

Structure III

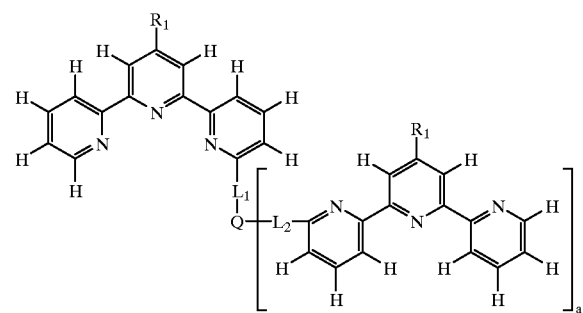

wherein $R_1$, $L_1$, $L_2$ Q, and are as described above for Structure I.

Specific examples of preferred complexing agents according to the invention include:
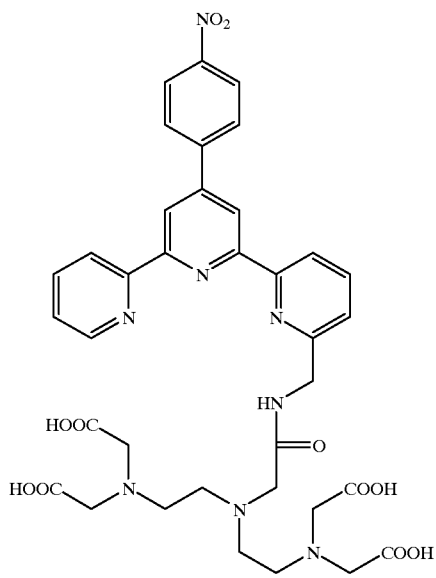
26
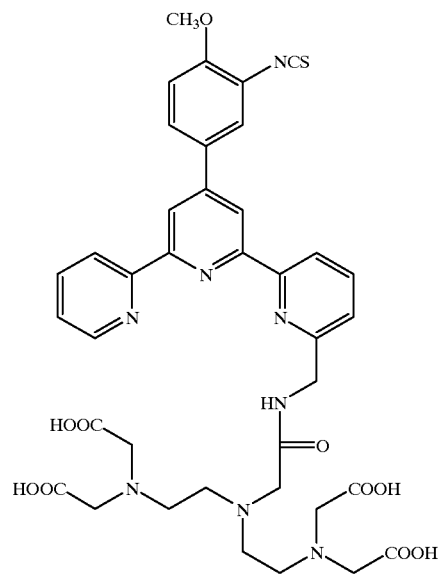
21
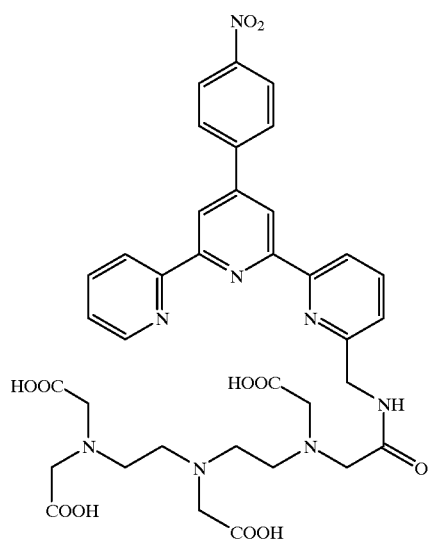
18c
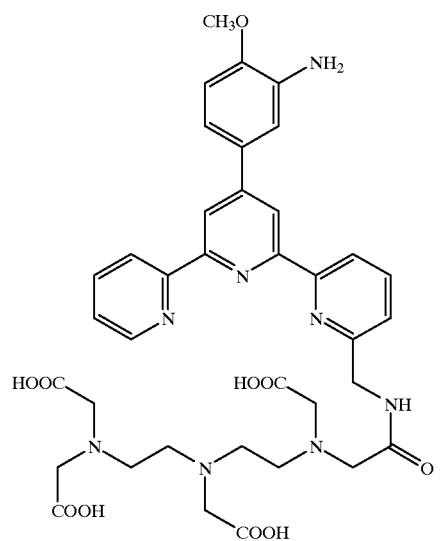
20

-continued
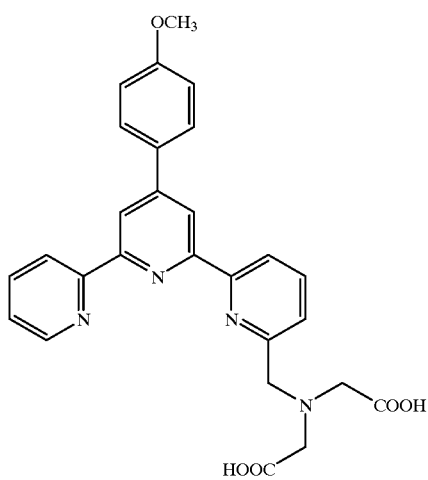
29a
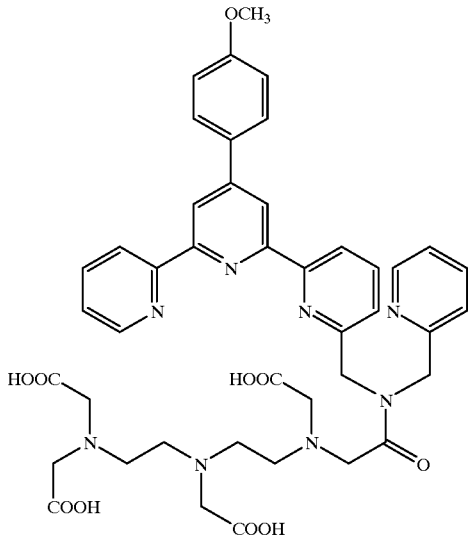
28
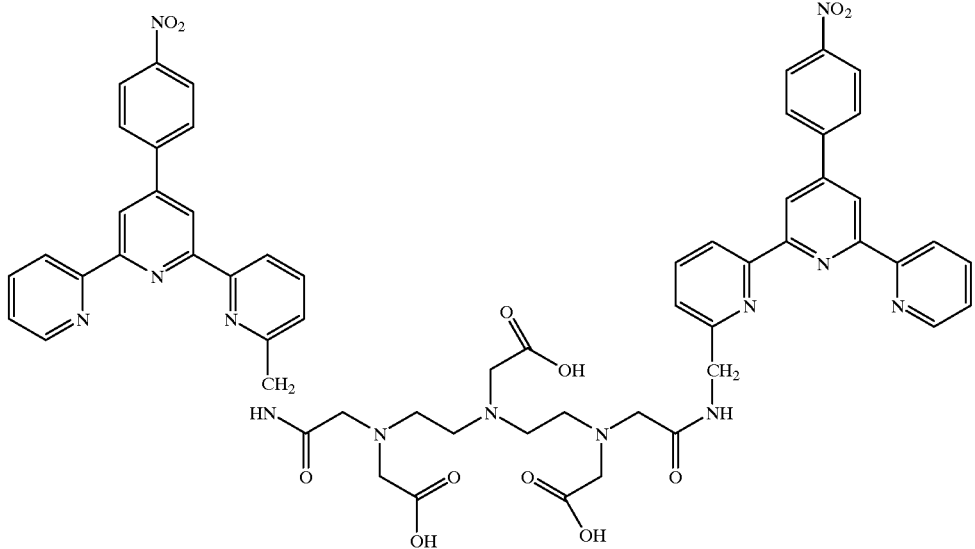
19c

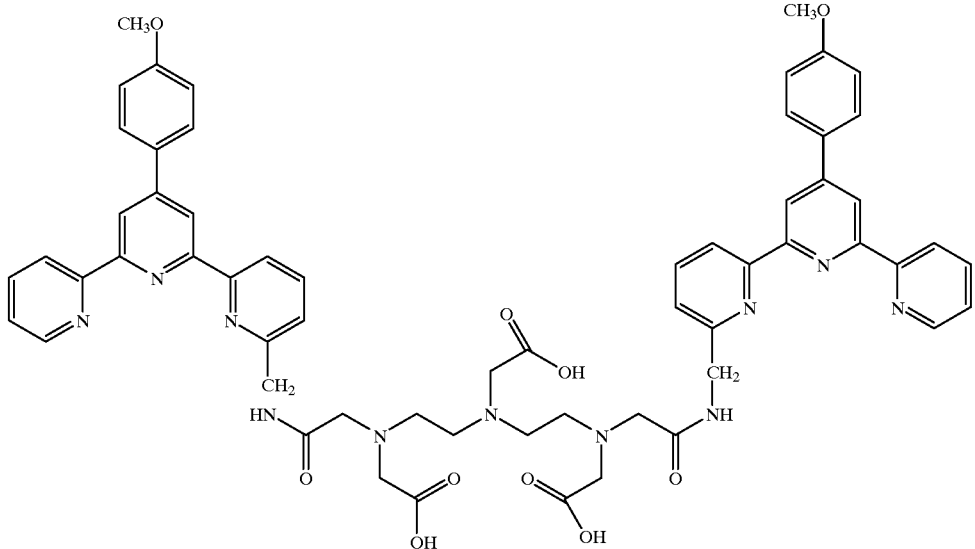
19a
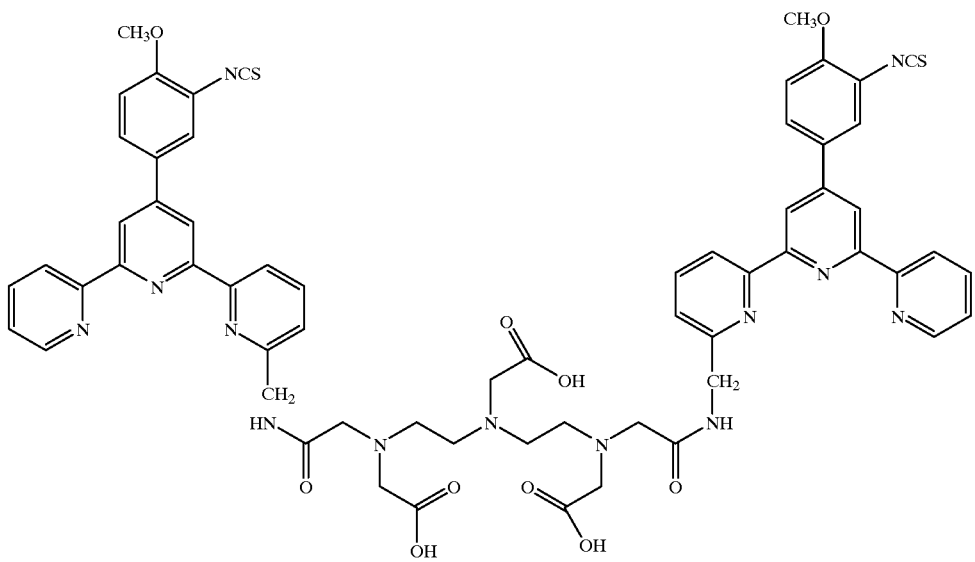
22

-continued

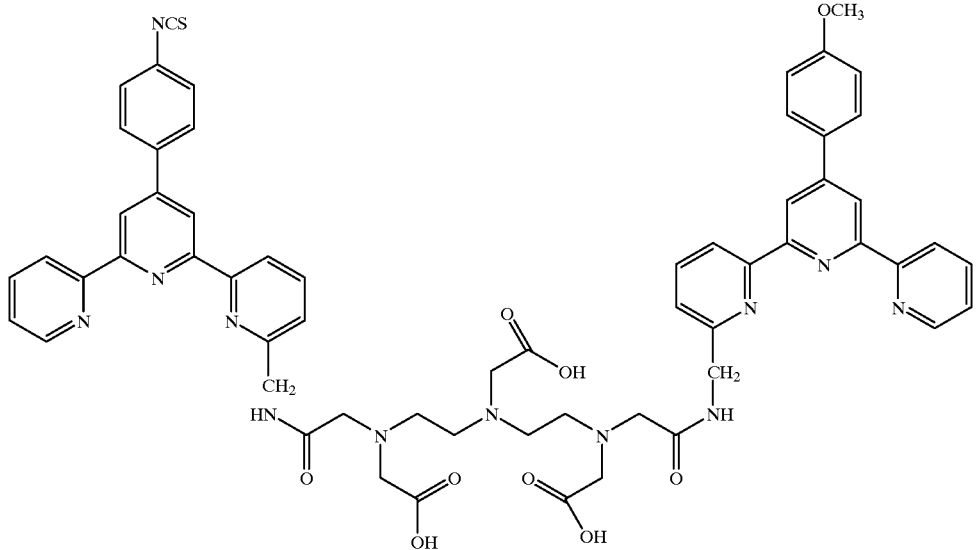

The unsymmetrical oligo-2,6-pyridine complexing agents of this invention can have multiple metal complexing sites, e.g., oligo-2,6-pyridine sites and additional heteroatom sites on Q in structure I. Suitably substituted oligo-2,6-pyridine moieties can be prepared by techniques known in the art, as for example reviewed by Krohnke in Synthesis, 1 (1976), and used as intermediates in the synthesis of the 6-substituted oligo-2,6-pyridine complexing agents of this invention. Suitable reaction schemes are illustrated in U.S. Pat. Nos. 4,837,169 and 4,859,777, the disclosures of which are hereby incorporated herein by reference. A large number of pyridines substituted at the 2- and 6-positions such as, for example, 2,6-dibromopyridine and 2,6-dimethylpyridine as well as at the 4- and 3-, and/or 5-positions such as, for example, 2,4,6-collidine, 2-bromo-5-nitropyridine, and 2,3-lutidine are available commercially, for example, from Aldrich Chemical Company, or can be made according to well known methods illustrated, for example, by R. L. Framk and E. F. Reiner in J. Chem. Soc. (1950), vol 72, pp 4182–3, and can be used as intermediates in the synthesis of the unsymmetrical oligo-2,6-pyridine complexing agents of this invention.

The preparation of representative synthetic intermediates (compounds 2 through 16) which are useful in the preparation of a wide variety of compounds of this invention as well as the preparation of certain currently preferred compounds of this invention (compounds 17 through 23 as well as 26, 27, 28, 29, 31, and 32) are illustrated in the following reaction schemes.

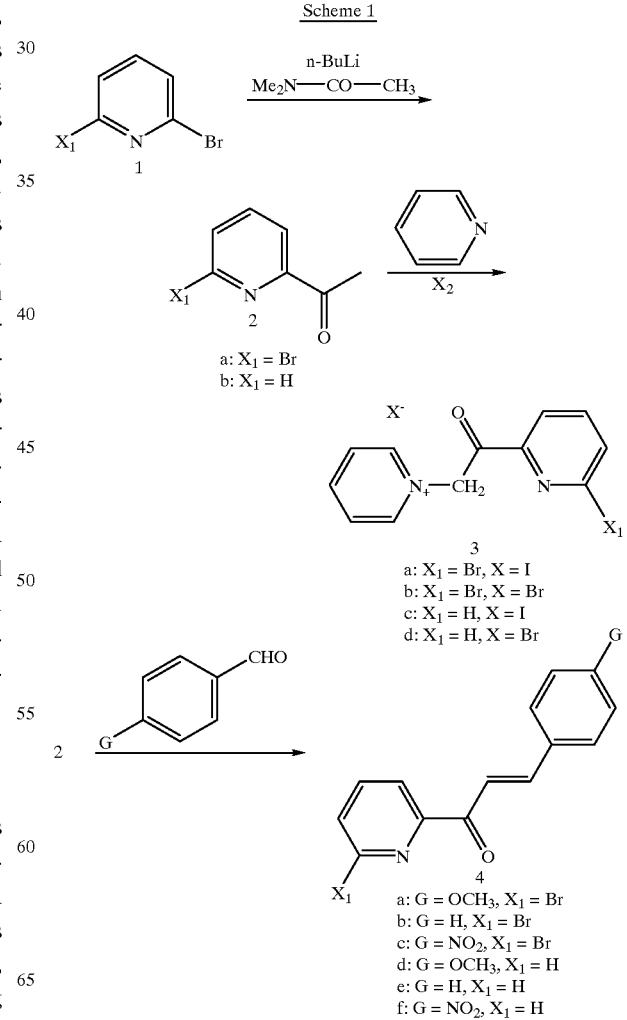

Scheme 1

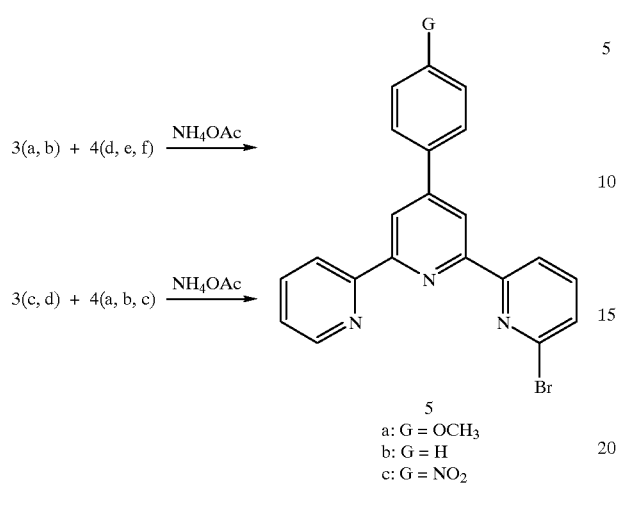
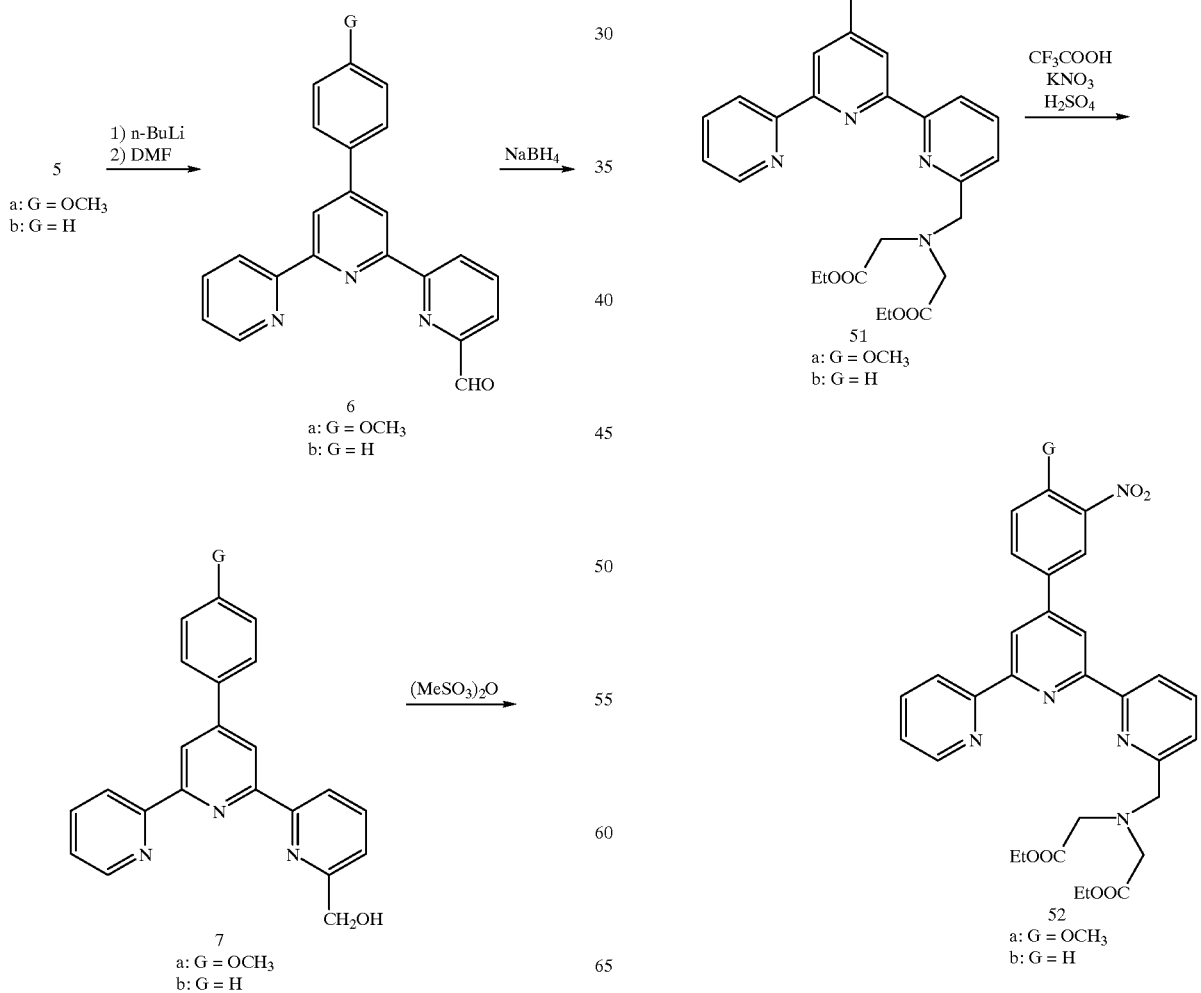

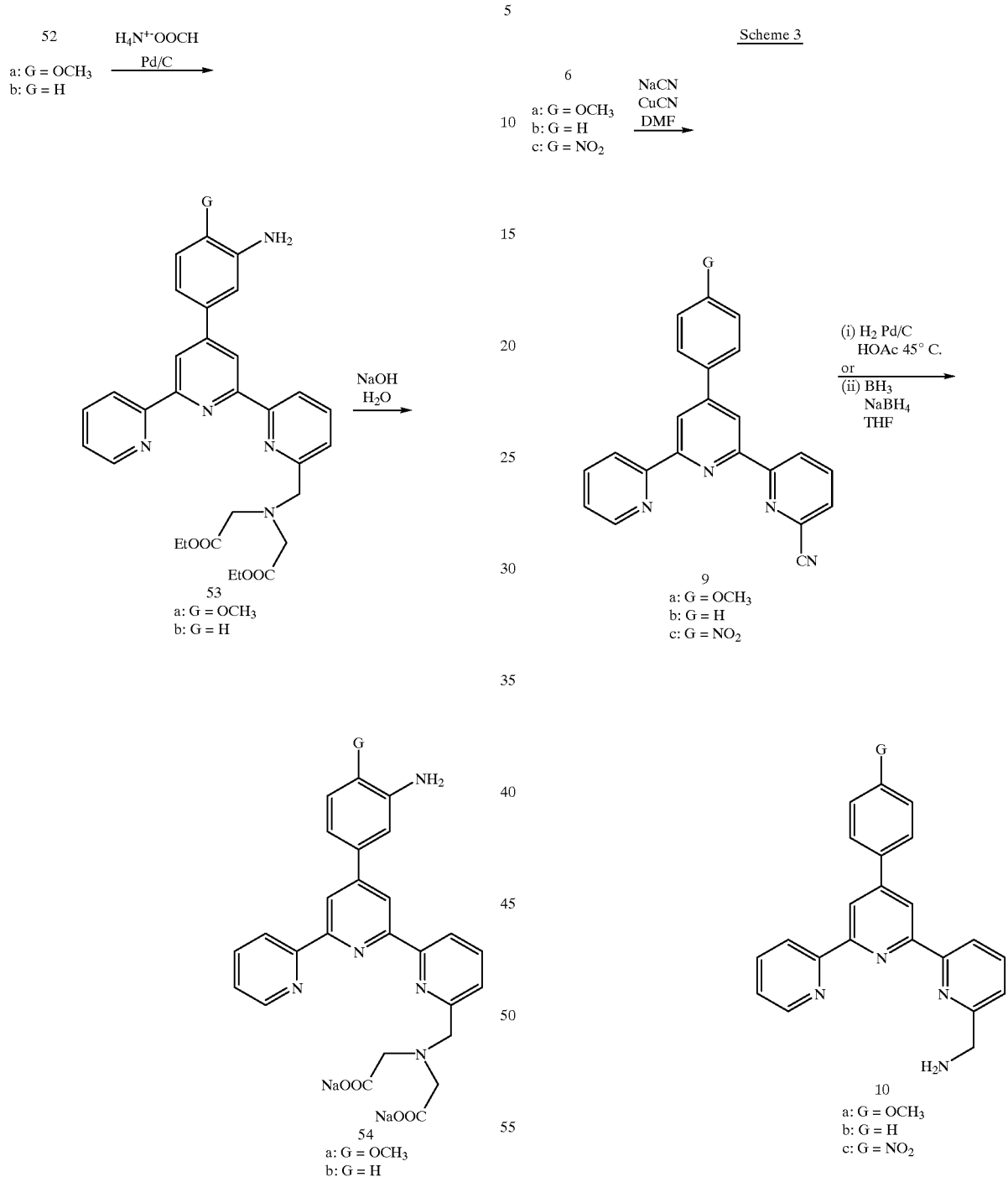

Scheme 4
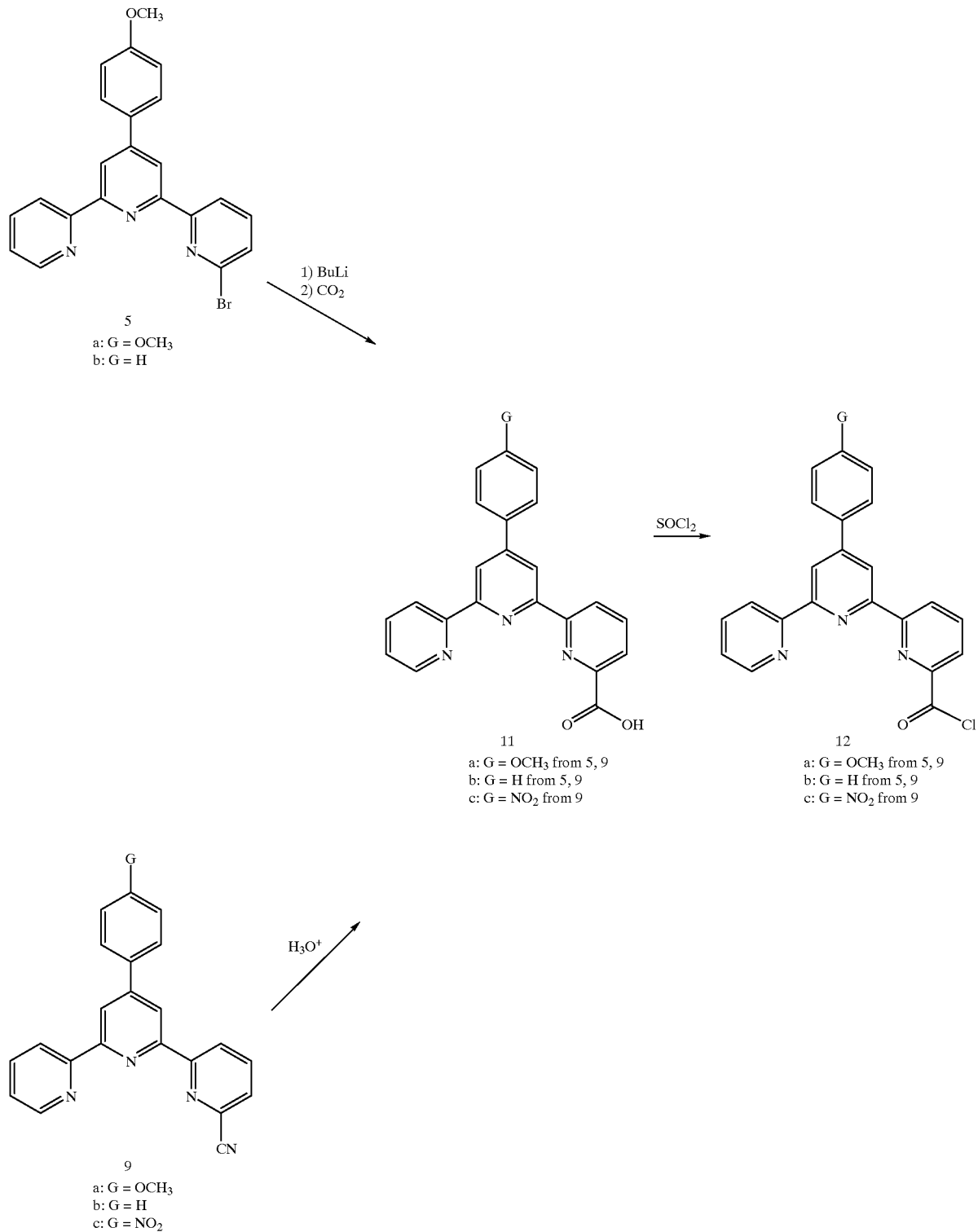

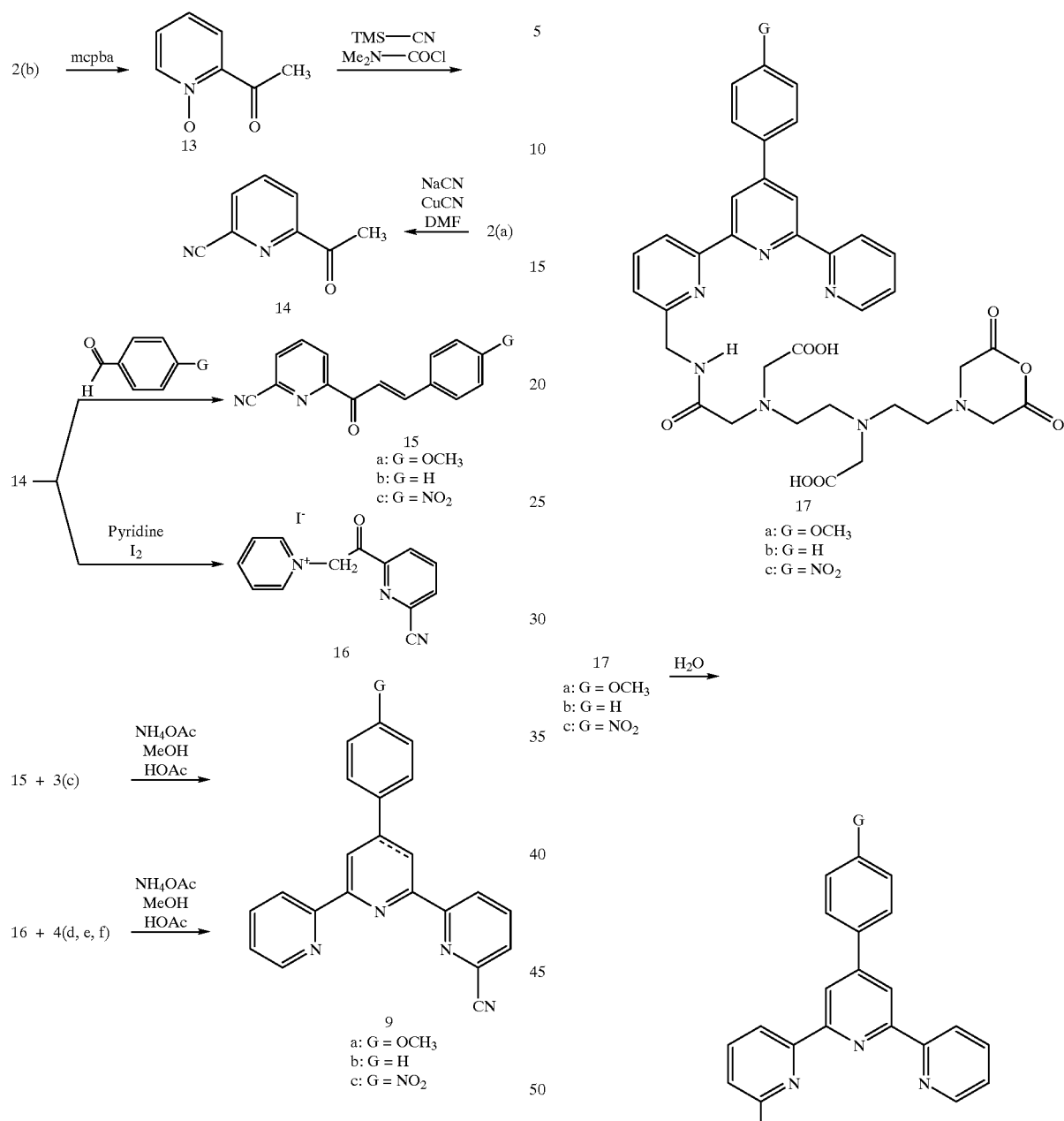
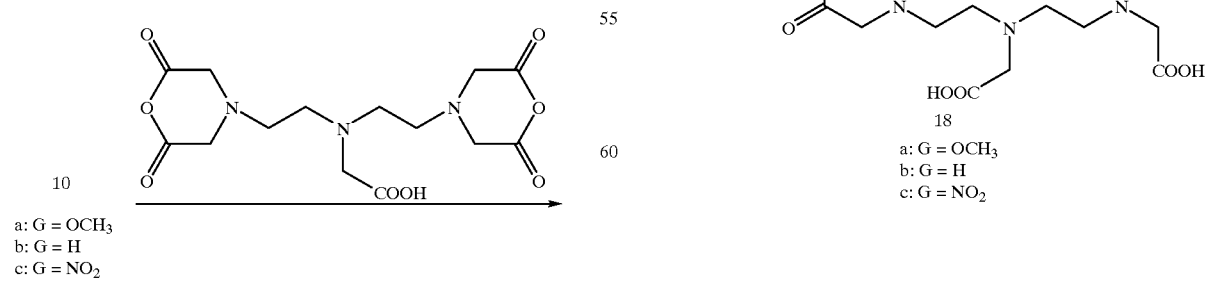

Scheme 7
17
a: G = OCH₃
b: G = H
c: G = NO₂
10
a: G = OCH₃
b: G = H
c: G = NO₂
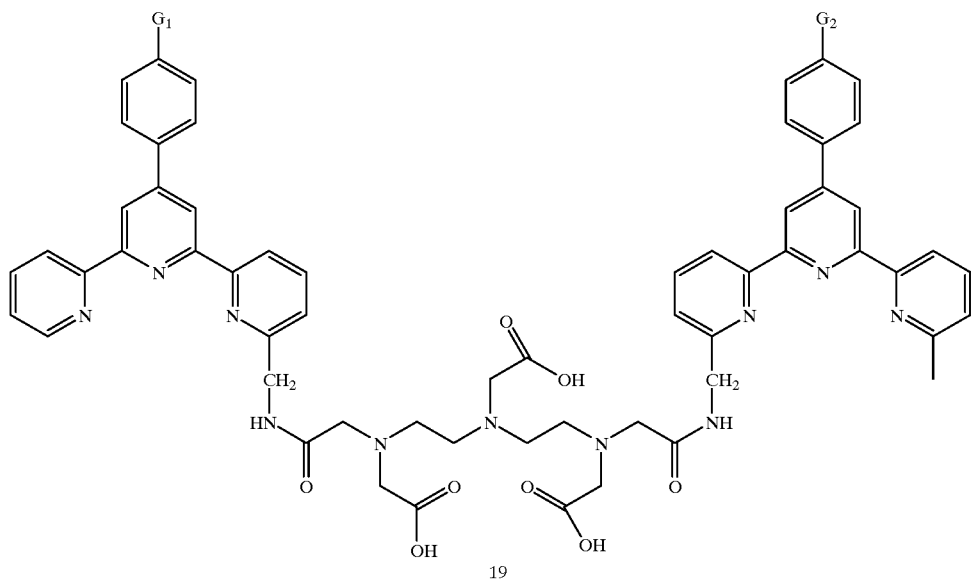
19
a: G₁ = OCH₃, G₂ = OCH₃
b: G₁ = H, G₂ = H
c: G₁ = NO₂, G₂ = NO₂
d: G₁ = OCH₃, G₂ = H
e: G₁ = OCH₃, G₂ = NO₂
g: G₁ = NO₂, G₂ = H

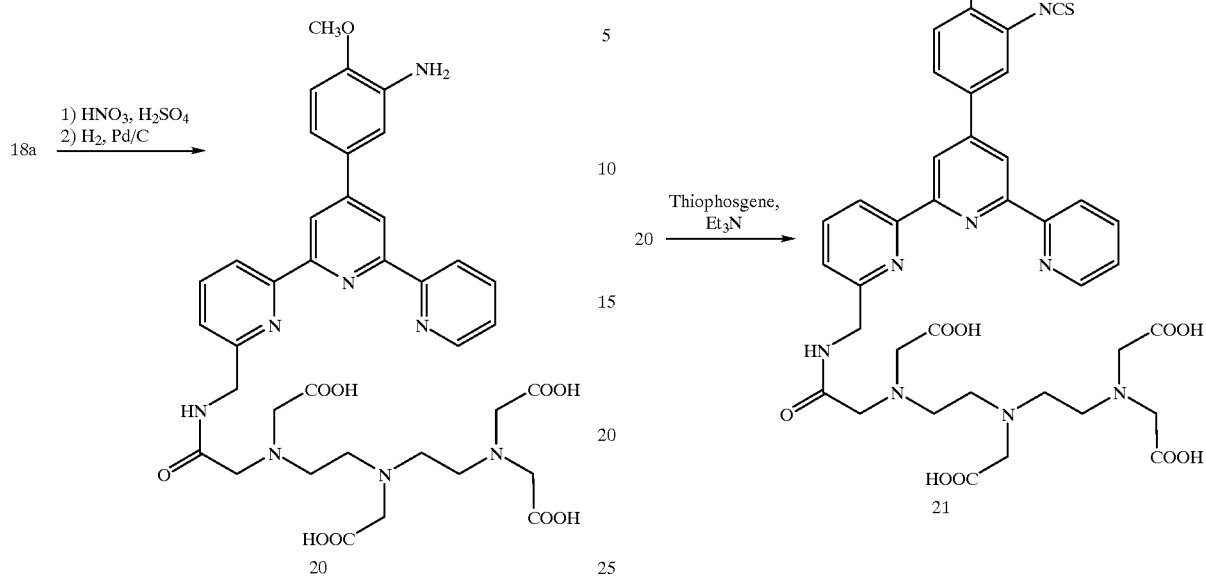
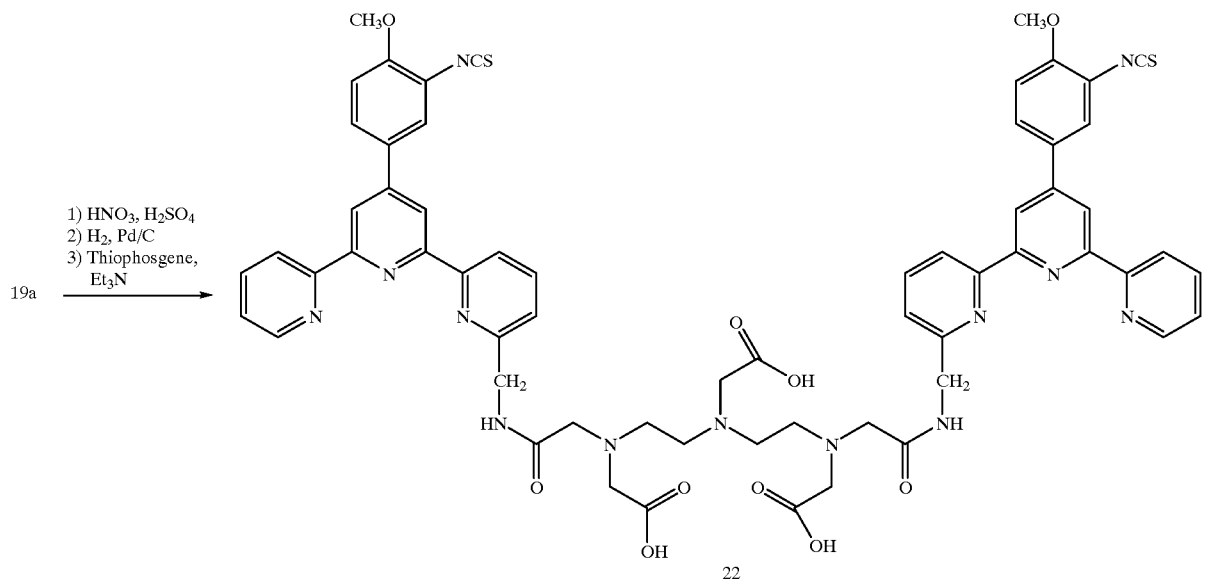

-continued
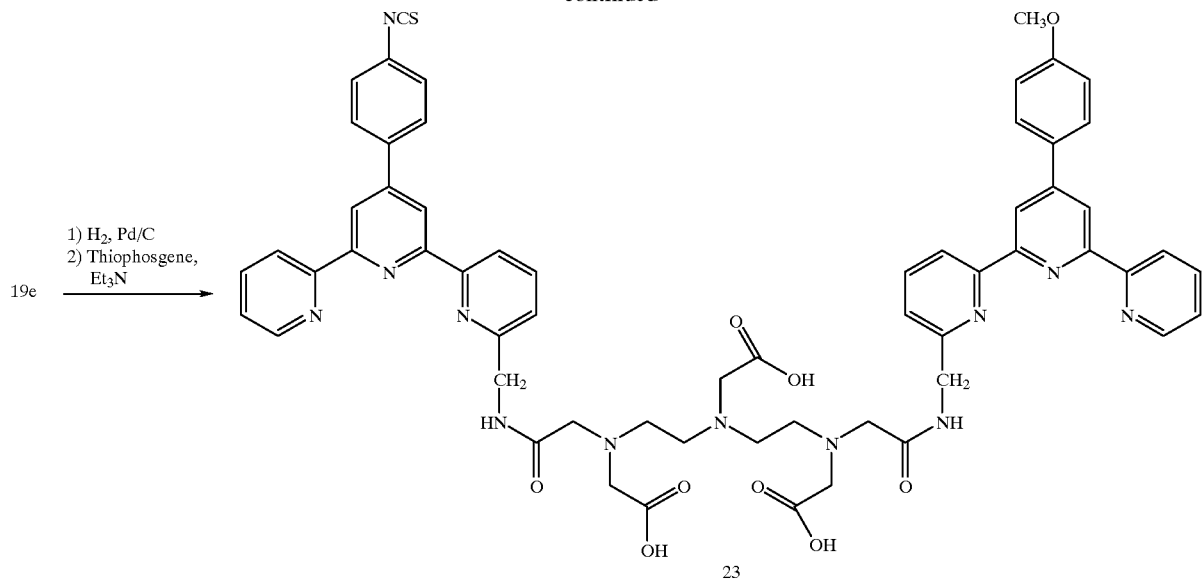
Scheme 10
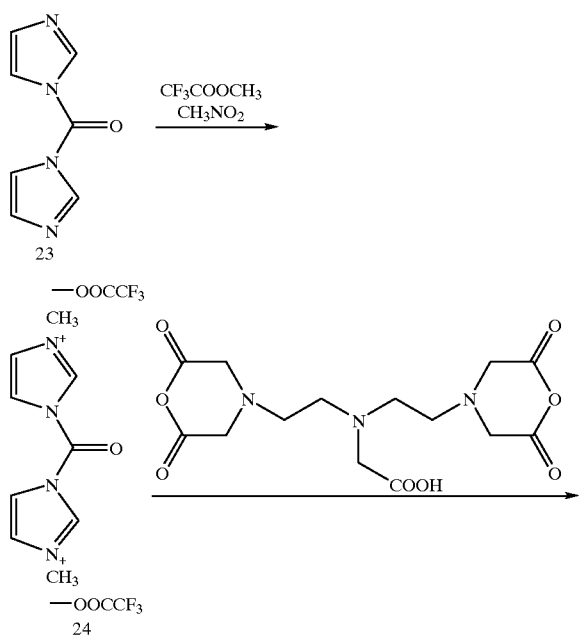

-continued
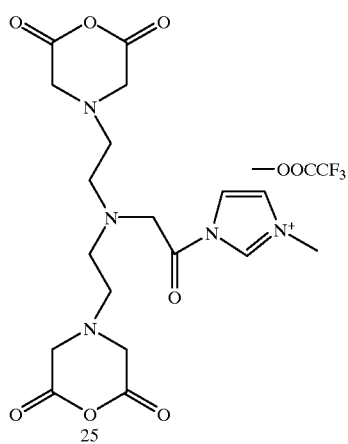
25
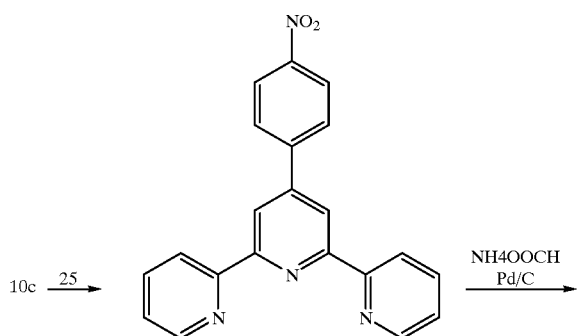
26
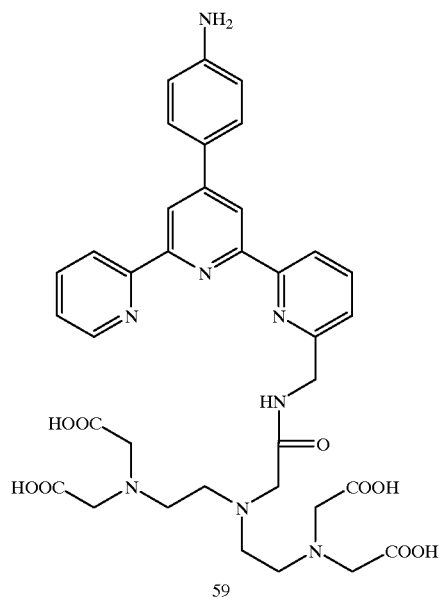
59

-continued
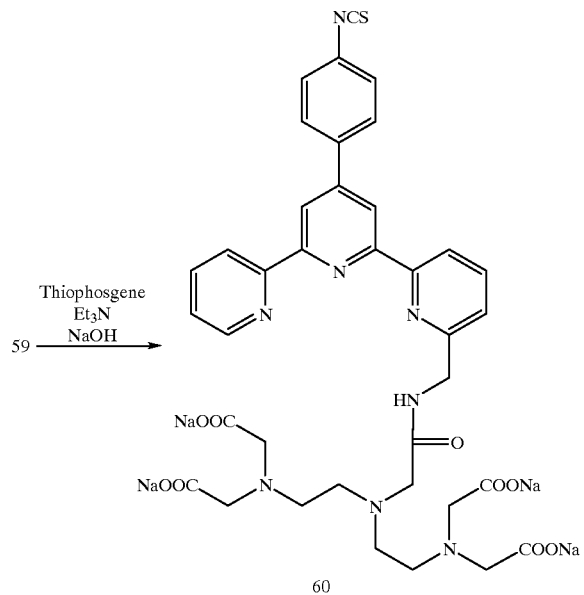
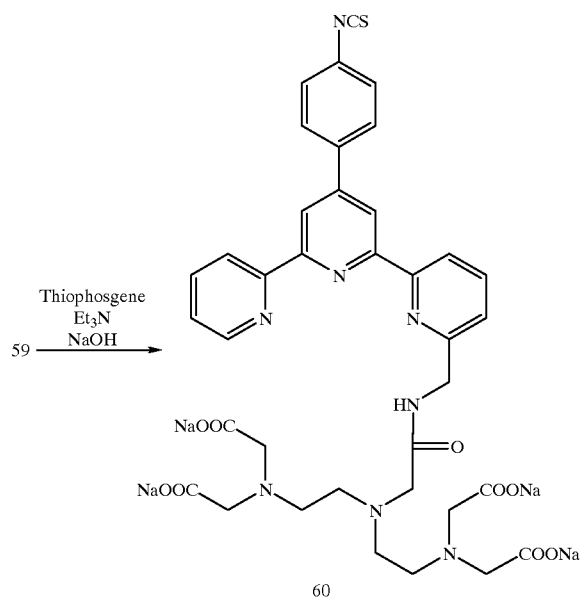

Scheme 11
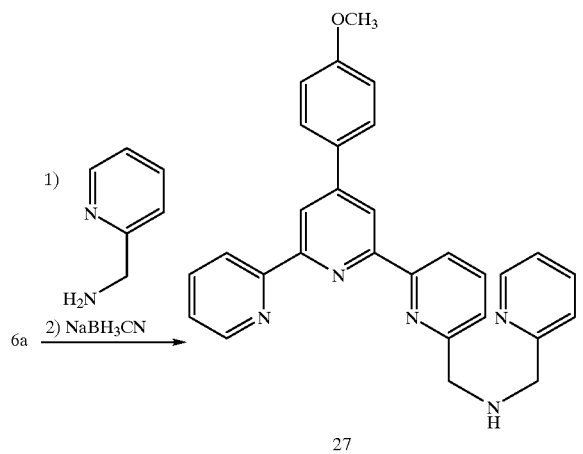
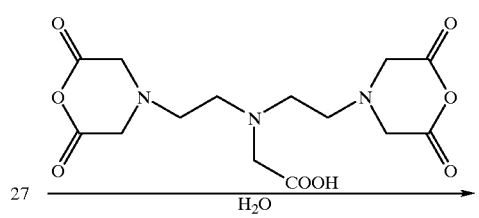
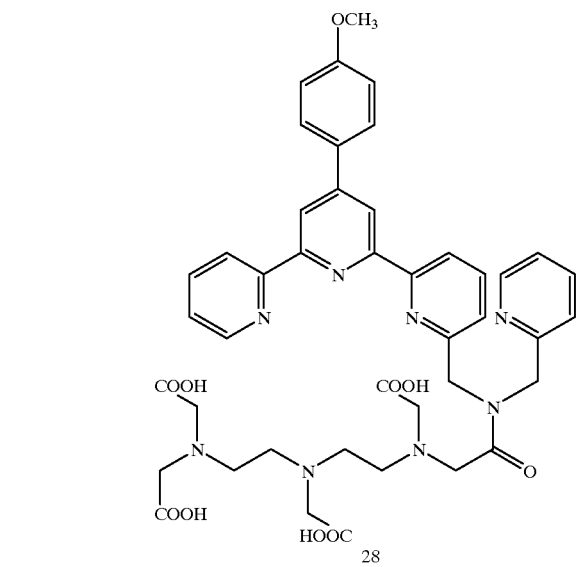
Scheme 12
10
a: G = OCH₃
b: G = H
c: G = NO₂
1) BrCH₂COO-t-Bu
   i-Pr₂NEt
2) CF₃COOH
   H₂O
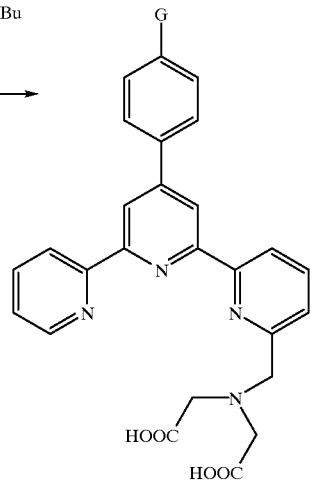
29
a: G = OCH₃
b: G = H
c: G = NO₂
Scheme 13
12
a: G = OCH₃
b: G = H
c: G = NO₂
CH₃OH
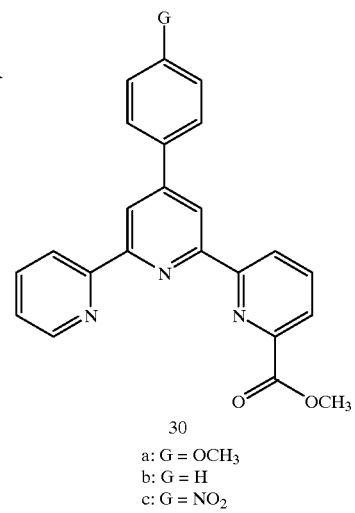
30
a: G = OCH₃
b: G = H
c: G = NO₂

-continued
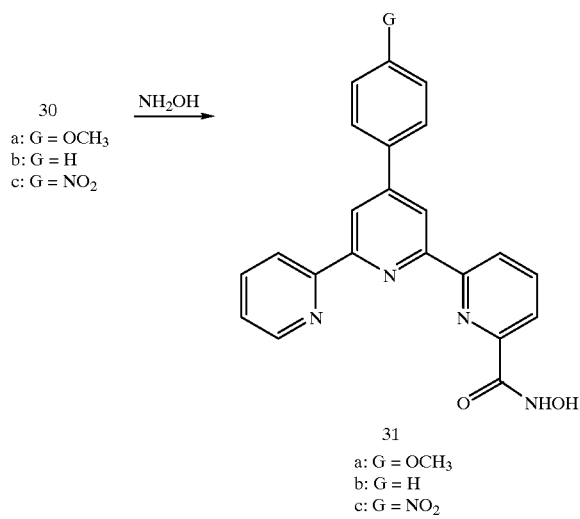
Scheme 14
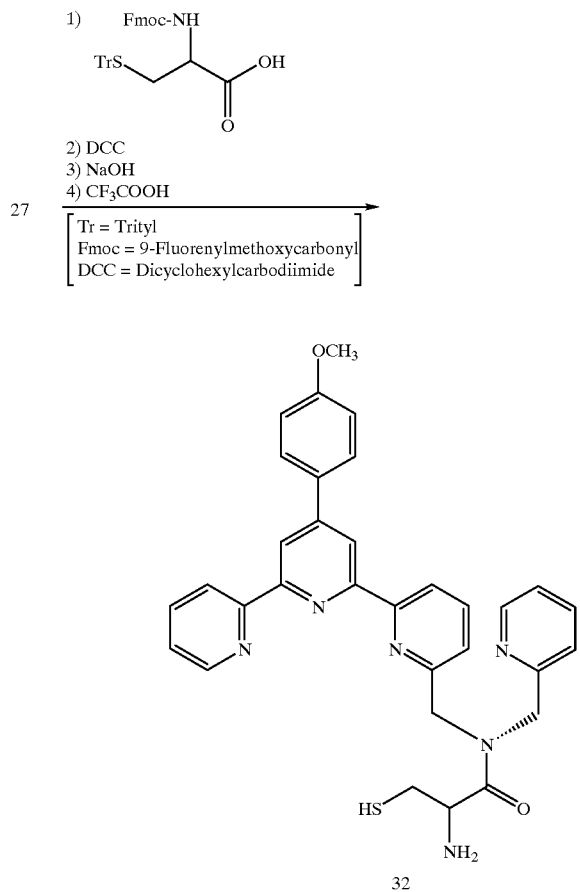
Scheme 15
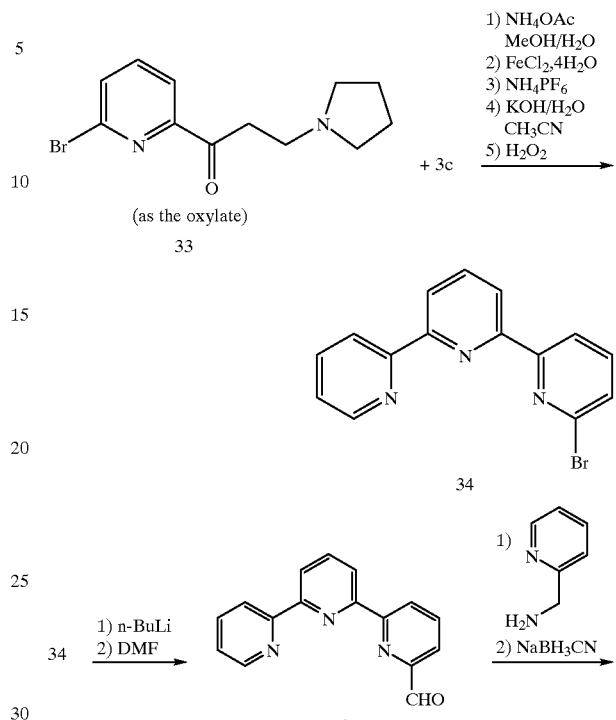
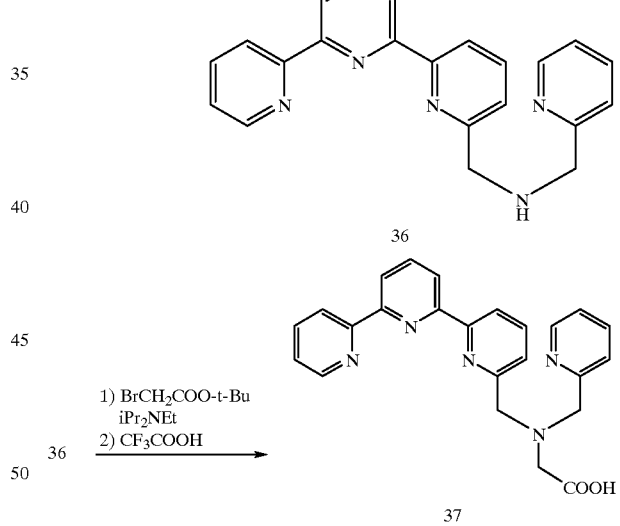
Scheme 16
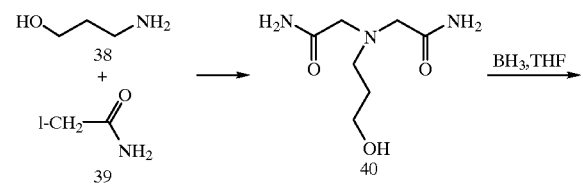

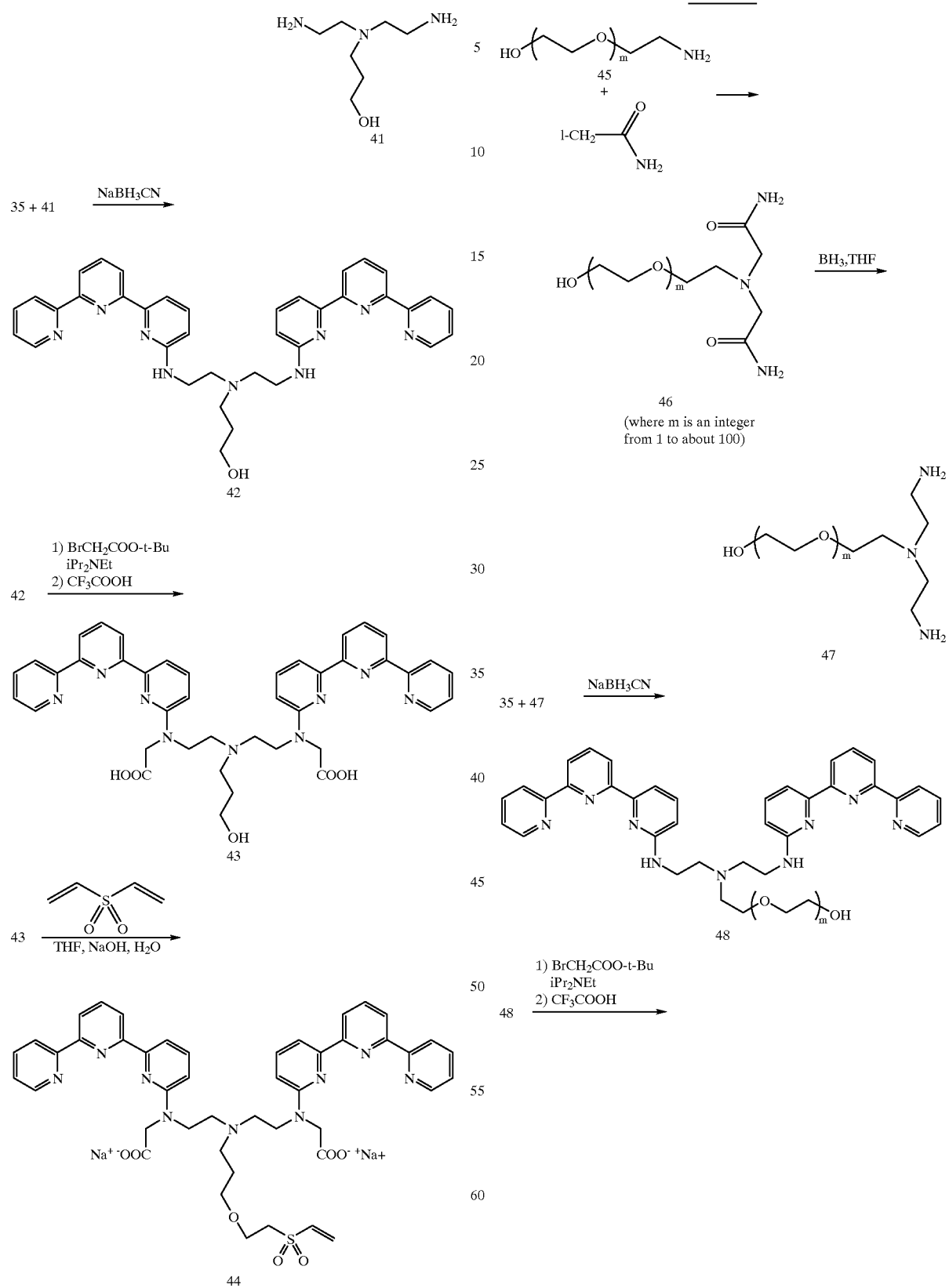

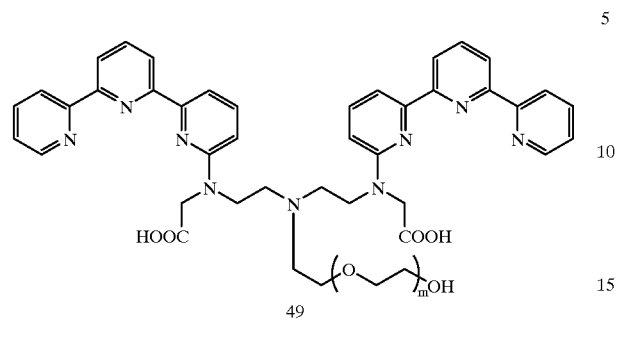
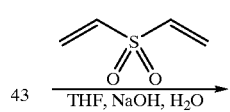
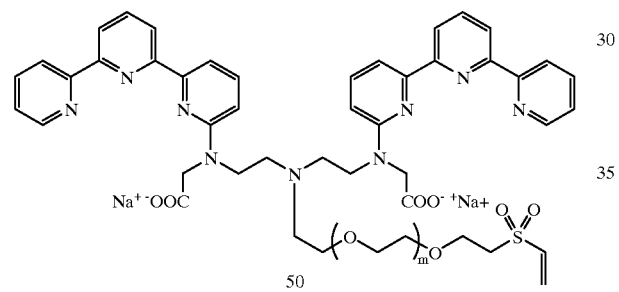
Scheme 18
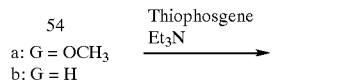
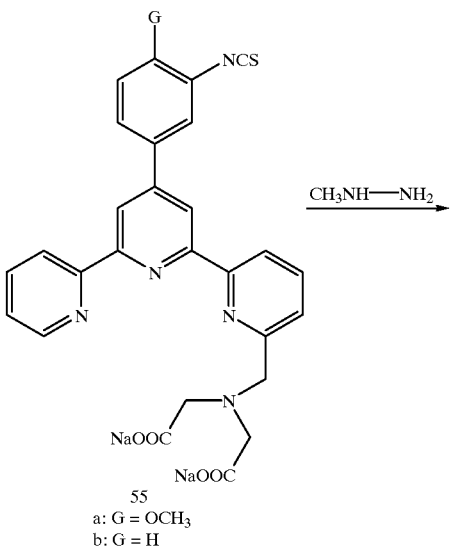

Scheme 19

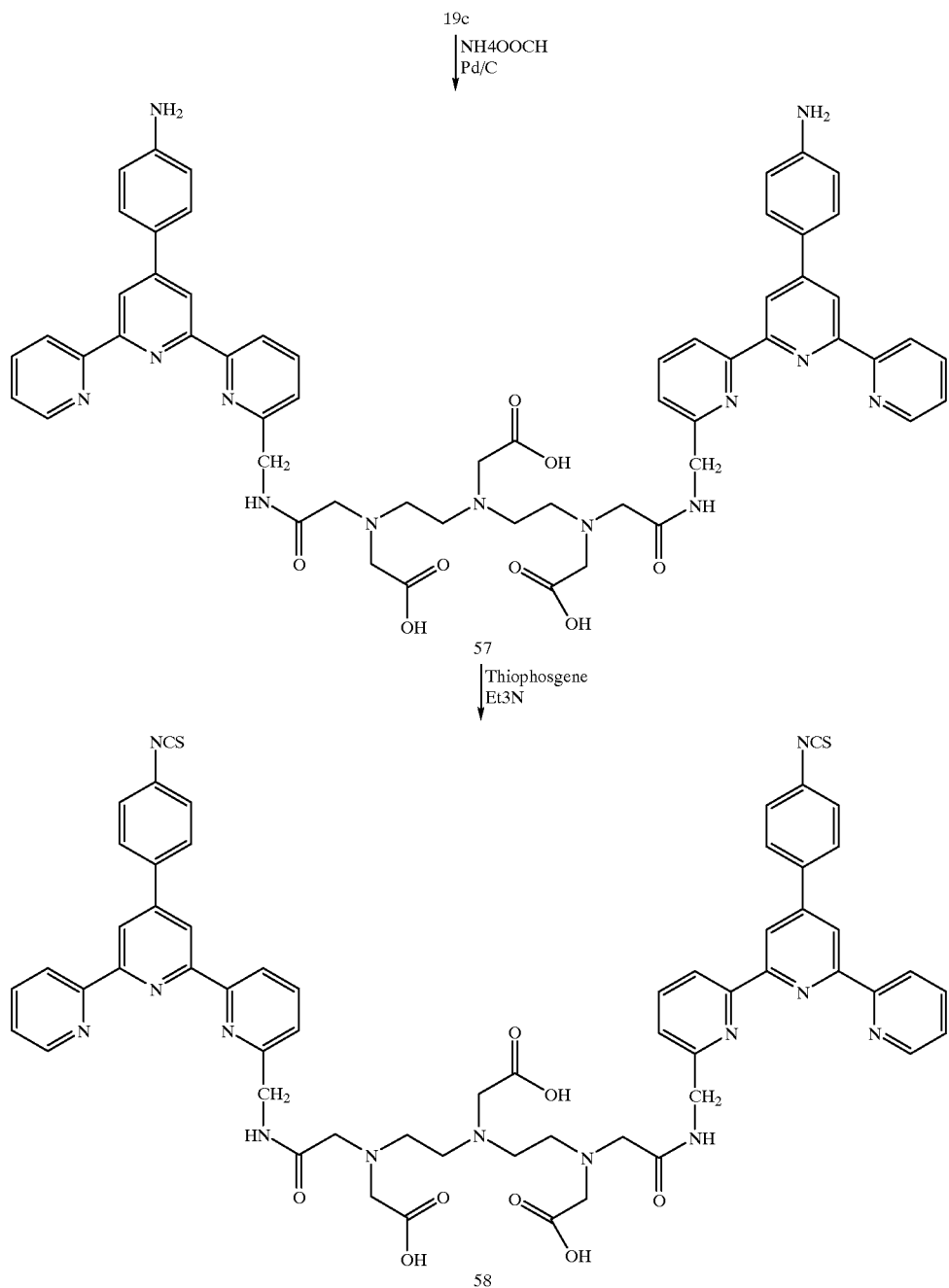

The introduction into the complexing agents of this invention of one or more protein reactive groups described above can be accomplished by conventional chemical reactions. For example, amine groups can be added to aryl groups such as phenyl groups on phenyl-substituted oligo-2,6-pyridines by nitration followed by reduction of the nitro groups to amines. Substituents which comprise phenyl groups, alkyl phenyl groups and alkoxyphenyl groups as described above at R or $R_1$ as well as such groups when they comprise a substituent of Q in Structure I are especially suited to this reaction. Such groups can be converted by nitration employing, for example, nitric acid and sulfuric acid to produce a nitro-substituted phenyl group which can be reduced to an aminophenyl group as in compound 20.

As is well known, use of heat and increased amounts of nitrating reagent can lead to increased amounts of nitration of an aromatic ring. Use of such conditions in the presence of phenyl groups, alkyl phenyl groups and alkoxyphenyl groups on phenyl-substituted oligo-2,6-pyridines can lead to the production of dinitro-substituted phenyl groups on phenyl-substituted oligo-2,6-pyridines which can be reduced to provide diaminophenyl groups on phenyl-substituted oligo-2,6-pyridines.

If desired, the amine groups can be readily converted to isocyanate groups by reaction with phosgene to produce the carbamoyl chloride which, upon heating, releases HCl to produce the isocyanate.

Isothiocyanate groups can be introduced by treatment of the amine groups with thiophosgene to produce the thiocarbamoyl chloride which, upon treatment with a base such as a tertiary amine base, releases HCl to produce the isothiocyanate as in compound 21.

In the absence of other carboxylic acid groups, activated carboxy groups can be added by treatment of amine-containing oligo-2,6-pyridines such as compound 27 with agents such as glutaric anhydride to form an amide linkage to the substituent on the oligo-2,6-pyridine and an free carboxyl group from the anhydride. This can be followed by suitable selective activation of the carboxyl functionality to form, for example, an oligo-2,6-pyridine attached via an amide group to an activated ester by treatment with N-hydroxysuccinimide or with 4-nitrophenol, each under dehydrative coupling conditions, for example, employing a carbodiimide reagent such as dicyclohexylcarbodiimide.

Cyclic acetal protected aldehydes can be carried through that part of a reaction sequence necessary to synthesize an unsymmetrical ketal protected aldehyde linked to a 6-substituted-oligo-2,6-pyridine chelator. The cyclic acetal can and then be deprotected, for example, by acidic hydrolysis before for use in a protein conjugation reaction.

Alternatively, a functional group such as an alkyl group containing a hydroxyl group can be introduced into a substituent comprising one or more of R, $R_1$, or Q in Structure I as described above. For example, a 3-hydroxypropyl group can be introduced as a substituent of Q with a reagent such as N-(3-hydroxypropyl)-N,N-bis(2-aminoethyl)amine as illustrated in Scheme 16. In this representative case where R and $R_1$ are each hydrogen, reductive amination of the triamine with an oligo-2,6-pyridine which contains an aldehyde group at the 6-position of the oligo-2,6-pyridine (i.e., at the 6-position of a terpyridine, at the 6-position of a quaterpyridine ring, etc.) can be accomplished using sodium cyanoborohydride or with hydrogen and a catalyst such as palladium on carbon. Optionally, the reductive amination can be done in the presence of a template metal ion such as a nickel ion or lead ion or a cesium ion, followed by removal of the metal template ion such as by using excess cyanide ion. Alkylation of the thus formed secondary amines with reagents such as bromoacetic acid or a bromoacetic acid ester (e.g., t-butyl, methyl, ethyl etc. esters are useful) provides a carboxymethyl amine with a 3-hydroxypropyl group as a substituent. The hydroxyl of the 3-hydroxypropyl group can then be converted, for example, into a sulfonic acid ester (e.g., with methanesulfonic acid anhydride in pyridine or with an arylsulfonic acid anhydride such as benzenesulfonic acid anhydride or with methanesulfonic acid anhydride in pyridine), or it can be converted into a chloro group by the reaction of thionyl chloride. The thus formed sulfonatopropyl group or chloropropyl group can be reacted with sodium azide to form an azidopropyl group. The thus formed azido compound can be reduced to an amino group using hydrogen and palladium on carbon.

The 3-hydroxypropyl group thus can be converted into a 3-aminopropyl group. This amino group can react under reductive amination conditions (e.g., in the presence of sodium cyanoborohydride, preferably at a pH of about 5 to about 6) with an aldehyde functional group substituent on an immunoreactive group. Said aldehyde group can be introduced prior to reaction with the amine group described above, for example, by oxidation with sodium periodate of a carbohydrate portion of an immunoreactive group such as an antibody.

In addition, amine groups introduced into groups R, $R_1$ and Q introduced as described above can be further modified using, for example, commercially available heterobifunctional crosslinking reagents as described below to introduce sulfhydryl groups (—SH groups) and active olefin groups such as maleimide groups into the substituent of one or more of R, $R_1$ and Q groups of structure I.

In compounds represented by Structure I wherein one or more of R, $R_1$ and Q comprise an unprotected hydroxyl group as described above, preferably as a primary hydroxyalkyl group, a sulfhydryl group can be introduced at each such hydroxyl group, for example, by conversion of each hydroxyl group substituent into a halo group such as a chloro group using thionyl chloride or into a sulfonate using, for example, methanesulfonic acid anhydride or an aryl sulfonyl chloride. Both the chloro- and the sulfonato-groups thus formed can then be reacted with thiourea and the resulting thiouronium salt can be reacted with base to each produce a sulfhydryl group. Alternatively, an amine group as described above can be reacted with N-acetyl homocyteine to form an amide bond and simultaneously introduce a sulfhydryl group linked thereto (i.e., to form a —NH—CO—CH2CH2-SH substituent).

The unsymmetrical oligo-2,6-pyridine chelating agents of this invention can contain zero, one, two or more than two protein reactive groups. However, in one preferred aspect of the invention, the unsymmetrical oligo-2,6-pyridine chelating agents of this invention contain no more than two protein reactive groups. In another preferred aspect, the unsymmetrical oligo-2,6-pyridine chelating agents of this invention contain no more than one protein reactive group.

The class of 6-substituted oligo-2,6-pyridines conforming to Structure I above wherein R is hydrogen, and $R_1$ is a phenyl group containing an alkyl or alkoxy group (i.e., as represented by Structure III) is particularly advantageous from a synthetic standpoint. For example, the presence of an alkyl or alkoxy group on a brominated intermediate such as (5) provides enhanced solubility in THF, which is a preferred solvent for use in the preparation of the intermediate aldehyde (6). The presence of an alkyl or alkoxy group also provides an enhanced reactivity and an ortho directing effect for the introduction by nitration as described above of a nitro group, and, hence, for the introduction of an amino and subsequently of an isothiocyanato group. This is demonstrated in the preparation of chelating agents (20), (21) and (22). In addition, other groups can be derived from these amine and isothiocyanato groups by conventional chemical techniques. For example, a thiosemicarbazide (—NH—C(=S)—NR$^3$—NH$_2$) group can be obtained by the reaction of an isothiocyanate (—N=C=S) group with a hydrazine such as HNR$^3$—NH$_2$ where R$^3$ is hydrogen, or a methyl or other alkyl group as described above. A phenyldiazonium (—N$_2^+$) salt group can be introduced by the reaction of an phenylamino group with nitrous acid. Said diazonium group can be converted into a wide variety of useful functional groups including a phenol hydroxyl group.

Several other synthetic routes can be applied to generate derivatives of compounds of this invention which contain protein reactive groups connected to one or more of R, R1, or Q. For example, a compound containing a hydroxyalkyl group such as (43) can be treated with divinyl sulfone to form the monoaddition compound (48) that provides a vinyl sulfone protein reactive group (Scheme 16). Alternatively, the reaction outlined in Scheme 17 to generate (50) from (49) can be employed, for example, using the poly(ethylene glycol) analog (47) in place of (41) to generate, after subsequent reaction with t-butyl bromoacetate, of the corresponding bis(acetic acid) derivative, (49), from (35). (49) can then be treated with divinyl sulfone to form the vinyl sulfone (50). The reaction with divinyl sulfone is preferably base catalyzed. In componds (47) through (40), m is an integer in the range from 1 to about 100.

A hydroxyl group such as that in a substituent comprising a hydroxyalkyl or hydroxyalkylene group at R, $R_1$ or Q of a chelating agent of this invention can be treated with an aryl chloroformate such as p-nitrophenyl chloroformate or 2,4, 5-trichlorophenyl chloroformate to produce the corresponding aryl carbonate group as a protein reactive group from that hydroxy group. Said aryl carbonate can react with primary and secondary amine groups. Examples of primary amine groups include lysine epsilon amine groups and amine terminal groups found in amino acids, peptides and proteins.

The incorporation of amine-reactive protein reactive groups into the unsymmetrical oligo-2,6-pyridine chelating agents of this invention preferably requires that chemical functionalities such as primary and secondary amine groups which are capable of reacting with the protein reactive group be not present elsewhere in the structure of the chelating agent. However, in one embodiment of the unsymmetrical oligo-2,6-pyridine chelating agents of this invention, the simultaneous presence of such chemical functionalities and protein reactive groups is desireable. In such cases, oligomeric and polymeric materials can be produced by the reaction of the chemical functionalities with the protein reactive groups.

Alternatively, an alcohol group as described above a substituent of a chelating agent of this invention comprising a hydroxyalkyl substituent at R, $R_1$ or Q can be reacted directly with cyanuric chloride to produce a 4,6-dichlorocyanurate [i.e., a 2-(4,6-dichloro)-1,3,5-triazinyll group. This dichlorocyanurate can react with amine groups such as amine groups on amino acids, peptides, and proteins as described above.

Alternatively, the sodium salt of an alcohol group on a substituent of a chelating agent of this invention comprising a hydroxyalkyl substituent at R, $R_1$ or Q can be elaborated into an aldehyde group by treatment with, for example, 2-bromomethyl-1,3-dioxolane which produces a cyclic acetal of a formylmethyloxyalkyl substituent from the hydroxyalkyl substituent. The aldehyde can be liberated from the cyclic acetal by deprotection with aqueous acid. This aldehyde is suitable for use in reductive amination procedures (e.g., those incorporating the use of sodium cyanoborohydride as the reducing agent at a pH in the range of 4 to 7, preferably about pH 6, in an aqueous system) for the linking of the aldehyde to an amine on a protein.

Alternatively, an alcohol group as described above of a chelating agent of this invention comprising a hydroxyalkyl substituent at R, $R_1$ or Q can be converted to a sulfonate ester using, for example, methanesulfonic anhydride in pyridine, and the sulfonate ester can be then converted to an amine, for example, by treatment with sodium azide followed by reduction with triphenylphosphine or hydrogen in the presence of a catalyst such as palladium on carbon.

Unsymmetrical oligo-2,6-pyridine chelating agents of this invention which contain a methoxyphenyl group can be demethylated using HI and red phosphorous to provide the corresponding phenol in place of the methoxy group. Said phenol can be cyanoethylated with acrylonitrile to form a cyanoethyloxyphenyl group. The nitrile can be treated with ah alcohol such as ethanol in the presence of anhydrous HCl to provide an amidate such as an ethyl amidate.

Alternatively, the phenol as described above can be alkylated as the sodium phenolate salt (produced from the phenol by the action of sodium hydride or sodium hydroxide) with an alpha-cyano-omega-haloalkane to produce an omega-cyanoalkyloxyphenyl group. This can be treated with alcoholic HCl to provide an omega-amidatoalkyloxyphenyl group.

Alternatively, the phenol as described above can be alkylated with an alpha haloacetate ester such as methyl bromoacetate to produce a methyl ester of the corresponding carboxymethyloxyphenyl group. This ester can be treated with hydrazine to provide a hydrazide which is capable of reacting with aldehyde functionality such as, for example, that introduced by oxidation of a carbohydrate moiety attached to an antibody.

Alternatively, the hydrazide as described above can be treated with an aqueous acid such as HCl and then with sodium nitrite to provide the carbonyl azide. This can be reacted with amines on proteins at pH's above seven to provide amide linked chelates.

Alternatively, the phenol as described above can alkylated with a terminal hydroxyalkyl halide wherein the alkyl group is as described above to produce a hydroxyalkylene group. The aliphatic alcohol group can be treated with an aryl chloroformate such as p-nitrophenyl chloroformate or 2,4, 5-trichlorophenyl chloroformate to produce a carbonate as described above. This arylchloroformate can react with amine groups or proteins such as amines in lysines and at peptide amine termini.

Alternatively, a phenol as described above can be reacted directly with cyanuric chloride to produce a cyanurate, or an alcohol, derived from the phenol by alkylation with, for example, a hydroxyalkyl chloride which contains an alkylene spacer linkage as described above can be so treated to produce a dichlorocyanurate as described above. These chlorocyanurates can react with amine groups on proteins.

Alternatively, a phenol as described above can be converted to a formylethyleneoxyphenyl group [i.e., a H—C (=O)—$CH_2CH_2$—O-phenyl group] by treatment with acrolein via addition of the phenol-OH group to the double bond of the acrolein. Additionally, a phenol as described above can be converted into a formylalkyleneoxyphenyl group first by alkylation of the phenol as a sodium phenolate prepared as described above with a haloalkylene dialkyl acetal wherein the alkylene group is as described above and the alkyl groups of the acetal aldehyde protecting group contain from one to ten carbon atoms or together form a cyclic ring of from two to four carbon atoms. The acetal can then be hydrolyzed by treatment with aqueous acid to liberate the aldehyde group. Aldehyde groups thus formed are suitable for use in reductive amination procedures (e.g., those incorporating the use of sodium cyanoborohydride as the reducing agent at a pH in the range of 4 to 7, preferably about pH 6, in an aqueous system) for the linking of aldehyde to amines on a protein.

Alternatively, a phenol as described above can be converted to an aminopropyleneoxyphenyl group by treatment with acrylonitrile (e.g. in the presence of N-methylimidazole as catalyst) followed by hydrogenation of the nitrile in warm acetic acid solution using hydrogen and 10% palladium on carbon as a catalyst. In addition, a phenol as described above can be converted to an aminoalkyleneoxyphenyl group wherein the alkylene group contains from one to 10 carbon atoms as described above by alkylation with an omega-haloalkyl nitrile followed by hydrogenation of the cyano group in warm acetic acid solution using hydrogen and 10% palladium on carbon as a catalyst.

The above amines can be attached to proteins in several ways. For example, they are suitable for use in reductive amination procedures (e.g., incorporating the use of sodium cyanoborohydride as the reducing agent at a pH of about 6 in an aqueous system) to couple the amine with aldehyde functionality that is generated by the action of an oxidizing agent such as sodium periodate on a carbohydrate moiety attached to a protein (such as an antibody). Aldehyde functionality can also be generated on a protein using reagents such as 4-azo-phenylglyoxal (APG, available from Pierce Chemical Co.) which reacts selectively with arginine residues on the protein.

In addition, the amines described above can be attached to proteins by first being further elaborated with commonly available heterobifunctional reagents (such as are available commercially from Pierce Chemical Company). For example, the amines described herein can be treated with 2-iminothiolane or with N-succinimidyl S-acetylthioacetate (SATA) followed by treatment with hydroxylamine to generate substituents containing free sulfhydryl groups. These latter species which contain free sulfhydryl SH groups which can react with maleimide functionality that can be introduced at amine sites in a protein using reagents such as SMCC [N-(4-carboxycyclohexylmethyl)-maleimide N-hydroxysuccinimidate] and the like.

In addition, the amines prepared as described herein can be treated with SMCC [N-(4-carboxycyclohexylmethyl)-maleimide N-hydroxysuccinimidate] to generate substituents containing active olefin functional groups. These species contain maleimide functionality which can react with free sulfhydryl SH groups that can be introduced at amine sites in a protein using reagents such as 2-iminothiolane or with N-succinimidyl S-acetylthioacetate (SATA) followed by treatment with hydroxylamine. Free sulfhydryl sites can also be generated in a protein by the action of sulfhydryl-containing reducing agents such as dithiothreitol on disulfide bonds which may be present in the protein or desired protein fragment.

Also within the scope of this invention is the generation of linking chemistries from phenylamine (aniline) substituents such as those prepared by nitration of an aromatic ring substituent as described above followed by reduction as described above. Such aniline derivatives can be treated with aqueous hydrochloric acid and sodium nitrite (to form HONO) which will then react with the amine to form the corresponding diazonium salt. Said diazonium salt material can be coupled to tyrosine moieties on proteins via diazo linkages to the aromatic ring containing the hydroxyl group in the protein.

In addition, a chelating agent of this invention containing a substituent comprising an amine as described above can react with the N-hydroxysuccinimido ester of alpha-iodoacetic acid or with alpha-iodoacetic acid anhydride to produce the iodoacetamide derivative. This material can be reacted with proteins containing free sulfhydryl groups such as those utilized in the reactions of maleimide derivative as described above. An iodoacetamide group will also react with amines on proteins, such as the epsilon amine of lysine and the terminal amine of a peptide chain.

In addition, a chelating agent of this invention containing a substituent comprising an amine as described above can be alkylated at the amine group with a nitrile-containing alkylhalide such as Br—$(CH_2)_n$—CN to provide a nitrile wherein n is an integer from 1 to 10. Said amine can also be alkylated with a nitrile-containing benzylic halide such as alpha-bromomethylbenzonitrile to provide a benzonitrile. Furthermore, said amine can be acylated with an active ester (or similarly activated carbonyl derivative) of a carboxylic acid which contains a nitrile functionality (such as a cyanobenzoyl system and an aliphatic acid derivative such as a cyanoacetic acid derivative) to provide a nitrile amide. Any of these nitriles can be converted into the corresponding amidate by the action of alcohol and anhydrous HCl. These amidates will react with amines on proteins such as the epsilon amines of lysines and the terminal amines of peptide chains.

It should be recognized that in all of the above reaction schemes, acid moieties such as carboxylic species comprising Q in structure I of the unsymmetrical oligo-2,6-pyridine chelating agents of this invention can be protonated or can be present as ionic species (such as, for example, sodium salts). The extent of protonation and of deprotonation of any one species is a function of the pH of the reaction medium which contains both the protein reactive group containing reagent and the protein. The use of buffer salts such as, for example, phosphate, borate, citrate and acetate buffers to control the pH of the reaction medium is a part of this aspect of the invention.

While the foregoing discussion of synthetic routes useful for the preparation of representative protein reactive groups has been focused on certain preferred terpyridine systems defined by structure III, it will be understood that these chemistries can be applied to the wider variety of compounds defined more generally by structure I as needed to carry out the purposes of this invention.

The products of the reaction of any of these protein reactive group containing chelators with proteins (or other immunoreactive groups) can be purified by conventional techniques such as diafiltration, HPLC, electrophoresis, and the like. The proteins (or other immunoreactive groups) may be subsequently modified with agents such as PEG (polyethylene glycol) reagents as is well known in the art to impart reduced immunogenicity to the modified proteins.

The modified proteins can be treated with radioisotopes of metal ions such as $^{90}Y^{+3}$ (as a non-limiting example) and the radionuclide-chelate-protein can be used for the therapeutic treatment of tumors, particularly if the protein is a tumor antigen specific antibody or fragment thereof.

The modified proteins can be treated with radioisotopes of metal ions such as $^{111}In^{+3}$ or $^{187}Y^{+3}$ (as non-limiting examples) and the radionuclide-chelate-protein so produced can be used for the diagnostic imaging of tumors in cancer patients, particularly if the protein is a tumor antigen specific antibody or fragment thereof.

In one embodiment, this invention also provides metal complexes comprising the unsymmetrical oligo-2,6-pyridine chelating agents of this invention as described above bound, i.e., chelated, to one or more metal ions.

The term 'metal ion' as used herein is intended to include any ion of an element other than hydrogen that has an oxidation state equal to or greater than 1 and which can bind to a complexing agent of this invention through interaction with sites of high electron density in the complexing agent such as at heteroatom sites. The interaction of the metal ion with sites of high electron density in the complexing agent can be in the form of a Lewis acid-base interaction, wherein the oxidation state of metal ion is stabilized by interaction with donated electron density from sites of high electron density of the complexing agent. A metal ion can also interact with sites of high electron density in the complexing agent to form a salt in the form of an ionic association between a positively charged metal ion such as a lanthanide ion or a yttrium ion and a negatively charged substituent on the unsymmetrical oligo-2,6-pyridine complexing agent such as a carboxylate anion substituent. A metal ion can also interact with sites of high electron density in the complexing agent to form a covalent bond between the metal which has an oxidation state equal to or greater than 1 such as rhenium or technetium and a heteroatom of the unsymmetrical oligo-2,6-pyridine complexing agent such as a sulfur or nitrogen or oxygen atom.

Metal ions can be easily complexed to the chelating agent, for example, by merely exposing or mixing an aqueous solution containing the chelating agent with a metal salt, preferably in an aqueous solution. Preferably such solution has a pH in the range of about 4 to about 11. The metal ion salt can be any composition containing the metal ion including compositions that contain organic acids, organic acid ions, and chelating agents such as acetic acid, acetate ion, salicylic acid, salicyalate ion, citric acid, citrate ion, oxalic acid, oxalate ion, acetylacetone, acetylacetonate ion, amino acid and amino acid ion containing solutions such as glutamic acid and aspartic acid solutions, and solutions of iminodiacetic acid, ethylenediaminetetraacetic acid and related compounds. Salts with a low water solubility (i.e., a metal salt such as lead sufide or yttrium phosphate that has a large solubility product or low water solubility in the absence of a solubilizing agent such as a chelating agent) is useful, but preferably the salt is a water soluble salt of the metal such as, for example, a halogen or nitrate salt such as europium chloride or yttrium chloride or copper nitrate. More preferably such salts are selected so as not to interfere with the binding of the metal ion to the chelating agent. Such interference may occur, for example, as the result of removal of the ion from solution by precipitation as a not completely soluble salt. This would result in a slower rate of binding of the desired metal ion to the chelating agent with respect to the rate that can occur in the presence of a fully soluble salt. The chelating agent is preferably in aqueous solution at a pH of between about 5 and about 9, more preferably between pH about 6 to about 8. The chelating agent can be mixed with buffer salts such as citrate, acetate, phosphate and borate to produce the optimum pH. Preferably, said buffer salts are selected so as not to interfere with the subsequent binding of the metal ion to the chelating agent as described above. Presently preferred buffered aqueous solution comprise sodium acetate plus acetic acid in water as well as citric acid plus sodium citrate in water. Presently preferred metal ions are $In^{+3}$, $Eu^{+3}$, and $Y^{+3}$, and a presently preferred metal ion salts are $InCl_3$, $EuCl_3$, and $YCl_3$.

In another embodiment, the ions, $M_1$ and $M_2$, of two separate elements can be chelated simultaneously to unsymmetrical oligo-2,6-pyridine chelating agents of this invention represented by Structure I wherein "a" is one. This can be done by a process comprising the sequential exposure of said unsymmetrical oligo-2,6-pyridine chelating agent to a solution 1 containing metal ion $M_1$ as described above for an effective time to allow the complexation of some or all of $M_1$ by the chelating agent, followed by the optional removal of excess amounts of metal ion, $M_1$, from the vicinity of the chelating agent (for example, by precipitation and filtration), followed by subsequent exposure of the chelated $M_1$ species thus formed to a solution 2 containing a second metal ion, $M_2$, for a time and under conditions comprising buffer and pH as described above sufficient to permit the formation of a chelate of $M_1$ and $M_2$. Preferably, the molar amount of ion $M_1$ in solution 1 is equal to or less than the molar amount of the chelating agent of this invention, and the molar amount of ion $M_2$ in solution 2 can be less than, equal to, or greater than the molar amount of the chelating agent of this invention complexed to $M_1$. More preferably, the molar amount of ion $M_2$ in solution 2 is less than or equal to the molar amount of the chelating agent of this invention complexed to $M_1$. A preferred amount of time for the formation of a metal complex is in the range from about one second to about two hours, preferably from 15 seconds to one hour, and more preferably from about 1 minute to about 20 minutes.

In another embodiment, the ions, $M_1$ and $M_2$, of two separate elements can be chelated sequentially to unsymmetrical oligo-2,6-pyridine chelating agents of this invention represented by Structure I wherein "a" is one. This can be by a process comprising the sequential exposure of said unsymmetrical oligo-2,6-pyridine chelating agent to a solution 1 containing metal ion $M_1$ as described above for an effective time to allow the complexation of some or all of $M_1$ by the chelating agent, followed by the optional removal of excess amounts of metal ion, $M_1$, such as by precipitation and filtration from the vicinity of the chelating agent, followed by subsequent exposure of the chelated $M_1$ species thus formed to a solution 2 containing a second metal ion, $M_2$, for a time and under conditions comprising buffer and pH as described above sufficient to permit the formation of a chelate of $M_2$.

In addition to ions of alkali metals such as sodium, potassium, and cesium, and to ions of alkaline earth metals such as magnesium, calcium, and barium, preferred metal ions can be selected from, but are not limited to, ions of elements of groups IIA through VIA. Preferred metals include those of atomic number 12, 13, 20, the transition elements 21 to 33, 38 to 52, 56, 72 to 84 and 88 and those of the lanthanide series (atomic number 57 to 71 sometimes hereinafter referred to as the lanthanide metals). Ions of yttrium and the lanthanide metals are especially preferred.

In another embodiment, the metal chelate of this invention can comprise a fluorescent metal ion. The fluorescent metal ion can be selected from, but is not limited to, metals of atomic number 57 to 71. Ions of the following metals are preferred: La, Ce, Pr, Nd, Pm, Sm, Eu, Gd, Tb, Dy, Ho, Er, Tm, Yb, and Lu. $Eu^{+3}$ ion is especially preferred. A Eu+3 ion complex of compound (26) is an example of a preferred metal ion complex.

Metal complexes of this invention comprising a novel unsymmetrical oligo-2,6-pyridine chelating agent of this invention as described above chelated to one or more fluorescent metal ions such as, for example, a $Eu^{+3}$ ion can exhibit utility in time delayed fluorescence and assays which involve time delayed fluorescence such as in the detection of fluorescent metal ions such as $Eu^{+3}$. In such an assay, an unsymmetrical oligo-2,6-pyridine chelating agent of this invention is exposed to a material such as a solution that contains a fluorescent metal ion such as $Eu^{+3}$ ion for an effective amount of time so that a complex is formed between the chelating agent and the $Eu^{+3}$ ion. A preferred amount of time is from about one second to one hour, preferably from 15 seconds to 10 minutes. The complex is then irradiated with an excitation light such as, for example, a pulse of light having a maximum intensity at a wavelength of about 385 nanometers. The excitation light pulse is then stopped or blocked from further access to the metal complex, an effective time such as about 400 microseconds is allowed to elapse, and emission of light is then detected and measured with a detector capable of determining intensity of light as a function of wavelength. The wavelength of the emitted light is longer than the wavelength of the excitation light. The effective time delay is preferably about 400 microseconds or longer so that no interference for ambient fluorescent emitters interferes with the detection of the desired fluorescence in this type of assay. A preferred composition for this type of assay comprises unsymmetrical oligo-2,6-pyridine chelating agent (26) chelated to a $Eu^{+3}$ ion.

In another embodiment, the metal chelate of this invention can comprise a paramagnetic ion which is suitable for the use in nuclear magnetic resonance applications which include in vitro and in vivo diagnostic imaging such as of animal and human tissue using MRI techniques as well as in applications such as in nuclear magnetic resonance chemical shift reagents. The paramagnetic ion is an ion of an element which can be selected from elements of atomic number 21 to 29, 43, 44 and 57 to 71. The following elements are preferred: Cr, V, Mn, Fe, Co, Ni, Cu, La, Ce, Pr, Nd, Pm, Sm, Eu, Gd, Tb, Dy, Ho, Er, Tm, Yb and Lu. Mn, Gd, and Dy are especially preferred. $Gd^{+3}$ and $Dy^{+3}$ are especially preferred ions for use with compound (19a). The chelation of one metal ion with each unsymmetrical oligo-2,6-pyridine chelating moiety in compound (19a) is useful in this regard. Such a metal complex can be formed as described above.

In another embodiment, the metal chelate of this invention can comprise a radionuclide. The radionuclide can be selected, for example, from radioisotopes of Sc, Fe, Pb, Ga, Y, Bi, Mn, Cu, Cr, Zn, Ge, Mo, Tc, Ru, In, Sn, Sr, Sm, Lu, Sb, W, Re, Po, Ta and Tl. Preferred radionuclides include $^{44}Sc$, $^{64}Cu$, $^{67}Cu$, $^{111}In$, $^{212}Pb$, $^{68}Ga$, $^{90}Y$, $^{87}Y$, $^{153}Sm$, $^{212}Bi$, $^{99m}Tc$, $^{186}Re$ and $^{188}Re$. Of these, especially preferred is $^{90}Y$.

In some applications, a metal chelate plus a mixture of metal ions such as sodium ions and yttrium ions is useful. For example, solution of a metal chelate of this invention such a compound (26) in a sodium acetate buffer can be treated with a less than stoichiometric quantity of a radionuclide such as $^{90}Y$, and after an effective time during which chelation of substantially all of the radionuclide occurs, the subsequent mixture containing $^{90}Y$ bound to metal chelate plus the sodium salt of non-$^{90}Y$-containing metal chelate can be useful without further separation of the individual components, for example, in radioscintigraphy analysis of proteins separated by electrophoresis or for solubilizing radionuclides such as $^{90}Y$ in the presence of ions such as phosphate ions that would otherwise combine with the metal ion to form a precipitate such as yttrium phosphate. In a bulk, a solution of the metal chelate plus non-radionuclide containing chelating agent of this aspect of this invention preferably contains a ratio of metal radionuclide ion to total amount of chelating agent that is effective in such applications. In preferred embodiments, the mole ratio of such metal ion per chelating agent in a bulk solution is from about 1:1000 to about 1:1.

In another embodiment, this invention provides a targeting immunoreagent comprising a metal ion, a complexing agent, and an immunoreactive group attached through a linking group to said complexing agent, wherein the complexing agent has the structure I as defined above and the linking group between the complexing agent and the immunoreactive group comprises the residue of the protein reactive group on the complexing agent.

The targeting immunoreagent of this invention includes an immunoreactive group bonded, by a linking group that comprises the residue of a protein reactive group, to the unsymmetrical oligo-2,6-pyridine complexing agent which is chelated to a metal ion. The targeting immunoreagent thus comprises a conjugate of a complex having the structure I above and the immunoreactive group. The complexing agent and the metal can be complexed either before or after the complexing agent is attached to the immunoreactive group.

As used herein the term "immunoreactive group" is meant to include any organic compound which is capable of bonding, covalently or non-covalently, to a chelating agent of this invention and which is found in a living organism or is useful in the diagnosis, treatment or genetic engineering of cellular material or living organisms, and which has a capacity for interaction with another component which may be found in biological fluids or associated with cells to be treated such as tumor cells. Immunoreactive groups for use in the practice of this invention are those which have a receptor molecule specific to a ligand of interest. Thus, a specific binding reaction involving the reagent can be used for the targeting expected. Examples of such ligand-receptor complexes include, but are not limited to antibody-antigen, avidin-biotin, repressor (inducer)—promoter of operons and sugar-lectin complexes. Additionally, complementary, contiguous (as well as non-contiguous) sequences of nucleic acids which complementary sequences can pairwise form hybridized products of complementary contiguous strands (as well as complementary, non-contiguous sequences which can pairwise form hybridized products of complementary non-contiguous strands), are also considered specific binding materials as the term is used herein. Examples of contiguous sequences include sequences of deoxyribonucleic acids (DNA) comprising the deoxyribonucleosides adenosine (dA), thymidine (dT), cytidine (dC), and guanosine (dG) arrayed in a given order and the complementary sequences comprising dT, dA, dG and dC, arrayed with a respective, complementary order).

The immunoreactive group can be selected from a wide variety of naturally occurring or synthetically prepared materials including, as non-limiting examples, enzymes, amino acids, peptides, polypeptides, proteins, lipoproteins, glycoproteins, lipids, phospholipids, hormones, growth factors, steroids, vitamins, polysaccharides, viruses, protozoa, fungi, parasites, rickettsia, molds, and components thereof, blood components, tissue and organ components, pharmaceuticals, haptens, lectins, toxins, nucleic acids (including oligonucleotides), antibodies (monoclonal and polyclonal), anti-antibodies, antibody fragments, antigenic materials (including proteins and carbohydrates), avidin and derivatives thereof, biotin and derivatives thereof, and others known to one skilled in the art. In addition, an immunoreactive group can be any substance which when presented to an immunocompetent host will result in the production of a specific antibody capable of binding with that substance, or the antibody so produced, which participates in an antigen-antibody reaction.

Preferred immunoreactive groups are antibodies and various immunoreactive fragments thereof (i.e., antibody fragments) as long as they contain at least one reactive site for reaction with a protein reactive group of the chelating agent of Structure I. That site can be inherent to the immunoreactive species or it can be introduced through appropriate chemical modification of the immunoreactive species as described below.

As used herein, the term "antibody fragment" refers to an immunoreactive material which comprises a residue of a whole antibody, which antibody characteristically exhibits an affinity for binding to an antigen. The term "affinity", as used herein, refers to the thermodynamic expression of the strength of interaction or binding between an antibody combining site (or other ligand) and an antigenic determinant (or receptor) and, thus, of the sterochemical and charge compatibility between them; as such it is the expression of the equilibrium or association constant for an antibody-antigen (or a ligand-receptor) interaction. Antibody fragments exhibit at least a percentage of said affinity for binding to said antigen, the percentage being in the range of 0.001 per cent to 1,000 per cent, preferably 0.01 per cent to 1,000 per cent, more preferably 0.1 per cent to 1,000 per cent, and most preferably 1.0 per cent to 1,000 per cent, of the relative affinity of the whole antibody for binding to the antigen.

An antibody fragment can be produced from an antibody (a) by a chemical reaction comprising one or more chemical bond cleaving reactions employing as reactants one or more chemical components selected from a group comprising whole antibody, amino acids, peptides, carbohydrates, linking groups as defined herein, spacing groups as defined herein, protein reactive groups as defined herein, and larger antibody fragments or partially fragmented antibodies such as are produced as described herein; (b) by a chemical reaction comprising one or more chemical bond forming reactions employing as reactants one or more chemical components selected from a group comprising amino acids, peptides, carbohydrates, linking groups as defined herein, spacing groups as defined herein, protein reactive groups as defined herein, and antibody fragments such as are produced as described herein; and (c) by a molecular biological process, a bacterial process, or by a process comprising a genetic engineering of antibody genes.

An antibody fragment can be derived by one or more of the following:

(a) by cleavage of one or more chemical bonds comprising an antibody, said bonds being selected from, for example, carbon-nitrogen bonds, sulfur-sulfur bonds, carbon-carbon bonds, carbon-sulfur bonds, and carbon-oxygen bonds, and wherein the method of said cleavage is selected from:

(i) a catalysed chemical reaction comprising the action of a biochemical catalyst such as an enzyme, for example, papain or pepsin which enzymes to those skilled in the art are known to produce antibody fragments commonly referred to as Fab and Fab'2, respectively;

(ii) a catalysed chemical reaction comprising the action of an electrophilic chemical catalyst such as a hydronium ion which, for example, favorably occurs at a pH equal to or less than 7;

(iii) a catalysed chemical reaction comprising the action of a nucleophilic catalyst such as a hydroxide ion which, for example, favorably occurs at a pH equal to or greater than 7; and (iv) a chemical reaction comprising a substitution reaction employing a reagent which is consumed in a stoichiometric manner such as a substitution reaction at a sulfur atom of a disulfide bond by a reagent comprising a sulfhydryl group;

(v) a chemical reaction comprising a reduction reaction such as the reduction of a disulfide bond; and (vi) a chemical reaction comprising an oxidation reaction such as the oxidation of a carbon-oxygen bond of a hydroxyl group or the oxidation of a carbon-carbon bond of a vicinal diol group such as occurs in a carbohydrate moiety by the action of sodium periodate; or (b) by formation of one or more chemical bonds between one or more reactants, such as formation of one or more covalent bonds selected from, for example, carbon-nitrogen bonds (such as, for example, amide bonds, amine bonds, hydrazone bonds, and thiourea bonds), sulfur-sulfur bonds such as disulfide bonds, carbon-carbon bonds, carbon-sulfur bonds, and carbon-oxygen bonds, and employing as reactants in said chemical bond formation one or more reagents comprising amino acids, peptides, carbohydrates, linking groups as defined herein, spacing groups as defined herein, protein reactive groups as defined herein, and antibody fragments such as are produced as described in (a), above; or, (c) by formation of one or more non-covalent "bonds" between one or more reactants or components such as, for example, (i) non-covalent hydrophobic interactions (or "bonds") which occur in a polar medium (such as an aqueous medium) between chemical species that each independently comprise mutually accessible regions of low polarity (such as regions containing aliphatic hydrocarbon and carbocyclic groups), and (ii) non-covalent hydrogen "bond" interactions such as occur in the interaction of an oligonucleotide with a complementary oligonucleotide; or (d) by the well known methods of molecular biology and genetic engineering of antibody genes, for example, in the genetic engineering of a single chain immunoreactive group or a Fv fragment through manipulation of DNA sequence coding.

An antibody fragment can be produced as a result of a combination of one or more of the above methods such as by first genetically engineering an antibody which antibody is expressed by a cell line, is harvested and purified, and then reduced or oxidized to produce an antibody fragment.

In certain embodiments, the immunoreactive group can be an enzyme which contains a reactive group for attachment to the chelating agent as a result of reaction or the reactive group with the protein reactive group of the chelating agent. Representative enzymes include, but are not limited to, aspartate aminotransaminase, alanine aminotransaminase, lactate dehydrogenase, creatine phosphokinase, gamma glutamyl transferase, alkaline acid phosphatase, prostatic acid phosphatase, horseradish peroxidase, monoamine oxidase, dihydrofolate reductase, and various esterases.

If desired, the immunoreactive group can be chemically modified or conformationally altered to provide reactive functional groups for use in attaching the immunoreactive group to the protein reactive group of the chelating agent by techniques known to those skilled in the art. Such techniques include the use of linking moieties and chemical modification such as described in WO-A-89/02931 and WO-A-89/2932, which are directed to modification of oligonucleotides, and U.S. Pat. No. 4,719,182.

Two highly preferred uses for the targeting immunoreagent compositions of this invention are for the diagnostic imaging of tumors and the radiological treatment of tumors. Preferred immunological groups therefore include antibodies (sometimes hereinafter referred to as Ab) to tumor-associated antigens. Specific non-limiting examples include B72.3 and related antibodies (described in U.S. Pat. Nos. 4,522,918 and 4,612,282) which recognize colorectal tumors, 9.2.27 and related anti-melanoma antibodies, D612 and related antibodies which recognize colorectal tumors, UJ13A and related antibodies which recognize small cell lung carcinomas, NRLU-10 and related antibodies which recognize small cell lung carcinomas and colorectal tumors (Pan-carcinoma), 7E11C5 and related antibodies which recognize prostate tumors, CC49 and related antibodies which recognize colorectal tumors, TNT and related antibodies which recognize necrotic tissue, PR1A3 and related antibodies which recognize colon carcinoma, ING-1 and related antibodies, which are described in International Patent Publication WO-A-90/02569, B174, C174 and related antibodies which recognize squamous cell carcinomas, B43 and related antibodies which are reactive with certain lymphomas and leukemias, and anti-HLB and related monoclonal antibodies. A presently especially preferred antibody is ING-1.

Antibodies and other useful immunoreactive groups as described above are large, complex molecules which can have multiple reactive sites (for example, reactive primary amine sites such as lysyl θ-amine sites) which can be involved in the attachment of a complexing agent of this invention to said immunoreactive groups. Consequently, an immunoreactive group can have appended to it one or more complexing agents of this invention as a result of reaction of the reactive site of the immunoreactive group with the protein reactive group of the complexing agent. Thus, the term immunoreactive group is intended to include immunoreactive groups which have one or more complexing agent molecules bonded thereto through one or more protein reactive groups.

The immunoreactive material contains a reactive group which can react or combine with the protein reactive group on the chelating agent as defined in Structure I. The result of such a reaction or interaction is the formation of the residue of a linking group between the immunoreactive material and the chelating agent. Suitable reactive sites on the immunoreactive material include amine sites of lysine; terminal peptide amines; carboxylic acid sites, such as are available in aspartic acid and glutamic acid residues; sulfhydryl sites such as in cysteine residues; carbohydrate sites and oxidized carbohydrate sites; activated carbon-hydrogen and carbon-carbon bonds which can react through insertion via free radical reaction or nitrene or carbene reaction of a so activated residue; sites of oxidation including, for example, a vicinal diol site of a carbohydrate moiety and a serine alcohol, each of which can be oxidized to an aldehyde; sites of reduction, for example a disulfide linkage which can be reduced to form a sulfhydryl group; aromatic sites such as the hydroxyaromatic group of tyrosine which can react with diazonium cations such as aryl diazonium cations; and hydroxyl sites such as the phenolic hydroxyl group of tyrosine which can be alkylated (for example, by haloalkyl groups such as chloromethylaryl groups, or by activated carbon-carbon double bonds such as vinyl sulfonyl groups), the hydroxyl group of serine, and the hydroxyl group of a carbohydrate moiety, which can react, for example, with anhydrides, active esters, and with acyl halides.

In one aspect, the phrase "residue of a linking group" as used herein refers to a moiety that remains, results, or is derived, from the reaction of a protein reactive group with a reactive site on a protein. The phrase "protein reactive group" as used herein refers to any group which can react with functional groups typically found on proteins. However, it is specifically contemplated that such protein reactive groups can also react with functional groups typically found on relevant nonprotein molecules. The alkyl portions of said linking groups can contain from 1 to about 20 carbon atoms as described previously. The aryl portions of said linking groups can contain from about 6 to about 20 carbon atoms;

Preferred linking groups are derived from protein reactive groups selected from but not limited to:

(1) a group that will react directly with amine, alcohol, or sulfhydryl groups on the immunoreactive protein or biological molecule containing the reactive group, for example, active halogen containing groups including, for example, chloromethylphenyl groups and chloroacetyl (ClCH2C(=O)—] groups, activated 2-(leaving group substituted)-ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in conventional photographic gelatin hardening agents;

(2) a group that can react readily with modified proteins or biological molecules containing the immunoreactive group, i.e., proteins or biological molecules containing the immunoreactive group modified to contain reactive groups such as those mentioned in (1) above, for example, by oxidation of the protein to an aldehyde or a carboxylic acid, in which case the "linking group" can be derived from protein reactive groups selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of said linking groups can contain from 1 to about 20 carbon atoms. The aryl portions of said linking groups can contain from about 6 to about 20 carbon atoms; and (3) a group that can be linked to the protein or biological molecule containing the immunoreactive group, or to the modified protein as noted in (1) and (2) above by use of a crosslinking agent. The residues of certain useful crosslinking agents, such as, for example, homo-bifunctional and heterobifunctional gelatin hardeners, bisepoxides, and bisisocyanates can become a part of a linking group during the crosslinking reaction. Other useful crosslinking agents, however, can facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847 and the ethers of U.S. Pat. No. 4,877,724. With these crosslinking agents, one of the reactants such as an immunoreactive group must have a carboxyl group and the other such as the chelating agent of this invention must have a reactive amine, alcohol, or sulfhydryl group. In amide bond formation, the crosslinking agent first reacts selectively with the carboxyl group, then is split out during reaction of the thus "activated" carboxyl group with an amine to form an amide linkage between the immunoreactive group and the chelating agent and thus covalently bonding the two moieties. An advantage of this approach is that crosslinking of like molecules is avoided, whereas the reaction of, for example, homo-bifunctional crosslinking agents is nonselective and unwanted crosslinked molecules are obtained.

Useful linking groups are derived from various heterobifunctional cross-linking reagents such as those listed in the Pierce Chemical Company Immunotechnology Catalog—Protein Modification Section, (1991 and 1992). Useful non-limiting examples of such reagents include: Sulfo-SMCC, i.e., Sulfosuccinimidyl 4-(N-maleimidomethyl) cyclohexane-1-carboxylate; Sulfo-SIAB, i.e., Sulfosuccinimidyl (4-iodoacetyl)aminobenzoate; Sulfo-SMPB, i.e., Sulfosuccinimidyl 4-(p-maleimidophenyl)butyrate; 2-IT, i.e., 2-Iminothiolane; and SATA, i.e., N-Succinimidyl S-acetylthioacetate.

In addition to those falling within the foregoing description, linking groups can also comprise (and be derived from) pairs of complementary sequences of nucleotides or residues of pairs of complementary sequences of nucleotides. Such complementary pairs of sequences can be naturally occurring or they can be modified. Preferably, each complementary sequence of nucleotides is a non-self-associating oligonucleotide sequence (i.e., each sequence contains a region of complementarity which is less than 6 base pairs in sequence length. Particularly useful, non-limiting reagents for incorporation of modified nucleotide moieties containing reactive functional groups, such as amine and sulfhydryl groups, into an oligonucleotide sequence are commercially available from, for example, Clontech Laboratories Inc. (Palo Alto, Calif.) and include Uni-Link AminoModifier (Catalog #5190), Biotin-ON phosphoramidite (Catalog #5191), N-MNT-C6-AminoModifier (Catalog #5202), AminoModifier II (Catalog #5203), DMT-C6-3'Amine-ON (Catalog #5222), C6-ThiolModifier (Catalog #5211), and the like.

In one aspect, linking groups of this invention are derived from the reaction of a reactive functional group such as an amine or sulfhydryl group as are available in the above Clontech reagents, one or more of which has been incorporated into an oligonucleotide sequence, with, for example, one or more of the previously described protein reactive groups such as heterobifunctional protein reactive groups, one or more of which has been incorporated into, for example, an immune reactive agent of this invention.

Respective complementary individual oligonucleotide sequences are attached to the two components of the conjugate, one sequence to the immune reactive agent and the complementary oligonucleotide sequence to the chelating agent. The hybrid formed between the two complementary oligonucleotide sequences then comprises the linking group between the immunoreactive group and the chelating agent.

Two or more copies of the same oligonucleotide sequence can be linked, for example, in tandem to one immunoreactive group and a complementary oligonucleotide sequence comprising multiple chelating agents can be added. The multiple hybrids formed between the two complementary oligonucleotide sequences then comprises the linking group between the immunoreactive group and multiple chelating agents.

An antibody or fragment thereof containing a carbohydrate region can be attached to the complexing agent through the carbohydrate region of the antibody, such as described in U.S. Pat. No. 4,937,183, the disclosure of which is hereby incorporated herein by reference in its entirety. Useful methods for attaching an antibody are also described in U.S. Pat. Nos. 4,671,958; 4,699,784; 4,741,900; and 4,867,973. The term "protein reactive group" as defined herein is intended to include such linkages.

Preferred linking groups also include nitrogen atoms in groups such as amino, imido, nitrilo and imino groups; spacer groups such as alkylene groups, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups; carbonyl; sulfonyl; sulfinyl; ether; thioether; ester, i.e., carbonyloxy and oxycarbonyl; thioester, i.e., carbonylthio, thiocarbonyloxy, and oxythiocarboxy; amide, i.e., iminocarbonyl and carbonylimino; thioamide, i.e., iminothiocarbonyl and thiocarbonylimino; thio; dithio; phosphate; phosphonate; urelene; thiourelene; urethane, i.e., iminocarbonyloxy,and oxycarbonylimino; an amino acid linkage, i.e., a

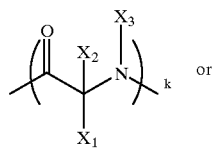

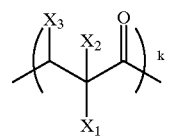

group wherein k=1 and $X_1$, $X_2$, $X_3$ independently are H, alkyl, containing from 1 to 18, preferably 1 to 6 carbon atoms, such as methyl, ethyl and propyl, such alkyl optionally being interrupted by 1 or mor heteroatoms such as oxygen, nitrogen and sulfur, substituted or unsubstituted aryl, containing from 6 to 1 6, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above; or a peptide linkage, i.e., a

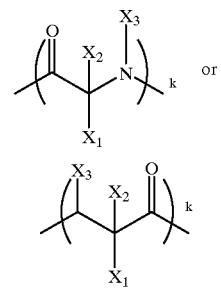

group wherein k>1 and each X independently is represented by a group as described for $X_1$, $X_2$, $X_3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry as described above. An especially preferred linking group is a thiourea group which is formed by the reaction of an isothiocyanate group and an amino group. Preferably, the isothiocyanate group is a protein reactive group of a chelating agent of this invention such as compound (21), and the amino group is a reactive group in an immunoreactive group such as an antibody such as ING-1.

The linking groups can contain various substituents which do not interfere with the coupling reaction between the chelating agent of this invention and the immunoreactive group. The linking groups can also contain substituents which can otherwise interfere with such reaction, but which during the coupling reaction, are prevented from so doing with suitable protecting groups commonly known in the art and which substituents are regenerated after the coupling reaction by suitable deprotection. The linking groups can also contain substituents that are introduced after the coupling reaction. For example, the linking group can be substituted with substituents which comprise a halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; or the residue of a chelating group.

The products of the reaction of any of these protein reactive group containing chelating agents with immunoreactive groups, preferably with proteins, can be purified by conventional techniques such as diafiltration, HPLC, electrophoresis, and the like. The immunoreactive groups may be subsequently modified with agents such as PEG (polyethylene glycol) reagents as is well known in the art to impart reduced immunogenicity to the modified proteins.

Techniques for performing the binding of the immunoreactive group to the complexing agents of this invention include simply mixing the materials together, preferably in aqueous solution in the presence of a buffer salt such as sodium borate or sodium phophate, or sodium acetate at a pH of about 4 to about 11, preferably from about 7 to about 10. Other techniques such as the use of heterobifunctional linking chemistries as described above are known in the art.

The molar ratio of the complexing agent of this invention to the immunoreactive group can vary from about 0.5:1 to about 10:1, or more. In some embodiments, the molar ratio of complexing agent of this invention to immunoreactive group is from about 1:1 to about 6:1. In some uses of the immunoconjugates of this invention, the bulk ratio of the chelating agent to the immunoreactive group can be an apparent fraction because the immunoconjugate can be used in the presence of unmodified immunoreactive group. For example, a mixture of an unmodified antibody such as ING-1 together with an immunoconjugate comprising a residue of ING-1, a residue of compound (21), and a radionuclide ion such as $^{111}In^{+3}$ can be useful in an application such as the radioscintigraphic analysis of a tumor in a patient. As such, the bulk ratio of chelating agent to ING-1 in such a mixture can be from about 0.01 to about 6, preferably from about 0.1 to about 3, and more preferably about 1:1.

The immunoreagents of this invention comprise a metal ion, a complexing agent as described in structure I above, and an immunoreactive group as described above attached by a linking group to the complexing agent which linking group comprises the residue of a protein reactive group on the complexing agent. The complexing agent and the metal radionuclide can be complexed either before or after the complexing agent is attached to the immunoreactive group. The immunoreagent of this invention in bulk use rather than as individual molecules can contain a wide range of ratios of metal ion to complexing agent. In preferred embodiments, the mole ratio of metal ion to complexing agent is from about 1:1000 to about 1:1. In some embodiments, the ratio of the complexing agent to the immunoreactive group can vary widely from about 0.5:1 to 10:1 or more. In some embodiments, the mole ratio of complexing agent to immunoreactive groups is from about 1:1 to about 6:1.

In one embodiment, this invention provides a targeting radioactive immunoreagent comprising a metal radionuclide ion, a complexing agent, and an immunoreactive group which is attached through a linking group to said complexing agent, wherein the complexing agent has the structure I as defined above, the immunoreactive group is as described above, and the linking group between the complexing agent and the immunoreactive group comprises the residue of the protein reactive group on the complexing agent as described above. The radionuclide ion can be selected, for example, from Sc, Fe, Pb, Ga, Y, Bi, Mn, Cu, Cr, Zn, Ge, Mo, Tc, Ru, In, Sn, Re, Sr, Sm, Lu, Eu, Dy, Sb, W, Po, Ta and Tl ions. Preferred radionuclides include $^{44}Sc^{+++}$, $^{64}Cu^{++}$, $^{67}Cu^{++}$, $^{111}In^{+++}$, $^{212}Pb^{++}$, $^{68}Ga^{++}$, $^{90}Y^{+++}$, $^{177}Lu^{++}$, $^{186}Re^{++}$, $^{188}Re^{++}$, $^{99m}Tc^{++}$, $^{87}Y^{+++}$, and $^{212}Bi^{+++}$ ions. Of these, the most preferred are $^{90}Y^{+++}$ ions. A preferred embodiment of a targeting immunoreagent comprises the antibody ING-1 linked at a lysine amine site by a thiourea group formed as described above to the residue of chelating agent (21) which is chelated to a $^{90}Y^{+3}$ ion. Another preferred embodiment of a targeting immunoreagent comprises the antibody ING-1 linked at a lysine amine site by a thiourea group formed as described above to the residue of chelating agent (21) which is chelated to a $^{111}In^{+3}$ ion.

The metal radionuclide ion and the complexing agent of the targeting immunoreagent are easily complexed by merely mixing an aqueous solution of the immunoreagent containing the complexing agent with a metal radionuclide salt in an aqueous solution preferably having a pH of 4 to 11 as described above. The salt is preferably any water soluble salt of the metal such as a halide or nitrate salt. The targeting immunoreagent containing the complexing agent of this invention and the metal ion is generated in aqueous solution at a pH of between about 5 and about 10 and preferably from about 6 to about 9. The targeting immunoreagent containing the complexing agent of this invention and the metal ion is generated optionally in the presence of buffers, such as acetate, citrate, phosphate and borate, to produce a desired optimum pH. Preferably, the buffer salts are selected so as not to interfere with the initial and subsequent binding of the metal ion to the chelating agent. A presently preferred buffer is acetate when the targeting immunoreagent containing the complexing agent of this invention and the metal ion comprise ING-1 linked by a thiourea group to compound (21) which is chelated to yttrium ion as described above.

The targeting immunoreagent of this invention comprising a radioisotope of a metal ion such as $^{90}Y^{+3}$ (as a non-limiting example) can be used for the therapeutic treatment of tumors, particularly if the immunoreagent is a tumor antigen specific antibody or a fragment of such an antibody. In therapeutic applications, the targeting immunoreagent of this invention preferably contains a ratio of metal radionuclide ion to chelating agent that is effective in such therapeutic applications. In preferred embodiments, the mole ratio of metal ion per chelating agent is from about 1:100 to about 1:1. In therapeutic applications, a preferred embodiment of a targeting immunoreagent comprises the antibody ING-1 linked at a lysine amine site by a thiourea group formed as described above to the residue of chelating agent (21) which is chelated to a $^{90}Y^{+3}$ ion.

The targeting immunoreagent of this invention comprising a radioisotope of a metal ion such as $^{111}In^{+3}$ or $^{187}Y^{+3}$ (as non-limiting examples) can be used for the diagnostic imaging of tumors in cancer patients, particularly if the immunoreagent is a tumor antigen specific antibody or a fragment of such antibody. In diagnostic imaging applications, the targeting immunoreagent of this invention preferably contains a ratio of metal radionuclide ion to chelating agent that is effective in such diagnostic imaging applications. In preferred embodiments, the mole ratio of metal ion per chelating agent is from about 1:10,000 to about 1:1. In diagnostic imaging applications, a preferred embodiment of a targeting immunoreagent comprises the antibody ING-1 linked at a lysine amine site by a thiourea group formed as described above to the residue of chelating agent (21) which is chelated to a $^{87}Y^{+3}$ ion. Another preferred embodiment of a targeting immunoreagent comprises the antibody ING-1 linked at a lysine amine site by a thiourea group formed as described above to the residue of chelating agent (21) which is chelated to a $^{111}In^{+3}$ ion.

In another embodiment, this invention provides a targeting paramagnetic immunoreagent comprising a paramagnetic metal ion as described above, the residue of a complexing agent of this invention as described above, and an immunoreactive group as described above attached through a linking group to said complexing agent as described above, wherein the complexing agent has the structure I as defined above and the linking group between the complexing agent and the immunoreactive group comprises the residue of the protein reactive group on the complexing agent as described above. Such targeting paramagnetic immunoreagents are useful in both in vitro and in vivo magnetic resonance imaging of tissue that is targeted by an immunoreagent (for example, tumor tissue in a mammal such as man, which tissue contains an abundance of tumor associated antigen to which an immunoreagent such as an antibody will bind). In magnetic resonance imaging applications, a preferred embodiment of a targeting immunoreagent comprises the antibody ING-1 linked at a lysine amine site by a thiourea group formed as described above to the residue of chelating agent (23) which is chelated to a $Gd^{+3}$ ion. Another preferred metal ion is $Dy^{+3}$.

In another embodiment, this invention provides a targeting fluorescent immunoreagent comprising a flourescent metal ion as described above, a complexing agent of this invention, and an immunoreactive group as described above attached through a linking group to said complexing agent, wherein the complexing agent has the structure I as defined above and the linking group between the complexing agent and the immunoreactive group comprises the residue of the protein reactive group on the completing agent. Such targeting fluorescent immunoreagents are useful in the in vitro detection of antigens which bind to the immunoreagent. Such antigens may be found in human tissue or fluids, and the detection of such antigens comprises a useful in vitro assay employing the chelating agents of this invention. Time delayed fluorescence assays and the sorting and separation of cells employing time delayed fluorescence detection techniques (such as in the separation of hybridoma cells which contain antigen on their surface, to which antigen the targeting immunoreagent of this invention binds, from cells which do not contain such antigen on their surface) comprise additional uses of the chelating agents of this invention and of the targeting fluorescent immunoreagents of this invention. In fluorescence detection assays, a preferred embodiment of a targeting immunoreagent comprises the antibody ING-1 linked at a lysine amine site by a thiourea group formed as described above to the residue of chelating agent (21) which is chelated to a $Eu^{+3}$ ion.

This invention also provides therapeutic and diagnostic compositions comprising the above-described targeting radioactive immunoreagents.

This invention also provides diagnostic compositions comprising the above-described targeting paramagnetic immunoreagents.

This invention also provides diagnostic compositions comprising the above-described targeting fluorescent immunoreagents.

This invention further provides a method for diagnostic imaging a site in a patient comprising a) administering to the patient an effective amount of the above-described radioactive immunoreagent capable of targeting the site, and b) imagewise activating a radiation-sensitive element or device, such as, for example, a film or electronic sensor, with the radiation emitted from the targeted site.

This invention further provides a method for diagnostic imaging a site in a patient or a site in a specimen from the patient comprising a) administering to the patient or to a site in a specimen from the patient an effective amount of the above-described paramagnetic immunoreagent capable of targeting the site in a pharmaceutically acceptable carrier therefor, and b) imagewise activating a nuclear magnetic resonance detection sensor element or device which is sensitive to a change in one or more nuclear magnetic relaxation properties of an isotope such as a proton at the site of the patient or at the site in a specimen from the patient while said site is exposed to a controlled magnetic field environment such as, for example, a magnetic field in a magnetic resonance imaging instrument, which change is induced by the paramagnetic metal ion of the immunoreagent.

This invention further provides a method for treating a disease site in a patient or a disease site in a specimen from the patient comprising administering to the patient or to a specimen from the patient an effective amount of a therapeutic composition comprising the above-described radioactive immunoreagent capable of targeting the site and a pharmaceutically acceptable carrier therefor.

This invention further provides a method for diagnostic imaging a site in a specimen from a patient comprising a) administering to the specimen an effective amount of a fluorescent composition comprising the above-described fluorescent immunoreagent capable of targeting a site in the specimen, b) irradiating the specimen with light which is absorbed by the metal complex of the immunoreagent, and c) imagewise activating a fluorescence emission sensor element or device, such as, for example, a film or electronic sensor, with the fluorescent light emitted from the targeted site. A preferred method uses time delayed fluorescence detection.

In another embodiment, the targeting immunoreagent of this invention can comprise a fluorescent metal ion. The fluorescent metal ion can be selected from, but is not limited to, metals of atomic number 57 to 71. Ions of the following metals are preferred: La, Ce, Pr, Nd, Pm, Sm, Eu, Gd, Tb, Dy, Ho, Er, Tm, Yb, and Lu. Eu is especially preferred.

In another embodiment, the targeting immunoreagent of this invention can comprise the ion of one or more paramagnetic elements which are suitable for the use in magnetic resonance imaging (MRI) applications. The paramagnetic element can be selected from elements of atomic number 21 to 29, 43, 44 and 57 to 71. The following elements are preferred: Cr, V, Mn, Fe, Co, Ni, Cu, La, Ce, Pr, Nd, Pm, Sm, Eu, Gd, Tb, Dy, Ho, Er, Tm, Yb and Lu. Ions of Mn, Gd, and Dy are especially preferred.

Another specifically contemplated embodiment of this invention comprises a targeting immunoreagent as described above comprising at least two metal ions in combination with one another in the same formulation, prepared as described above. For example, the use of a therapeutically effective dose of a radionuclide such as $^{90}Y^{+3}$ together with a diagnostic imaging effective dose of a paramagnetic ion such as $Gd^{+3}$, the ratio of the molar concentration of the diagnostic imaging effective ion to the molar concentration of the radionuclide ion being typically greater than one, in a pharmaceutically effective formulation of said targeting immunoreagent permits the simultaneous magnetic resonance imaging of at least a portion of the tissue of a host patient during therapeutic treatment of said patient.

In another embodiment of this invention, the use of radioisotopes of iodine is specifically contemplated. For example, if the targeting immunoreagent comprises a substituent that can be chemically substituted by iodine in a covalent bond forming reaction, such as, for example, a substituent containing hydroxyphenyl functionality, such a substituent can be labeled by methods well known in the art with a radioisotope of iodine. The thus covalently linked radioactive iodine species can be used in therapeutic and diagnostic imaging applications as described herein. In this embodiment, a preferred targeting immunoreagent comprises the antibody ING-1 covalently attached at a tyrosine site to an isotope of iodine and linked at a lysine amine site by a thiourea group formed as described above to the residue of chelating agent (21) which is chelated to $^{90}Y^{+3}$ ion.

In a preferred embodiment, an effective dose of a targeting radioactive immunoreagent as described above in a pharmaceutically acceptable medium is prepared by exposing a composition comprising a residue of an immunoreactive group as described above and a residue of a chelating agent having Structure I as described above linked to the immunoreactive group by a linking group as described above to a composition containing a radioactive metal ion as described above such that the molar amount of said radioactive metal ion in the composition is less than the molar amount of the chelating group comprising the targeting immunoreagent in said composition, the duration of the exposure lasting an effective time to permit uptake of said radioactive metal ion into said targeting immunoreagent. A preferred time is in the range of from 0.01 to two half lives of the radionuclide. For $^{90}Y^{+3}$, a preferred time is in the range of from 10 minutes to one hour.

In a preferred embodiment, an effective dose of a targeting immunoreagent as described above in a pharmaceutically acceptable medium is administered to a patient and said targeting immunoreagent is allowed to accumulate at the target site such as at a tumor site in said patient.

In a preferred embodiment, a therapeutically effective dose of a targeting radioactive immunoreagent as described above in a pharmaceutically acceptable medium is administered to a patient or to a tissue from a patient and said targeting radioactive immunoreagent is allowed to accumulate at the target site such as at a tumor site in said patient.

The present invention also comprises one or more targeting radioactive immunoreagents as described above formulated into compositions together with one or more non-toxic physiologically acceptable carriers, adjuvants or vehicles which are collectively referred to herein as carriers, for parenteral injection for oral administration in solid or liquid form, for rectal or topical administration, or the like.

The present invention also comprises one or more targeting paramagnetic immunoreagents as described above formulated into compositions together with one or more non-toxic physiologically acceptable carriers, adjuvants or vehicles which are collectively referred to herein as carriers, for parenteral injection, for oral administration in solid or liquid form, for rectal, or topical administration, or the like.

The compositions can be administered to humans and animals either orally, rectally, parenterally (intravenous, by intramuscularly or subcutaneously), intracisternally, intravaginally, intraperitoneally, intravesically, locally (powders, ointments or drops), or as a buccal or nasal spray. It is specifically contemplated that a targeting paramagnetic immunoreagent as described above and targeting radioactive immunoreagent as described above can be administered by the same route such as orally, rectally, parenterally (intravenous, by intramuscularly or subcutaneously), intracisternally, intravaginally, intraperitoneally, intravesically, locally (powders, ointments or drops), or as a buccal or nasal spray. It is also contemplated that a paramagnetic immunoreagent as described above can be administered by a route different from that of a targeting radioactive immunoreagent as described above.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated as being within the scope of this invention.

Actual dosage levels of active ingredients in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided dose may be in amounts, for example, of from about 1 nanomol to about 5 micromols per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

In another embodiment, the present invention is directed to a method of diagnosis comprising the administration of a diagnostic imaging effective amount of the compositions of the present invention as described above to a mammal or to a tissue from said mammal in need of such diagnosis. A method for diagnostic imaging for use in medical procedures in accordance with this invention comprises administering to the body of a test subject in need of a diagnostic image an effective diagnostic image producing amount of the above-described compositions. In this method, an effective diagnostic image producing amount of a radioactive targeting immunoreagent as described above in a pharmaceutically acceptable medium is administered to a patient and said radioactive targeting immunoreagent is allowed to accumulate at the target site such as at a tumor site in said patient. The image pattern can then be visualized, for example, by radioscintigraphy.

Alternatively, a patient or a specimen of a tissue of interest from a patient may be treated with a diagnostic imaging effective amount, i.e., a diagnostic imaging effective dose, of a targeting immunoreagent of this invention comprising a radionuclide as described above. This may be done by administering said dose to the environs of said tissue of interest of said patient or said specimen undergoing such diagnostic imaging, waiting for an effective period of time during which said immunoreagent will bind to sites on cells of said tissue of interest and during which time unbound immunoreagent will be removed from the environs of said tissue by circulation of a fluid such as blood in a patient or such as buffered saline solution in a sample of a tissue from a patient, and then obtaining an image as a function of time of all or part of said tissue of interest. When the image of all or part of said tissue of interest is optimal, a second dose comprising a therapeutically effective amount of targeting radioactive immunoreagent containing the same or a different radionuclide as that employed in the first dose of targeting radioactive immunoreagent is administered to said patient or to said tissue of interest of said patient.

In addition to human patients, the test subjects can include mammalian species such as rabbits, dogs, cats, monkeys, sheep, pigs, horses, bovine animals and the like.

After administration of a composition of the present invention, the subject mammal is maintained for a time period sufficient for the administered composition to be distributed throughout the subject and enter the tissues of the mammal. A sufficient time period is generally from about 1 hour to about 2 weeks or more and, preferably from about 2 hours to about 1 week.

EXAMPLES

The following examples further illustrate the invention and are not to be construed as limiting of the specification and claims in any way.

Example 1

2-Acetyl-6-Bromopyridine (2a)

To a solution of 2,6-dibromopyridine (0.75 mol) in 2000 ml of anhydrous ether, which was cooled to −60° C. under $N_2$, was added a solution of n-butyllithium in hexane (0.75 mol) over 15 min. The reaction mixture was cooled to −80° C. and a solution of dimethylacetamide (0.86 mol) in 70 ml anhydrous ether was added slowly over 1 hour. After stirring the mixture for 15 min, a solution of $NH_4Cl$ (0.93 mol) in 150 ml of water was added slowly over 8 min. After stirring an additional 45 min at room temperature, the aqueous layer was separated and extracted with 500 ml of ether. The combined organic layer was washed with water (2×800 ml), dried ($MgSO_4$), filtered, and stripped on a rotary evaporator to yield 159 g of the desired product. This material was distilled at 80° C./0.1 mm Hg to give a near colorless oil that crystallized readily on cooling.

Example 2

1-[2-(6-Bromo-2-pyridinyl)-2-oxoethyl]-pyridinium iodide (3a)

A mixture of 2-acetyl-6-bromopyridine (0.075 mol), 25 ml of pyridine, and iodine (0.075 mol) was allowed to react at 100° C. for 45 minutes and then cooled to room temperature. The reaction mixture was filtered, the solid product was triturated with $CH_2Cl_2$ (200 ml), isolated by filtration, and the residual solvent was removed under vacuum to yield 25.5 g (85%) of the desired salt. Melting point: 176–178° C.

Example 3

1-[2-(6-Bromopyridyl)]-3-(4-methoxyphenyl)-2-propen-1-one (4a)

To a stirred solution of 2-acetyl-6-bromopyridine (50 g; 0.25 mole) in 450 mL methanol was added 4-anisaldehyde (48 g; 0.35 mole). The mixture was cooled in a water bath to 20° C. and then a solution of KOH (18 g; 0.28 mole) in 100 mL $H_2O$ was added rapidly. The light yellow mixture was stirred for 30 minutes and filtered. The cake was rinsed twice with isopropanol, and, after drying, gave 68 g (86% yield). Melting point: 106.1–106.5° C. Mass spectrum (FDMS): 317 M+ (m/e).

Anal. for $C_{15}H_{12}BrNO_2$:

Calcd: C, 56.63; H, 3.80; N, 4.40. Found: C, 56.66; H, 3.87; N, 4.41.

Example 4

2-Acetylpyridine-N-Oxide (13)

To a solution of 2-acetylpyridine (0.3 mol) in 150 ml of glacial acetic acid was added with stirring 30% hydrogen peroxide (0.32 mol) and the mixture was allowed to react at 60–65° C. for 16 hours. An additional 3.3 ml of 30% hydrogen peroxide was added, and the mixture was allowed to react at 70° C. for 2 hours. After cooling, the water was removed by evaporation at reduced pressure to leave a crude liquid residue which was taken up in an equal volume of 50:50 ethyl acetate and hexane, and the components were separated by chromatography on 330 g of silica gel. Gradient elution starting with 50:50 ethyl acetate/hexane to 100% ethyl acetate and then to 5% methanol gave 13.48 g (33% yield) of 2-acetyl-pyridine-N-oxide. $^1$H NMR ($CDCl_3$): 2.81 (singlet (s), 3H, $CH_3$), 7.34 (multiplet (m), 2H, $H_4$ and $H_5$), 7.71 (doublet (d), 1H, $H_3$), and 8.22 ppm (d, 1H, $H_5$); $^{13}$C NMR ($CDCl_3$): 31.3 ($CH_3$), 125.9, 127.4, 128.6, 141.2, and 195.7 ppm (C=O); mass spectrum (DCl) M$^+$H=138 m/e; IR (film) $|_{max}$ 1686 cm$^{-1}$ (C=O).

Example 5

2-Acetyl-6-Cyanopyridine (14)

To a solution of 2-acetylpyridine-N-oxide (0.098 mol) in 200 ml of methylene chloride was added dimethylcarbamyl chloride (0.1 mol) and the reaction mixture was allowed to react at room temperature under nitrogen for 24 h. Additional dimethylcarbamyl chloride (0.1 mol) was added followed by cyanotrimethylsilane (0.22 mol), and the resulting mixture was allowed to react at 20° C. for 2 days. An additional 4 ml (0.03 mol) of cyanotrimethylsilane was then added, and the mixture was stirred at room temperature for another 24 hours. A solution of 200 ml of 10% $K_2CO_3$ was added to the reaction mixture and the resulting mixture was stirred for 45 min. The aqueous layer was extracted with 100 ml methylene chloride twice, the organic layers were combined and dried ($K_2CO_3$). After stripping the solvent, 16.9 g of crude product was isolated. The crude product obtained was chromatographed over Florisil" to isolate the desired products and the by-products with elution by the series of solvents: 2-acetyl-6-cyanopyridine (3a) (2 g, 50% $CH_2Cl_2$/hexane), 2-cyano-6-(1-cyano-1-trimethysilyloxy) ethylpyridine (3b) (0.81 g, $CH_2Cl_2$), 2-cyano-6-(1-cyano-1-dimethylcarbamoyloxy)ethylpyridine (3c) (1.67 g, 25:72 EtOAc/$CH_2Cl_2$), 2-(1-cyano-1-hydroxy)ethylpyridine (3d) (0.42 g, 50:50 EtOAc/$CH_2Cl_2$), and 2-(1-cyano-1-dimethylcarbamoyloxy)ethylpyridine-1-N-oxide (3e) (1.8 g, EtOAc). The products exhibited the following properties.

2-Acetyl-6-cyanopyridine (14)

$^1$H NMR ($CDCl_3$): 2.75 (s, 3H, $CH_3$); 7.9 (d, 1H); 8.05 (triplet (t), 1H); and 8.25 ppm (d, 1H).

$^{13}$C NMR ($CDCl_3$): 26.18 ($CH_3$); 117.23 (CN); 125.07; 131.89; 133.72; 138.84; 154.94 and 198.75 ppm (C=O).

MS (DCI) M+H=147 m/e.

IR ($CDCl_3$) $|_{max}$ 1709 cm$^{-1}$ (C=O) [2244 cm$^{-1}$, weak, C=N].

2-Cyano-6-(1-cyano-1-trimethylsilyloxy) ethylpyridine $^1$H NMR ($CDCl_3$): 0.3 (s, 9H, —$SiMe_3$); 1.96 (s, 3H, C—$CH_3$); 7.7 (d, 1H); 7.88 (d, 1H); and 7.95 ppm (two doublets, 1H).

$^{13}$C NMR ($CDCl_3$): 1.7 ($SiMe_3$); 31.08 (C—$CH_3$); 72.66 (quaternary C); 117.2 (CN); 120.8 (CN); 123.2; 128.7; 133.6; 139.1 and 162.5 ppm.

MS (DCI) M+H=246 m/e.

Combustion analysis for $C_{12}H_{15}N_3OSi$:

Calc'd: C, 58.74%; H, 6.16%; N, 17.13%. Found: C, 58.49%; H, 6.09%; N, 17.15%.

2-Cyano-6-(1-cyano-1-dimethylcarbamoyloxy) ethylpyridine $^1$H NMR ($CDCl_3$): 2.05 (s, 3H, C—Me); 2.89 and 3.03 (two singlets, 3H and 3H, —N—$Me_2$); 7.7 (m, 1H); and 7.94 ppm (m, 2H).

$^{13}$C NMR ($CDCl_3$): 28.37 (Me—C); 30.68 and 30.72 ( Me—N); 73.9 (quaternary C); 116.2 (CN); 118.4 (CN); 124.4; 128.78; 131.9 weak (wk); 134.1 (wk); and 138.91 ppm.

IR ($CDCl_3$)$|_{max}$ 1720 cm (C=O) (2247 cm$^{-1}$, wk, CN).

2-(1-Cyano-1-trimethylsilyloxy)ethylpyridine-1-N-oxide $^1$H NMR ($CDCl_3$): 3.0 (s, 3H, Me); 7.3 (m, 2H); 7.6 (d, 1H); and 8.2 ppm (d, 1H).

$^{13}$C NMR ($CDCl_3$): 0.1 (SiMe3); 27 (Me—C—); 124; 126.2; 126.5; 141; and 119 ppm (wk, CN).

IR ($CDCl_3$) no strong C=O absorption ($|_{max}$ ~2250$^{-1}$, wk, CN).

2-(1-Cyano-1-dimethylcarbamoyloxy)ethylpyridine-1-N-oxide $^1$H NMR ($CDCl_3$): 1.64 (broad singlet (bs), 1H); 2.23 (s, 3H, C—Me); 2.95 and 3.08 (two singlets, 3H and 3H, $Me_2$N—); 7.3 (m, 2H); 7.45 (m, 1H); and 8.24 ppm (m, 1H).

$^{13}$C NMR ($CDCl_3$): 24.2 (Me—C—); 37.0 and 37.3 ( $Me_2$N); 71.2 (quaternary C); 117.1 (CN); 124.0; 126.2; 126.4; and 141.3 ppm.

MS (DCI): M+H=226 (m/e).

IR ($CDCl_3$) $|_{max}$ 1729 cm$^{-1}$ [—OC(=O)$NMe_2$] ($|_{max}$ ~2250 cm$^{-1}$, wk, CN).

Example 6

1-[2-(6-Cyano-2-pyridyl)-2-oxoethyl]pyridinium Iodide (16)

To a mixture of 2-acetyl-6-cyanopyridine (1.78 mmol) and iodine (1.78 mmol) was added 2.6 ml of pyridine and the resulting mixture was allowed to react at 100° C. under $N_2$ for 45 min. The reaction mixture was cooled, the product was isolated by filtration, washed with $CH_2Cl_2$, and dried under vacuum to yield 0.485 g of pyridinium salt (78%). $^1$H NMR (DMSO-$D_6$): 3.35 (s, exchanges with $D_2O$), 6.5 (s, 2H, —$CH_2$), 8.25 to 8.5 (m, 5H), 8.75 (t, 1H), and 8.97 ppm (~d, 2H); $^{13}$C NMR DMSO-$D_6$: 66.75 (—$CH_2$—), 117.1 (CN), 125.94, 128.19, 132.4 (weak), 133.95, 140.82, 146.71, 146.91, 151.92 (weak), and 190.30 ppm (C=O).

Molecular formula: $C_{13}H_{10}IN_3O$;

Calculated: C, 44.46; H, 2.87; N, 11.96; I, 36.14; Found: C, 44.45; H, 2.75; N, 11.84; I, 36.27.

Example 7

1-[2-(6-cyanopyridyl)]-3-(4-methoxyphenyl)-2-propen-1-one (15a)

A mixture of 0.33 g of 2-acetyl-6-cyanopyridine, 0.28 mL of p-anisaldehyde, 1.9 g of basic alumina (activity grade I), and 6 mL of anhydrous tetrahydrofuran was stirred at room temperature under a nitrogen atmosphere for 24 hrs. The reaction mixture was filtered, and the solid product was rinsed with fresh tetrahydrofuran (5 ml). The filtrate was evaporated under reduced pressure to yield a yellow solid residue which weighed 0.6 g. The product was purified using silica gel chromatography, eluting with 35% hexane in methylene chloride, to yield 0.4 g (72%) of desired material. A sample for combustion analysis was isolated by vacuum sublimation at 130° C. and 0.01 mm. Melting point: 132.0 to 132.5° C. Mass spectrum: M+=264 m/e; IR (1% KBr): weak absorbance at $|_{max}$=2237 cm$^{-1}$ (CN), strong absorbance at 1670 cm$^{-1}$ (unsaturated C=O), as well as 1591, 1566, 1512, 1257, 1217, 1181, and 1042 cm$^{-1}$; $^1$H NMR (CDCl$_3$): 4.87 (s, 3H, —OMe), 6.96 (d, 2H, 2 ortho H's on phenyl), 7.71 (d, 2H, 2 other ortho H's on phenyl), 7.85–8.15 (complex multiplet, 4H, pyridyl and vinyl), and 8.4 ppm (d, 1H); $^{13}$C NMR (CDCl$_3$): 14 lines corresponding to 14 distinct carbons: 56.0, 115.1, 117.4, 126.3, 128.2, 131.4, 131.5, 133.3, 138.8, 146.7, 156.0, 162.8, and 187.7 ppm.

Combustion analysis for $C_{16}H_{12}N_2O_2$:

Calc'd: C, 72.71%; H, 4.58%; N, 10.60%. Found: C, 72.36%; H, 4.42%; N, 10.53%.

Example 8

1-[2-(2-pyridyl)-2-oxoethyl]pyridinium iodide, (3c)

To a stirred solution of 2-acetylpyridine (0.5 mole) in 600 mL pyridine is added iodine (127 g; 0.5 mole). The mixture is heated on a steam bath for 45 minutes, and the product crystallizes on cooling. The solid is filtered and the crystalline cake is rinsed twice with methylene chloride.

Example 9

1-[2-(2-Pyridinyl)-2-oxoethyl]pyridinium bromide, (3d)

2-Acetylpyridine (100 mmol) is treated with bromine (6.2 mL, 0.12 mol) at reflux in 200 mL of CHCl$_3$ for 45 min. The solution is cooled to room temperature then washed with dilute aqueous NaHCO$_3$/Na$_2$S$_2$O$_3$. The organic phase is dried over Na$_2$SO$_4$, filtered, and evaporated. The residue is dissolved in 200 mL of tetrahydrofuran (THF) and 30 mL of pyridine is added. The resulting solution is refluxed for 30 min. The mixture is cooled and filtered to give the desired product. The nuclear magnetic resonance (NMR) and infrared (IR) spectra are consistent with the assigned structure and the product is homogeneous by TLC.

Example 10

1-(2-Pyridyl)-3-(4-methoxyphenyl)-2-propenone, (4d)

To a stirred solution of p-anisaldehyde (144.5 g) in methanol (500 ml) cooled in an ice bath was added 2-acetylpyridine (113.8 g) in methanol (500 ml). To this solution was added a solution of potassium hydroxide (61.5 g) in water (250 ml) and methanol (200 ml), the reaction mixture was stirred for 4.5 hours. The reaction is allowed to stand at room temperature overnight. The precipitate is collected, washed with water and then with isopropanol, and dried under vacuum. The desired product was recrystallized from methanol (1300 ml) to give 190 g of material.

Example 11

1-[2-(6-Bromo-2-pyridinyl)-2-oxoethyl]-pyridinium bromide (3b)

2-Acetyl-6-bromopyridine from example 1 (20.0 g, 100 mmol) was treated with bromine (6.2 mL, 0.12 mol) at reflux in 200 mL of CHCl$_3$ for 45 min. The solution was cooled to room temperature then washed with dilute aqueous NaHCO$_3$/Na$_2$S$_2$O$_3$. The organic phase was dried over Na$_2$SO$_4$, filtered, and evaporated to give an oil. The oil was dissolved in 200 mL of tetrahydrofuran (THF) and 30 mL of pyridine was added. The resulting solution was refluxed for 30 min. The mixture was cooled and filtered to give 26.1 g of off-white powder (73% yield); mp 256° C. (decomposition; discolors at 245° C.). The nuclear magnetic resonance (NMR) and infrared (IR) spectra were consistent with the assigned structure and the product was homogeneous by TLC.

Analysis for $C_{12}H_{10}Br_2N_2O$:

Calculated: C, 40.26; H, 2.82; N, 7.82. Found: C, 40.12; H, 2.85; N, 7.79.

Example 12

1-[2-(6-Bromopyridyl)]-3-(4-nitrophenyl)-2-propen-1-one (4c)

This compound was prepared by the method of example 3 from 2-acetyl-6-bromopyridine (0.25 mole) in 450 mL methanol and 4-nitrobenzaldehyde (0.35 mole).

Example 13

1-[2-(6-Bromopyridyl)]-3-phenyl-2-propen-1-one (4b)

This compound was prepared by the method of example 3 from 2-acetyl-6-bromopyridine (0.25 mole) in 450 mL methanol and benzaldehyde (0.35 mole).

Example 14

1-[2-(6-cyanopyridyl)]-3-(4-nitrophenyl)-2-propen-1-one (15c)

This compound was prepared by the method of example 7 from 2-acetyl-6-cyanopyridine and 4-nitrobenzaldehyde.

Example 15

3-(4-Nitrophenyl)-1-(2-pyridyl)-2-propenone, (4f)

This compound was prepared by the method of example 10 from 2-acetylpyridine (60.6 g), 4-nitrobenzaldehyde (106

Example 16

1-(2-Pyridyl)-3-phenyl-2-propenone, (4e)

This compound was prepared by the method of example 10 from 2-acetylpyridine and benzaldehyde.

Example 17

6-cyano-4'-(4-methoxyphenyl)-2,2':6';2"-terpyridine (9a)

A mixture of 2-acetyl-6-cyanopyridine pyridinium iodide (5 mmol), 1-(2-pyridyl)-3-(4-methoxyphenyl)-2-propenone (5 mmol), ammonium acetate (25 mmol) and 10 ml glacial acetic acid was stirred with heating for 5 minutes to 80° C., then at 60° C. for 6 hrs, and then at ambient temperature for 12 hrs. After cooling in an ice water bath, 1.5 g of solid was removed by filtration, and the filtrate was evaporated. 6-Cyano-4'-(4-methoxyphenyl)-2,2':6',2"-terpyridine was extracted from the combined residues by successive triturations with ethyl ether and ethyl acetate to give, after evaporation of the solvents, 0.7 g of product (40% yield).

Example 18

6-Aminomethyl-4'-(4-methoxyphenyl)-2,2':6';2"-terpyridine (10a)

6-Cyano-4'-(4-methoxyphenyl)-2,2':6',2"-terpyridine (1 mmol) in 33 ml of glacial acetic acid was reduced with hydrogen in the presence of 0.1 g of 10% palladium catalyst on carbon in a Parr apparatus at 40–50 psi and 40–45° C. for three days. The catalyst was removed by filtration under nitrogen, and the product was purified using a silica gel column by elution with 2.5% ammonium hydroxide/5% methanol/92.5% methylene chloride to yield 0.24 g (65%) of product as a hemi-hydrate.

1H NMR (CDCl$_3$): 1.87 (singlet (s), exchanges with D$_2$O); 3.90 (s, 3H, MeO—); 4.12 (s, 2H, terpyridyl-CH$_2$—N), 7.08 (doublet (d), 2H, phenyl); 7.35 (multiplet (m), 2H); 7.90 (m and d, 4H); 8.55 (d, 1H); and 8.70 ppm (m, 4H).

Calculated: C, 73.19%; H 5.61%; N, 14.84%. Found: C, 72.95%; H, 5.43%; N, 14.61%.

Example 19

6-cyano-4'-(4-nitrophenyl)-2,2':6';2"-terpyridine (9c)

A mixture of 1-[2-(6-cyano-2-pyridyl)-2-oxoethyl]pyridinium iodide (1 mmol), 3-(4-nitrophenyl)-1-(2-pyridyl)-2-propenone (1 mmol) and ammonium acetate (5 mmol) in 4 ml of glacial acetic acid was heated with stirring to 80° C. for 20 minutes, then at 60° C. for 3 hrs, and then 20° C. for 18 hrs. The reaction mixture was cooled to 5° C. to give a tan solid which was triturated with water five times, isolated by filtration, and then dried. Yield: 0.297 g (78%).

Example 20

6-Aminomethyl-4'-(4-nitrophenyl)-2,2':6';2"-terpyridine (10c)

To a cold (ice bath) solution of 6-cyano-4'-(4-nitrophenyl)-2,2':6',2"-terpyridine (1 mmol) in 3 ml anhydrous tetrahydrofuran containing sodium borohydride (0.2 mmol) was added, dropwise, 1.1 ml of 1 M diborane in tetrahydrofuran solution. After the addition was completed, the reaction mixture was stirred at ambient temperature for 1 hour and then at 33° C. for 2 hrs. The reaction mixture was chilled in an ice bath, and 1.25 ml of 2N HCl was carefully added. The reaction mixture was stirred for 2 hours and allowed to warm to room temperature. The crude product was isolated by filtration and then purified on silica gel eluting with 2.5% NH$_4$OH/5% MeOH/92.5% CH$_2$Cl$_2$. Yield: 0.21 g (55%) as a 1/3 hydrate. $^1$H NMR (CDCl$_3$): 4.1 (s, 2H: —CH$_2$NH$_2$); 7.38 (m, 2H); 7.91 (m, 2H); 8.08 (d, 2H, phenyl); 8.4 (d, 2H, phenyl); 8.58 (d, 1H); 8.7 (d, 1H) and 8.77 ppm (m, 3H). Mass spectrum (DCI): M+H=384 m/e.

Calculated: C, 67.86%; H, 4.49%; N, 17.98%. Found: C, 67.60%; H, 4.37%; N, 17.60%.

Example 21

3,9-Bis{N-6-[4'-(4-methoxyphenyl)-2,2':6',2"-terpyridylmethyleneazacarbonylmethyl]}-6-carboxymethyl-3,6,9-triaza-1,11-undecanedioic acid (19a)

A mixture of 6-aminomethyl-4'-(4-methoxyphenyl)-2,2':6',2"-terpyridine (0.14 mmol), diethylenetriaminepentaacetic acid dianhydride (0.14 mmol), and triethylamine (0.05 ml) in 1.5 ml of anhydrous dimethylformamide was stirred for 1¾ hrs at 0° C. and then ¼ hr at room temperature. The solvent was evaporated at reduced pressure to yield a residue weighing 0.123 g. A portion (0.1 g) of this residue was triturated with 20% methanol in methylene chloride four times to yield 86 mg of desired product as a heptahydrate.

$^1$H NMR (DMSO-D$_6$): [2.83 (m, 4H); 2.90 (m, 4H); 3.4 (m, exchanges with D$_2$O), all diethylenetriamine moiety]; 4.50 (broad s, 4H, terpyridyl-6-CH$_2$—NH—CO—); [3.80 (s, 6H, CH$_3$O—); 7.07 (d, 4H, phenyl); 7.34 (d, 2H); 7.46 (m, 2H); 7.77 (d, 4H, phenyl); 7.90 (2t, 4H); 8.4 (d, 2H); 8.54 (d of d, 4H); 8.69 (d, 2H) and 8.83 ppm (m, 2H, exchanged), all bisterpyridyl moiety].

Calculated: C, 59.05%; H, 6.06%; N, 12.63%. Found: C, 58.89%; H, 6.16%; N, 13.18%.

Example 22

3,9-Bis{N-6-[4'-(4-nitrophenyl)-2,2':6',2"-terpyridylmethyleneazacarbonylmethyl]}-6-carboxymethyl-3,6,9-triaza-1,11-undecanedioic acid (19c)

A solution of 6-aminomethyl-4'-(4-nitrophenyl)-2,2':6', 2"-terpyridine (1 mmol), diethylenetriaminepentaacetic dianhydride (0.5 mmole), and 0.2 ml of triethylamine in 10 ml of anhydrous dimethylformamide was stirred at 0° C. for 1½ hr, and then at room temperature for ½ hr. The solvent was removed from the reaction mixture at reduced pressure to leave a residue (0.65 g) which was treated with 6 ml of 20% methanol in methylene chloride and then filtered. The solvent in the filtrate was removed by rotary evaporation to yield 0.60 g of solid. Unreacted 6-aminomethyl-4'-(4-nitrophenyl)- 2,2':6',2"-terpyridine was removed by successive triturations with chloroform, hot ethyl acetate, and hot acetone to leave the desired product as a pentahydrate. Yield: 0.42 g (75%). $^1$H NMR (CD$_3$OD): 2.95 (broad s, 4H); 3.1 (s, 4H); 3.4 (d and broad s, 10H); 3.97 (s, 2H); 4.35 (s, 4H, —CO—NH—CH$_2$-terpyridyl); 4.5 (large s, exchanged with D$_2$O); 7.08 (d, 2H); 7.3 (m, 2H); 7.58 (t, 2H); 7.68 (d, 4H, phenyl); 7.8 (m, 2H); 8.01 (d, 4H, phenyl); 8.2 (d and s, 4H);

Example 23

1-[1-(3-Methylimidazolium)]glycine-N,N-bis (ethylene-2-iminodiacetic acid anhydride) trifluoromethanesulfonate (25)

To a stirred solution of 1,1'-carbonyldiimidazole (162 mg) in anhydrous nitromethane (2 ml) under nitrogen and cooled to 0° C. was added, dropwise, 0.225 ml of methyl trifluoromethanesulfonate (methyltriflate). After 20 minutes at 0° C., the reaction mixture was added to a solution of diethylenetriaminepentaacetic acid dianhydride (357 mg) in anhydrous dimethylformamide (3 ml). This reaction mixture was stirred at room temperature under nitrogen for one half hour to provide a solution of the desired compound, 25.

Example 24

3,9-Bis(carboxymethyl)-6-{6-[4'-(4-nitrophenyl)-2,2':6',2"-terpyridyl]methylaminocarbonylmethyl}-3,6,9-triazaundecanedioic acid (26)

To a solution of 1-[1-(3-methylimidazolium)]-glycine-N,N-bis(ethylene-2-iminodiacetic acid anhydride) trifluoromethanesulfonate prepared in example 23 was added 6-aminomethyl-4'-(4-nitrophenyl)-2,2':6',2"-terpyridine (193 mg). The reaction mixture was stirred under a nitrogen atmosphere at 0° C. for 90 minutes, and then for 90 minutes at ambient temperature. One milliliter of water was added, and the reaction mixture was then stirred at room temperature for one half hour. The solvent was evaporated under reduced pressure to leave a glassy residue which was triturated twice with water. After filtration and washing with water, the product was dried by azeotropic removal of water in toluene. The crude reaction product (0.5 g) was isolated by filtration and then further purified chromatographically on silica gel using a step gradient of (a) 15% methanol in methylene chloride followed by elution with (b) 5% ammonium hydroxide/20% methanol/75% methylene chloride, and finally (c) 10% ammonium hydroxide and 40% methanol in methylene chloride. The desired compound was in the later fractions. Solvent removal provided the desired compound. Yield: 76 mg, (20%). Mass spectrum: MH+759 (molecular formula: $C_{36}H_{38}N_8O_{11}$). $^1H$ NMR (DMSO-$d_6$): 2.85 (broadened triplet, 8 H, —NC$\underline{H}_2$C$\underline{H}_2$N—); 3.3 (3 merging singlets centered at 3.3 ppm, 10 H, —NC$\underline{H}_2$CO$_2$— and —COC$\underline{H}_2$N—); 3.6 (very broad, —CO$_2$H and H$_2$O); 4.57 (s, 2H, terpyridyl-6-C$\underline{H}_2$N—); 7.47 (d, 1H, terpyridyl-4-H); 7.52 (t/m, 1 H, terpyridyl-4"-H); 8.05 (M, 2 H, terpyridyl-3-H and terpyridyl-5-H); 8.20 (d, 2 H, nitrophenyl); 8.41 (d, 2 H, nitrophenyl); 8.5 (d, 1 H, terpyridyl-5"-H); 8.66 (d, 1 H, terpyridyl-6 H); 8.7 and 8.73 ppm (s and m, 3 H, terpyridyl-3-H, terpyridyl-3"-H and terpyridyl-3' and terpyridyl-5'-H).

Example 25

Eu$^{+3}$ complex of 3,9-bis(carboxymethyl)-6-{6-[4'-(4-nitrophenyl)-2,2':6',2"-terpyridyl]-methylaminocarbonylmethyl}-3,6,9-triazaundecanedioic acid A 0.01 N sodium acetate aqueous solution at pH 6 containing 3,9-bis(carboxymethyl)-6-{6-[4'-(4-nitrophenyl)-2,2':6',2"-terpyridyl]methylaminocarbonylmethyl}-3,6,9-triazaundecanedioic acid of example 24 was treated with EuCl$_3$, and the progress of the reaction was followed by UV spectroscopy. Uptake of Eu by the chelate was complete within 5 minutes.

Example 26

6-Bromo-4'-(4-nitrophenyl)-2,2':6',2"-terpyridine (5c)

A slurried mixture of 3-(4-nitrophenyl)-1-(2-pyridyl)-2-propenone (1.27 g), 1-[2-(6-bromo-2-pyridinyl)-2-oxoethyl]-pyridinium iodide (2.03 g), ammonium acetate (1.93 g) and glacial acetic acid (15 ml) was stirred under argon and heated to 94° C. for 90 minutes and then at 67° C. for 16 hours. The reaction mixture was poured into water (125 ml) and the solid product (1.74 g) was isolated by filtration, washed with water, and dried. The solid was dissolved in ethyl acetate at room temperature (200 ml/g) and the solution was filtered through a 2×5 cm pad of silica gel. The silica gel was rinsed with 100 ml of ethyl acetate, and the solvent was evaporated to leave the desired product which was purified by flash chromatography on silica gel using ethyl acetate.

Example 27

6-Cyano-4'-(4-nitrophenyl)-2,2':6',2"-terpyridine (9c)

A mixture of 6-bromo-4'-(4-nitrophenyl)-2,2':6',2"-terpyridine (5.63 g), cuprous cyanide (4.66 g), sodium cyanide (2.55 g), and dimethylformamide (35 ml) was heated under argon with stirring to 160° C. for 4.5 hours, cooled to room temperature, and treated with 175 of water. After 15 min, the resulting slurry was filtered, the dark brown paste so obtained was placed in water (85 ml) containing sodium cyanide (3.2 g), and the reaction mixture was stirred for 15 minutes. The solid product was isolated by filtration, washed with water and dried under vacuum. Yield: 4.38 g.

Example 28

6-Bromo-4'-(4-methoxyphenyl)-2,2':6',2"-terpyridine (5a)

A slurried mixture of 3-(4-methoxyphenyl)-1-(2-pyridyl)-2-propenone (239 mg), 1-[2-(6-bromo-2-pyridinyl)-2-oxoethyl]-pyridinium iodide (405 mg), ammonium acetate (386 mg) and glacial acetic acid (3 ml) was stirred under argon and heated to 94° C. for 120 minutes and then at 60° C. for 16 hours. The reaction mixture was cooled at 0° C. overnight, filtered, and the solid product was washed with water, and dried. Yield 0.2 g (48%).

Example 29

6-Cyano-4'-(4-methoxyphenyl)-2,2':6',2"-terpyridine (9a)

6-Cyano-4'-(4-methoxyphenyl)-2,2':6',2"-terpyridine is prepared by the method of example 27 from 6-bromo-4'-(4-methoxyphenyl)-2,2':6',2"-terpyridine (0.0745 mol), cuprous cyanide (0.296 mol), sodium cyanide (0.297 mol), and dimethylformamide (300 ml).

Example 30

6-aminomethyl-4'-(4-methoxyphenyl)-2,2':6',2"-terpyridine (10a)

A mixture of 6-cyano-4'-(4-methoxyphenyl)-2,2':6',2"-terpyridine (4 mmol) and 480 mg of 10% Pd/C in 130 ml of acetic acid is hydrogenated ($H_2$, 50 psi) at 45° C. for 22 hours. The reaction mixture is filtered and the solvent is stripped, the residue is triturated with methanol, filtered and dried to provide the desired product as the acetic acid salt.

Example 31

6-[N,N-di-(carboxymethyl)aminomethyl)-4'-(4-methoxyphenyl)-2,2':6'2"-terpyridine (29a)

A mixture of 6-aminomethyl-4'-(4-methoxyphenyl)-2,2':6',2"-terpyridine (1.13 mmol), t-butyl bromoacetate (4.65 mmol), and $K_2CO_3$ (1.2 mmol) in dimethylformamide is allowed to react at 85° C. for 60 hours. After an addition of $K_2CO_3$ (4.65 mmol), the reaction mixture was allowed to react at 85° C. for 20 hours. The reaction mixture is filtered and DMF is distilled under diminished pressure to provide a residue containing crude amino ester. The crude product is triturated with water, extracted with ethyl acetate, and dried. Upon distillation of ethyl acetate, the desired amino-ester is isolated, treated with sodium hydroxide to saponify the esters and provide the sodium salt of the desired acid. This was titrated with hydrochloric acid to provide the desired acid which was isolated by lyophilization of the solution.

Example 32

4'-(4-Methoxyphenyl)-2,2':6'2"-terpyridine-6-carboxaldehyde (6a)

A solution of 6-bromo-4'-(4-methoxyphenyl)-2,2':6',2"-terpyridine (15.1 mmol) in 100 mL of dry THF is added dropwise to a solution of n-butyl lithium (15.5 mmol) in 20 mL of tetrahydrofuran (THF) at –78° C. under $N_2$ over 12 minutes. After 10 minutes the reaction mixture is treated with dimethylformamide (7.5 mL) in THF (15 mL), and quenched after 15 minutes with aqueous 10% HCl. The product is extracted into cold chloroform which is washed with saturated sodium chloride solution, filtered, and the solvent is evaporated. The residue is triturated with $CH_3CN$, filtered, and recrystallized from ethyl acetate to provide the desired compound.

Example 33

6-Hydroxymethyl-4'-(4-methoxyphenyl)-2,2':6',2"-terpyridine (7a)

A suspension of 4'-(4-methoxyphenyl)-2,2':6'2"-terpyridine-6-carboxaldehyde (8.93 mmol) in a mixture of 70 mL of THF and 70 mL of absolute EtOH is treated with 1 g of $NaBH_4$ and then heated to reflux for 15 minutes under $N_2$. After cooling, the organic solvents are removed, the residue is heated for 30 minutes at reflux in dilute $NaHCO_3$, cooled, filtered, washed with $H_2O$, then dried to give the desired product.

Example 34

6-Hydroxymethyl-4'-(4-methoxyphenyl)-2,2':6',2"-terpyridine Methanesulfonate (8a)

To a suspension of 6-hydroxymethyl-4'-(4-methoxyphenyl)-2,2':6',2"-terpyridine (38.5 mmol) in $CH_2Cl_2$ (175 mL) and $Et_3N$ (50 mmoles) at 8° C. is added a solution of $(CH_3SO_2)_2O$ (48 mmol) in 50 mL of $CH_2Cl_2$ over 10–15 minutes. The reaction mixture is then extracted with cold water, dried over $Mg_2SO_4$, filtered, and concentrated under high vacuum nearly to dryness. The residue is treated with ethyl acetate, and the desired product is collected by filtration, washed with ethyl acetate, and dried under vacuum.

Example 35

6-[N,N-di-(carboxymethyl)]aminomethyl-4-(4-methoxyphenyl)-2,2':6'2"-terpyridine Diethyl Ester (51a)

A mixture of 6-hydroxymethyl-4'-(4-methoxyphenyl)-2,2':6',2"-terpyridine methanesulfonate (0.96 mmol), di-isopropylethylamine (1.0 mmol), and diethyl iminodiacetate (1.0 mmol) is stirred for 16 hours in 20 mL of dry dimethylformamide. The solvent is evaporated under vacuum, and the residue is partitioned between equal volumes of ether and water. The ether is washed twice with water, dried over $Na_2SO_4$ and evaporated to give the desired product.

Example 36

6-[N,N-di-(carboxymethyl)]aminomethyl-4'-(4-methoxy-3-nitrophenyl)-2,2':6'2"-terpyridine Diethyl Ester (52a)

A solution of 6-[N,N-di-(carboxymethyl)]-aminomethyl-4'-(4-methoxyphenyl)-2,2':6'2"-terpyridine diethyl ester (40.6 mmoles) in trifluoroacetic acid (160 mL) at 15° C. is treated with potassium nitrate (44 mmoles) followed by concentrated $H_2SO_4$ (230 mmoles) added dropwise over 15 minutes. After 30 minutes the trifluoroacetic acid is recovered by distillation under reduced pressure, the residue is cooled, poured onto crushed ice, and treated with aqueous 10% $K_2CO_3$ until pH 8 is reached. The aqueous solution is extracted three times with ethyl acetate, the combined organic layers are washed with water, then with saturated sodium chloride solution, are dried over $Na_2SO_4$, filtered, and concentrated to near dryness. The residue is taken up in 90 mL of hot absolute ethanol, and the solution is allowed to cool. The desired product is collected by filtration, rinsed with ethanol, and dried under vacuum.

Example 37

6-[N,N-di-(carboxymethyl)]-aminomethyl-4'-(3-amino-4-methoxyphenyl)-2,2':6'2"-terpyridine Diethyl Ester (53a)

A mixture of 6-[N,N-di-(carboxymethyl)]-aminomethyl-4'-(4-methoxy-3-nitrophenyl)-2,2':6'2"-terpyridine diethyl ester (36 mmoles) and 10% Pd/C (10 mmoles) in THF (350 mL) and absolute ethanol (350 mL) under argon is treated with a solution of ammonium formate (9.4 g; 149 mmoles) in water (60 ml) over five minutes. The reaction mixture is stirred for 3 hours at reflux, cooled to 20° C., filtered, the catalyst is washed with 400 mL of absolute ethanol, and the filtrate is evaporated to dryness under vacuum to give the crude product which is further purified on silica gel with 10% $MeOH/CHCl_3$.

Example 38

6-[N,N-di-(carboxymethyl)]-aminomethyl-4'-(3-amino-4-methoxyphenyl)-2,2':6'2"-terpyridine, disodium salt (54a)

A mixture of 6-(N,N-di-(carboxymethyl)]-aminomethyl-4'-(3-amino-4-methoxyphenyl)-2,2':6'2"-terpyridine diethyl ester (0.99 mmol), sodium hydroxide (4 mmol), methanol (50 mL), and triply distilled water (2 mL) is stirred for 16 hours at room temperature. Most of the solvent is removed under vacuum, the solid is isolated by filtration, rinsed twice with cold ethanol and once with hexane to give the desired product.

Example 39

6-[N,N-di-(carboxymethyl)]-aminomethyl-4'-(3-isothiocyanato-4-methoxyphenyl)-2,2':6'2"-terpyridine, disodium salt (55a)

To a solution of 6-[N,N-di-(carboxymethyl)]-aminomethyl-4'-(3-amino-4-methoxyphenyl)-2,2':6'2"-terpyridine disodium salt (0.50 mmol) in 80 mL of methanol at room temperature is added 0.58 g (0.50 mmol) of thiophosgene in 1.0 mL tetrahydrofuran followed by 0.51 g (0.50 mmol) of triethylamine in 1.0 mL of tetrahydrofuran. The reaction mixture is then concentrated under vacuum to leave a residue to which dichloromethane is added. The desired product is isolated by filtration, washed with dichloromethane and dried under vacuum.

Example 40

4'-(4-methoxyphenyl)-2,2':6'2"-terpyridine-6-carboxylic acid (11a)

A flame dried 3 necked 1 L flask equipped with a mechanical stirrer, pressure equalizing addition funnel, and, attached via silicone rubber tubing, a Gooch tube containing solid 6-bromo-4'-(4-methoxyphenyl)-2,2':6'2"-terpyridine (42.2 mmole) under nitrogen is charged with 400 mL THF and cooled in a Dry Ice/ether bath to −78° C. A solution of n-butyllithium (20 mL of 2.5 M) is transferred via nitrogen pump to the pressure equalizing addition funnel, and is then added to the THF solution. After stirring 15 minutes at −78° C., the solid 6-bromo-4'-(4-methoxyphenyl)-2,2':6'2"-terpyridine is added portionwise over an 11 minute period from the Gooch tube. The temperature is not allowed to exceed −75° C. during the addition. After the addition, the bath is lowered, and the reaction mixture is allowed to warm slightly to −70° C. over a 10 minute period. The solution is re-cooled to −78° C., and the reaction mixture is transferred via cannula under nitrogen to a jacketed addition funnel cooled to −78° C. This anionic solution is maintained at −78° C. under nitrogen while it is added with stirring to 400 mL of THF saturated with anhydrous carbon dioxide in a 3 liter 3 necked flask attached to a silicone oil bubbler. Additional anhydrous carbon dioxide is slowly bubbled into the reaction mixture during the addition while the temperature is carefully controlled to remain below −70° C. After stirring for 60 minutes, the cooling bath is removed and the reaction mixture is carefully quenched with 100 ml of a 1 N aqueous HCl solution over a ten minute period. The reaction mixture is allowed to stir and warm to room temperature. The solvent is evaporated under vacuum below 20° C., the crude product is triturated with isopropanol, isolated by filtration, washed with ether and dried under vacuum.

Example 41

4'-(4-methoxyphenyl)-2,2':6'2"-terpyridine-6-carbonyl chloride (12a)

To 1 g of 4'-(4-methoxyphenyl)-2,2':6'2"-terpyridine-6-carboxylic acid is added a solution of 1 mL of thionyl chloride in 25 mL of methylene chloride. The reaction mixture is heated gently for 1 hour, and the solvent and excess thionyl chloride are removed under reduced pressure. The crude product is triturated with anhydrous heptane and isolated by filtration under nitrogen.

Example 42

3,9-Bis{N-6-[4'-(4-aminophenyl)-2,2':6',2"-terpyridylmethyleneazacarbonylmethyl]}-6-carboxymethyl-3,6,9-triaza-1,11-undecanedioic acid (57)

A mixture of 3,9-bis{N-6-[4'-(4-nitrophenyl)-2,2':6',2"-terpyridylmethyleneazacarbonylmethyl]}-6-carboxymethyl-3,6,9-triaza-1,11-undecanedioic acid (1 mmol) and 10% Pd/C (10 mmoles) in THF (350 mL) and absolute ethanol (350 mL) under argon is treated with a solution of ammonium formate (9.4 g; 149 mmoles) in water (60 ml) over five minutes. The reaction mixture is stirred for 3 hours at reflux, cooled to 20° C., filtered, the catalyst is washed with 400 mL of absolute ethanol, and the filtrate is evaporated to dryness under vacuum to give the desired product.

Example 43

3,9-Bis{N-6-[4'-(4-isothiocyanatophenyl)-2,2':6',2"-terpyridylmethyleneaza-carbonylmethyl]}-6-carboxymethyl-3,6,9-triaza-1,11-undecanedioic acid (58)

To a solution of 3,9-bis{N-6-[4'-(4-aminophenyl)-2,2':6',2"-terpyridylmethyleneaza-carbonylmethyl]}-6-carboxymethyl-3,6,9-triaza-1,11-undecanedioic acid (0.50 mmol) in 80 mL of methanol at room temperature is added 1.18 g (1.0 mmol) of thiophosgene in 2.0 mL tetrahydrofuran followed by 2.02 g (1.0 mmol) of triethylamine in 2.0 mL of tetrahydrofuran. The reaction mixture is then concentrated under vacuum to leave a residue to which dichloromethane is added. The desired product is isolated by filtration, washed with dichloromethane and dried under vacuum.

Example 44

3,9-Bis(carboxymethyl)-6-{6-[4'-(4-aminophenyl)-2,2':6',2"-terpyridyl]methylaminocarbonylmethyl}-3,6,9-triazaundecanedioic acid, tetrasodium salt (59)

A mixture of 3,9-bis(carboxymethyl)-6-{6-[4'-(4-nitrophenyl)-2,2':6',2"-terpyridyl]methylaminocarbonylmethyl}-3,6,9-triazaundecanedioic acid (26) (0.1 mmol), sodium hydroxide (0.4 mmol of 1N) and 10% Pd/C (1 mmol) in water (15 mL) and absolute ethanol (15 mL) under argon is treated with a solution of ammonium formate (0.94 g; 14.9 mmoles) in water (6 ml) over five minutes. The reaction mixture is stirred for 3 hours at reflux, cooled to 20° C., filtered, the catalyst is washed with 20 mL of water, and the filtrate is evaporated to dryness under vacuum to give the desired product.

Example 45

3,9-Bis(carboxymethyl)-6-{6-[4'-(4-isothiocyanatophenyl)-2,2':6',2"-terpyridyl]methylaminocarbonylmethyl}-3,6,9-triazaundecanedioic acid, tetrasodium salt (60)

To a solution of 3,9-bis(carboxymethyl)-6-{6-[4"-(4-aminophenyl)-2,2':6',2"-terpyridyl]methylaminocarbonylmethyl}-3,6,9-triazaundecanedioic acid tetrasodium salt (59) (0.50 mmol) in 80 mL of methanol at room temperature is added 0.58 g (0.50 mmol) of thiophosgene in 1.0 mL tetrahydrofuran followed by 0.51 g (0.50 mmol) of triethylamine in 1.0 mL of tetrahydrofuran. The reaction mixture is then concentrated under vacuum to leave a residue to which dichloromethane is added. The desired product is isolated by filtration, washed with dichloromethane and dried under vacuum.

Example 46

Conjugation of 3,9-Bis(carboxymethyl)-6-{6-[4'-(4-isothiocyanatophenyl)-2,2':6',2"-terpyridyl]methylaminocarbonylmethyl}-3,6,9-triazaundecanedioic acid, tetrasodium salt (60) to ING-1 antibody ING-1, a chimeric antibody, (50 nmoles) is allowed to react with 3,9-bis(carboxymethyl)-6-{6-[4'-(4-isothiocyanatophenyl)-2,2':6',2"-terpyridyl]methylaminocarbonylmethyl}-3,6,9-triazaundecanedioic acid, tetrasodium salt, (60), of example 45 (250 nmoles in 1.0 M carbonate, 150 mM sodium chloride buffer, pH 9.3 in an acid washed, conical, glass reaction vial. The solution is stirred briefly to mix the reactants and then left in the dark at room temperature. After 16 hours, the ING-1/chelating agent conjugate is separated from unconjugated chelator by applying the reaction mixture to a PD-10 chromatography column (Pharmacia) which is pre-washed and equilibrated with 50 mM sodium acetate buffer containing 150 mM sodium chloride at pH 5.6. The pure ING-1/3,9-bis(carboxymethyl)-6-{6-[4'-(4-isothiocyanatophenyl)-2,2':6',2"-terpyridyl]methylamino-carbonylmethyl}-3,6,9-triazaundecanedioic acid, tetrasodium salt conjugate is eluted off the column with 2.5 mL of that same buffer, and concentrated on a Centricon-10® concentration device.

Example 47

Radiolabeling of ING-1/3,9-bis(carboxymethyl)-6-{6-[4'-(4-isothiocyanatophenyl)-2,2':6',2"-terpyridyl]methylaminocarbonylmethyl}-3,6,9-triazaundecanedioic acid, tetrasodium salt conjugate with $^{90}Y^{+3}$ A volume of radioactive yttrium chloride ($^{90}Y$ in 0.04 M hydrochloric acid at a specific activity of >500 Ci/g: Amersham-Mediphysics) is neutralized using two volumes of 0.5 M sodium acetate pH 6.0. The neutralized $^{90}Y$ (1.0 mCi) is added to 1.0 mL of ING-1/3,9-bis(carboxymethyl)-6-{6-[4'-(4-isothiocyanatophenyl)-2,2':6',2"-terpyridyl]methylamino-carbonylmethyl}-3,6,9-triazaundecanedioic acid, tetrasodium salt conjugate of example 46 (1 mg/mL) in 50 mM sodium acetate buffer containing 150 mM sodium chloride at pH 5.6. The labeling is allowed to proceed for one hour, and then the reaction mixture is loaded onto a PD-10 chromatography column which is pre-washed and equilibrated in a buffer containing 50 mM sodium phosphate with 150 mM sodium chloride pH 7.4 (PBS). The sample is eluted from the column with 1.5 mL of PBS. Fractions of radiolabeled ING-1/3,9-bis(carboxymethyl)-6-{6-[4'-(4-isothiocyanatophenyl)-2,2':6',2"-terpyridyl]methylamino-carbonylmethyl}-3,6,9-triazaundecanedioic acid, tetrasodium salt conjugate (0.5 mL) are collected, assayed for radioactivity, and pooled. The labeling efficiency is determined by removing 1.0 uL of the sample and spotting it on to a Gelman ITLC-SG strip. The strip is developed in a glass beaker containing 0.1 M sodium citrate, pH 6.0, for a few minutes until the solvent front has reached three-quarters of the way to the top of the paper. The strip is inserted into a System 200 Imaging Scanner (Bioscan) which has been optimized for $^{90}Y$ and is controlled by a Compaq 386/20e computer. In this system, free $^{90}Y$ migrates at the solvent front while the ING-1/3,9-bis(carboxymethyl)-6-{6-[4'-(4-isothiocyanatophenyl)-2,2':6',2"-terpyridyl]methylaminocarbonylmethyl}-3,6,9-triazaundecanedioic acid, tetrasodium salt conjugate containing $^{90}Y$ remains at the origin. Using this system, more than 98% of the total $^{90}Y$ radioactivity is found associated with ING-1/3,9-bis(carboxymethyl)-6-{6-[4'-(4-isothiocyanatophenyl)-2,2':6', 2"-terpyridyl]methylamino-carbonylmethyl}-3,6,9-triazaundecanedioic acid, tetrasodium salt conjugate at the origin.

Example 48

Antibody Protein Concentration

The concentrations of ING-1 for use in the conjugate reactions are determined by the BioRad protein assay (BioRad Catalog #500-0001) using bovine immunoglobulin as the protein standard.

Example 49

Immunoreactivity Assay by Flow Cytometry

Conjugates of antibody and chelates such as those of ING-1 in examples 46 and 47 are examined for their ability to bind to antigens on the surface of a human tumor cell line to which the antibody had been raised. The immunoreactivity of the conjugates is compared by flow cytometry with a standard preparation of the antibody before being subjected to modification. Target HT-29 cells (a human adenocarcinoma cell line obtained from the American Type Tissue Collection: ATTC) are grown to confluency in tissue culture flasks using McCoy's media supplemented with 10% fetal calf serum. The cells are harvested by scraping the flask walls with a cell scraper. Cells from many separate flasks are pooled, centrifuged to a pellet, resuspended at $5 \times 10^5$/mL in a solution of ice-cold 5 mM sodium phosphate with 150 mM sodium chloride buffer, pH 7.4, (PBS) supplemented with 0.1% bovine serum albumin (Sigma) and 0.02% sodium azide (Flow buffer). The cells are washed in this same buffer and then counted. An antibody standard curve is constructed by diluting a stock solution of ING-1 with an irrelevant (non-binding), isotype-matched control antibody, [human $IgG_1$], to give a number of samples ranging in ING-1 content from 10% to 100%. The standard curve is made in flow buffer so that each sample contains 1.0 mg/mL of protein. Samples from the standard curve and ING-1-chelate conjugate unknowns are then incubated with $5 \times 10^5$ HT29 cells at 4° C. for 1 hour. After extensive washing to remove unbound antibody, the cells are resuspended in 100 uL flow buffer and incubated at 4° C. for 1 hour with goat-anti-human antibody labelled with fluorescene isothiocyanate. After further washing in flow buffer, the samples are analyzed by flow cytometry on a Coulter EPICS 753 flow cytometer. Fluorescein isothiocyanate (FITC) and propidium iodine (PI) are excited using the 488 nm emission line of an argon laser. The output is set at 500 mw in light regulation mode. Single cells are identified by 90 degree and forward angle light scatter. Analysis windows are applied to these parameters to separate single cells from aggregates and cell debris. Fluorescence from FITC and propidium are separated with a 550 nm long pass dichroic filter and collected through a 530 nm band pass filter (for FITC), and a 635 nm band pass filter (for PI). Light scatter parameters are collected as integrated pulses, and fluorescence is collected as log integrated pulses. Dead cells are excluded from the assay by placing an analysis window on cells negative for PI uptake. The mean fluorescence per sample (weighted average from 2500 cells) is calculated for each histogram. FITC calibration beads are analysed in each experiment to establish a fluorescence standard curve. The average fluorescence intensity for each sample is then expressed as the average FITC equivalents per cell. Immunoreactivity is calculated by comparing the average fluorescence intensity of the ING-1-chelate conjugate with values from the standard curve.

Example 50

Immunoreactivity Assay by ELISA

The antigen to which the antibody, ING-1, binds is prepared from LS174T or HT-29 cells (available from ATTC) by scraping confluent monolayers of cells from the walls of culture flasks with a cell scraper. The cells from many flasks are combined and a sample is taken and counted to estimate the total number of cells harvested. At all times the cells are kept on ice. Following centrifugation of the cells at 1500 rpm for 10 minutes at 4° C., the cells are washed once in 25 mL ice-cold 50 mM sodium phosphate buffer, pH 7.4, supplemented with 150 mM sodium chloride (PBS), pelleted under the same conditions and transfered in 10 mL PBS to an ice-cold glass mortar. The cells are homogenized at 4° C. using a motor-driven pestle and then centrifuged at 3000×g for 5 minutes. The antigen-rich supernatant is removed from the other cell debris and subjected to further centrifugation at 100,000×g for one hour at 4° C. The pellet (antigen fraction) from this final step is suspended in 100 uL of PBS for every million cells harvested. Following an estimate of the protein concentration (BioRad BCA protein assay using bovine immunoglobulin as the protein standard), the antigen is stored at −20° C. until use. Each well of a 96-well Costar microtiter plate is coated with antigen by adding 100 uL/well of cell lysate (10 mg/mL) prepared as above. The microtitre plates are allowed to dry overnight in a 37° C. incubator. After washing the plates five times with 0.05% Tween-20 (Sigma), they are blotted dry. The wells of each plate are blocked by adding 125 uL/well of a 1% BSA (bovine serum albumin, Sigma) solution in PBS and incubated for 1 hour at room temperature. The plates are washed five times with 0.05% Tween-20. Samples (50 uL/well in duplicate) of ING-1-chelate conjugate and standard ING-1 antibody solutions are prepared at a range of concentrations in 1% BSA in PBS. Biotinylated ING-1 (1.0 mg/mL in 0.1% BSA) is added to each well (50 uL/well) and the plates are then incubated for 2 hours at room temperature. Following five washes with 0.05% Tween-20, the plates are blotted dry and incubated at room temperature for one hour with dilute (1:2000 in 0.1% BSA) streptavidin-alkaline phosphatase (Tago). After a further five washes, color is developed in each well upon the addition of 100 uL per well of phosphatase substrate reagent (Sigma). After one hour at room temperature, the color is read using a 405 nm filter in a Titertek Multiscan microplate reader.

Example 51

SDS PAGE Gel Electrophoresis

A sample of ING-1-chelate conjugate from example 46 is subjected to electrophoresis on Novex 8%–16% reduced and native polyacrylamide gels using SDS buffers to estimate the apparent molecular weight and the degree of heterogeneity of the preparation. Using standards of known molecular weight run on the same gel, a standard curve is constructed of the distance traveled versus the log of the molecular weight. From this standard curve, the relative molecular weights of the bands associated with each conjugate preparation are determined.

Example 52

Determination of Antibody Aggregate Formation by Size-exclusion HPLC

A 30 cm×7.5 mm TSK-G3000SW size-exclusion HPLC column (Supelco), fitted with a guard column of the same material, is equilibrated with 12 column volumes of 10 mM sodium phosphate buffer, pH 6.0, supplemented with 150 mM sodium chloride, using a Waters 600E HPLC system with a flow rate of 1.0 mL per minute at 400–600 PSI. A sample (25 uL) of BioRad gel filtration protein standards is injected onto the column. The retention time of each standard is monitored by a Waters 490 UV detector set at 280 nm. Following the recovery of the final standard, the column is washed with a further 10 volumes of 10 mM sodium phosphate buffer, pH 6.0, supplemented with 150 mM sodium chloride. Samples (50 uL) of native ING-1 antibody and of ING-1-chelate from example 46 at 200 ug/mL are separately injected onto the column and their retention times recorded. From the areas of the retained peaks and the retention time, the amount of aggregated material in the ING-1-chelate conjugate sample is calculated.

Example 53

Time Delayed fluorescence of the Eu+3 complex of 3,9-bis(carboxymethyl)-6-{6-[4'-(4-nitrophenyl)-2, 2':6',2"-terpyridyl]-methylaminocarbonylmethyl}-3, 6,9-triazaundecanedioic acid A solution of the Eu chelate of example 25 at 3 umol/mL in water was irradiated at 385 nm in a Perkin Elmer LS50 Spectrofluorometer, and emission was monitored after a 400 microsecond time delay. The wavelength of maximum emission intensity was observed at 618 nm, with other less intense emission maxima at 685, 690 and 705 nm. Fluorescence emission could be detected at 618 nm at concentrations as low as 0.1 nm/mL of complex.

The invention has been described in detail with particular reference to certain preferred embodiments thereof, but it will be understood that variations and modifications can be effected within the spirit and scope of the invention.

What is claimed is:

1. A method for diagnostic imaging a site in a patient comprising the steps of
   a) administering to the patient an effective amount of a targeting radioactive immunoreagent capable of targeting said site, and
   b) imagewise activating a radiation sensitive element or device with the radiation emitted from the targeted site: said targeting radioactive immunoreagent comprising a metal radionuclide ion,
      a complexing agent, and
      an immunoreactive group linked to said complexing agent said complexing agent having the structure

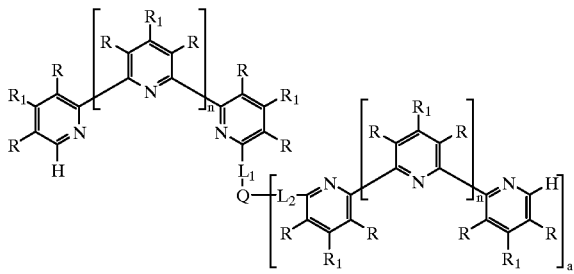

wherein
each R and $R_1$ is independently selected from hydrogen, alkyl, alkoxy, alkylthio, N,N-dialkylamino, alkylformamido, aryl, heterocyclyl and a protein reactive group;
each of $L_1$ and $L_2$ is a linking group independently selected from a chemical bond, a methylene group (—$CH_2$—) and an imino group;
Q is a chelating group;
each n is independently 1, 2, 3 or 4; and
a is 0 or 1.

2. The method of claim 1 wherein in said immunoreagent n is 1.

3. The method of claim 1 wherein in said immunoreagent a is 1.

4. The method of claim 1 wherein in said immunoreagent the protein reactive group is selected from the group consisting of amino; aminoalkyl; aminoaryl; alkylamino; arylamino; hydrazino; alkylhydrazino; arylhydrazino; carbazido; semicarbazido; thiocarbazido; hydrazidoalkyloxy; azidocarbonylalkyloxy; aryloxycarbonyloxyalkyloxy; triazines; aryloxycarbonyl(polyoxyalkyl)oxy; thiosemicarbazido; sulfhydryl; sulfhydrylalkyl; sulfhydrylaryl; hydroxy; carboxy; carboxyalkyl; carboxyaryl; active halogen containing groups; 2-leaving group-substituted ethylsulfonyl and ethylcarbonyl; vinylsulfonyl; vinyl sulfonylalkyloxy; vinyl sulfonylalkylpoly(oxyalkyl)oxy; vinylcarbonyl; oxiranyl; isocyanato; isothiocyanato; aldehydo; aziridinyl; succinimidoxycarbonyl; activated acyl groups; anhydride groups; thioester groups; active carbonates; sulfonic acid esters; phosphoramidates; cyanuric monochlorides and dichlorides; and groups that are linked to protein or modified protein via a crosslinking agent.

5. The method of claim 4 wherein in said immunoreagent the protein reactive group is selected from the group consisting of chloromethylphenyl, chloromethylcarbonyl, iodomethylcarbonyl, 2-chloroethylsulfonyl, 2-chloroethylcarbonyl, carboxylic acid halide groups, alkylhydrazino, arylhydrazino, semicarbazido, thiocarbazido, thiosemicarbazido, isocyanato and isothiocyanato, vinyl sulfonylalkyloxy, vinyl sulfonylalkyl(polyoxyalkyl)oxy, amidatoalkyloxy, hydrazidoalkyloxy, azidocarbonylalkyloxy, aryloxycarbonyloxyalkyloxy, aryloxycarbonyl(polyoxyalkyl)oxy, 4,6-dichloro-2-triazinyloxy, dichlorotriazinyl-(polyoxyalkyl)oxy, 4-alkoxy-6-chloro-2-triazinloxy, 4-alkoxy-6-chloro-2-triazinyl(polyoxyalkyl)oxy, formylalkyl, aminoalkyl, thioalkyimidoaminoalkyloxy, active esters, active anhydrides, nitrophenylcarbonates, arylcarbonatoaryl, alkylcarbonatoaryl, arylcaronatoalkyl, alkylcarbonatoalkyl, mixed anhydrides, thioalkylcarbonylaminoalkyloxy, succinimidoxycarbonyl, maleimidoalkylcarbonylaminoalkyloxy, azido, 4,6-dichloro-2-triazinylamino, 4,6-dichloro-2-triazinyloxyalkyl, 4,6-dichloro-2-triazinyloxyaryl, 4,6-dichlorotriazinyl-2-oxy (polyalkyloxy), iodoalkylcarbonylamino, alkylamino, arylamino, amidatoalkylamino and amidatoarylalkylamino.

6. The method of claim 5 wherein in said immunoreagent the protein reactive group is selected from the group consisting of sulfhydryl, amino, aryl carbonato alkyl, active esters, isothiocyanato and thiosemicarbazido.

7. The method of claim 1 wherein in said immunoreagent the immunoreactive group is selected from the group consisting of enzymes, amino acids, peptides, polypeptides, proteins, lipoproteins, lipids, phospholipids, glycoproteins, hormones, growth factors, steroids, vitamins, polysaccharides, viruses, protozoa, fungi, parasites, rickettsia, molds, components of molds, blood components, tissue and organ components, pharmaceuticals, haptens, lectins, toxins, nucleic acids, oligonucleotides, antibodies, anti-antibodies, antibody fragments, antigenic materials, avidin, and, biotin.

8. The method of claim 7 wherein in said immunoreagent the immunoreactive group is an antibody or a fragment of an antibody.

9. The method of claim 7 wherein in said immunoreagent the immunoreactive group is a protein.

10. The method of claim 1 wherein in said immunoreagent the radionuclide ion is selected from the group consisting of Sc, Fe, Pb, Ga, Y, Bi, Lu, Mn, Cu, Cr, Zn, Ge, Mo, Tc, Ru, In, Sn, Sm, Sr, Eu, Dy, Sb, W, Re, Po, Ta and Tl ions.

11. The method of claim 10 wherein in said immunoreagent the radionuclide ion is selected from the group consisting of $^{44}Sc$, $^{111}In$, $^{212}Pb$, $^{68}Ga$, $^{90}Y$, $^{177}Lu$ $^{186}Re$, $^{188}Re$, $^{64}Cu$, $^{67}Cu$, $^{99m}Tc$, $^{87}Y$ and $^{212}Bi$ ions.

12. The method of claim 11 wherein in said immunoreagent the metal radionuclide ion is $^{90}Y^{+++}$.

13. The method of claim 8 wherein in said immunoreagent the antibody is selected from the group consisting of B72.3, 9.2.27, C174, D612, UJ13A, NRLU-10, 7E11C5, CC49, TNT, PR1A3, ING-1, B174, C174 and B43 antibodies.

14. The method of claim 13 wherein in said immunoreagent the antibody is selected from B72.3, B43, C174 and ING-1 antibodies.

15. The method of claim 13 wherein in said immunoreagent the metal radionuclide ion is $^{90}Y^{+++}$.

16. A method of diagnostic imaging a site in a patient comprising the steps of
a) administering to the patient an effective amount of a targeting immunoreagent capable of targeting said site, and
b) imagewise activating a nuclear magnetic resonance detection sensor element or device which is sensitive to a change in one or more nuclear magnetic relaxation properties of an isotope at said site while exposed to a controlled magnetic field environment:
said immunoreagent comprising
a paramagnetic metal ion,
a complexing agent, and
an immunoreactive group linked to said complexing agent, said complexing agent having the structure

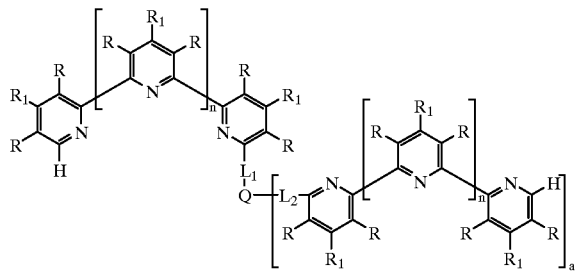

wherein each R and $R_1$ is independently selected from hydrogen, alkyl, alkoxy, alkylthio, N,N-dialkylamino, alkylformamido, aryl, heterocyclyl, and a protein reactive group;

each $L_1$ and $L_2$ is a linking group independently selected from a chemical bond, a methylene group (—$CH_2$—) and an imino group;

Q is of a chelating group;

each n is independently 1, 2, 3 or 4; and a is 0 or 1.

17. The method of claim 16 wherein in said immunoreagent the paramagnetic metal ion is an ion of a metal of atomic number 21–29, 42, 44 or 57–71.

18. The method of claim 17 wherein in said immunoreagent the paramagnetic metal ion is an ion of a metal of atomic number 57–71.

19. The method of claim 17 wherein in said immunoreagent the paramagnetic metal ion is an ion of a metal selected from the group consisting of Cr, V, Mn, Fe, Co, Ni, Cu, La, Ce, Pr, Nd, Pm, Sm, Eu, Gd, Tb, Dy, Ho, Er, Tm, Yb and Lu.

20. The method of claim 19 wherein in said immunoreagent the paramagnetic metal ion is selected from the group consisting of $Cr^{+3}$, $Cr^{+2}$, $V^{+2}$, $Mn^{+3}$, $Mn^{+2}$, $Fe^{+3}$, $Fe^{+2}$, $Co^{+2}$, $Gd^{+3}$ and $Dy^{+3}$.

* * * * *